US012752074B2

(12) United States Patent
Granat et al.

(10) Patent No.: US 12,752,074 B2
(45) Date of Patent: Oct. 6, 2026

(54) CATHETER

(71) Applicant: Nowwell Flow Technology AS, Odda (NO)

(72) Inventors: Leif Granat, Stockholm (SE); Niklas Herou, Jönköping (SE)

(73) Assignee: Nowwell Flow Technology AS, Odda (NO)

( * ) Notice: Subject to any disclaimer, the term of this patent is extended or adjusted under 35 U.S.C. 154(b) by 0 days.

(21) Appl. No.: 19/441,409

(22) Filed: Jan. 6, 2026

(65) Prior Publication Data

US 2026/0131106 A1 May 14, 2026

Related U.S. Application Data

(63) Continuation of application No. 19/263,935, filed on Jul. 9, 2025, now Pat. No. 12,539,390, which is a continuation of application No. 18/928,643, filed on Oct. 28, 2024.

(30) Foreign Application Priority Data

Oct. 27, 2023 (GB) ..................................... 2316498
Jan. 22, 2024 (GB) ..................................... 2400820

(51) Int. Cl.
*A61M 25/00* (2006.01)
*A61M 25/10* (2013.01)

(52) U.S. Cl.
CPC .... *A61M 25/0017* (2013.01); *A61M 25/0041* (2013.01); *A61M 25/0043* (2013.01); *A61M 25/0069* (2013.01); *A61M 25/007* (2013.01); *A61M 25/10* (2013.01); *A61M 2210/1085* (2013.01); *A61M 2210/1089* (2013.01)

(58) Field of Classification Search
CPC .......... A61M 25/0017; A61M 25/0041; A61M 25/0043; A61M 25/0069; A61M 25/007; A61M 25/10; A61M 2210/1085; A61M 2210/1089
See application file for complete search history.

(56) References Cited

U.S. PATENT DOCUMENTS

| | | | |
|---|---|---|---|
| 4,419,985 | A | 12/1983 | Trick |
| 4,575,371 | A | 3/1986 | Nordqvist et al. |
| 4,710,169 | A | 12/1987 | Christopher |
| 4,822,333 | A | 4/1989 | Lavarenne |

(Continued)

FOREIGN PATENT DOCUMENTS

| | | | |
|---|---|---|---|
| CA | 3198386 | A1 | 4/2022 |
| CN | 208756758 | U | 4/2019 |

(Continued)

*Primary Examiner* — Susan S Su
*Assistant Examiner* — Erin A Kim
(74) *Attorney, Agent, or Firm* — Command IP LLP; Pejman Yedidsion

(57) ABSTRACT

A catheter insertable into a urethra for installation in a user's bladder and urethra, the catheter comprising: a urine conduit comprising a first urine inlet and a urine outlet; and an inlet protector extending outwardly from the urine conduit from a position between the first urine inlet and the urine outlet, where the inlet protector functions to protect the urine inlet by separating it from contact with the bladder wall and thus keeping it out of contact with tissue.

20 Claims, 25 Drawing Sheets

(56) References Cited

U.S. PATENT DOCUMENTS

| | | | | | |
|---|---|---|---|---|---|
| 5,275,587 | A | | 1/1994 | Kubalak et al. | |
| 5,417,657 | A | * | 5/1995 | Hauer ............... | A61M 25/0017 604/523 |
| 5,536,240 | A | | 7/1996 | Edwards et al. | |
| 5,634,878 | A | | 6/1997 | Grundei et al. | |
| 5,711,314 | A | | 1/1998 | Ardito | |
| 5,785,694 | A | | 7/1998 | Cohen et al. | |
| 6,042,535 | A | | 3/2000 | Porter | |
| 6,066,088 | A | | 5/2000 | Davis | |
| 6,167,886 | B1 | | 1/2001 | Engel et al. | |
| 7,470,469 | B1 | | 12/2008 | Michal et al. | |
| 10,946,168 | B1 | | 3/2021 | Palmer | |
| 12,023,457 | B2 | | 7/2024 | Mann et al. | |
| 12,156,971 | B2 | | 12/2024 | Babu et al. | |
| 12,539,390 | B2 | * | 2/2026 | Granat .............. | A61M 25/0017 |
| 2002/0065512 | A1 | | 5/2002 | Fjield et al. | |
| 2003/0144628 | A1 | | 7/2003 | Sirimanne | |
| 2005/0107735 | A1 | | 5/2005 | Lennox et al. | |
| 2006/0129095 | A1 | | 6/2006 | Pinchuk | |
| 2006/0259061 | A1 | | 11/2006 | Kick et al. | |
| 2007/0276342 | A1 | | 11/2007 | Lin et al. | |
| 2012/0108902 | A1 | | 5/2012 | Frassica et al. | |
| 2013/0079755 | A1 | | 3/2013 | House | |
| 2014/0012180 | A1 | | 1/2014 | Levin et al. | |
| 2014/0081075 | A1 | | 3/2014 | Salama | |
| 2017/0095323 | A1 | | 4/2017 | Garcia et al. | |
| 2019/0091003 | A1 | | 3/2019 | Forsell | |
| 2020/0069911 | A1 | | 3/2020 | Hazan et al. | |
| 2020/0178872 | A1 | | 6/2020 | Imran et al. | |
| 2020/0222660 | A1 | | 7/2020 | Erbey, II et al. | |
| 2020/0253536 | A1 | | 8/2020 | McKinney | |
| 2021/0177564 | A1 | | 6/2021 | Lima | |
| 2021/0338979 | A1 | | 11/2021 | Palmer | |
| 2022/0047368 | A1 | | 2/2022 | Block et al. | |
| 2022/0305232 | A1 | | 9/2022 | Babu et al. | |
| 2022/0362509 | A1 | | 11/2022 | Arevalos et al. | |
| 2023/0001155 | A1 | | 1/2023 | Herrera | |
| 2023/0218378 | A1 | | 7/2023 | Kristensen et al. | |
| 2023/0381454 | A1 | | 11/2023 | Lenneman et al. | |
| 2023/0390536 | A1 | * | 12/2023 | Suresh .............. | A61M 25/0017 |
| 2024/0189574 | A1 | | 6/2024 | Liu et al. | |

FOREIGN PATENT DOCUMENTS

| | | | |
|---|---|---|---|
| CN | 210020551 | U | 2/2020 |
| DE | 102008057177 | A1 | 5/2010 |
| EP | 3641871 | A1 | 4/2020 |
| KR | 20200055522 | A | 5/2020 |
| WO | 9206731 | A1 | 4/1992 |
| WO | 9903423 | A1 | 1/1999 |
| WO | 2004056414 | A1 | 7/2004 |
| WO | 2006045809 | A1 | 5/2006 |
| WO | 2007005734 | A2 | 1/2007 |
| WO | 2007133776 | A2 | 11/2007 |
| WO | 2008011638 | A2 | 1/2008 |
| WO | 2008067557 | A2 | 6/2008 |
| WO | 2009108243 | A1 | 9/2009 |
| WO | 2010149174 | A1 | 12/2010 |
| WO | 2011014201 | A1 | 2/2011 |
| WO | 2013004236 | A1 | 1/2013 |
| WO | 2014077881 | A1 | 5/2014 |
| WO | 2014077886 | A1 | 5/2014 |
| WO | 2014113257 | A2 | 7/2014 |
| WO | 2015028786 | A1 | 3/2015 |
| WO | 2015089189 | A2 | 6/2015 |
| WO | 2015090338 | A1 | 6/2015 |
| WO | 2016204858 | A1 | 12/2016 |
| WO | 2018001968 | A1 | 1/2018 |
| WO | 2018114682 | A1 | 6/2018 |
| WO | 2018134591 | A1 | 7/2018 |
| WO | 2018136306 | A1 | 7/2018 |
| WO | 2018148658 | A1 | 8/2018 |
| WO | 2018200643 | A1 | 11/2018 |
| WO | 2019040694 | A1 | 2/2019 |
| WO | 2019092686 | A1 | 5/2019 |
| WO | 2019113077 | A1 | 6/2019 |
| WO | 2019152551 | A1 | 8/2019 |
| WO | 2020006527 | A1 | 1/2020 |
| WO | 2020103996 | A1 | 5/2020 |
| WO | 2020160738 | A1 | 8/2020 |
| WO | 2020173531 | A1 | 9/2020 |
| WO | 2020176899 | A1 | 9/2020 |
| WO | 2020252003 | A1 | 12/2020 |
| WO | 2021081539 | A1 | 4/2021 |
| WO | 2021116295 | A1 | 6/2021 |
| WO | 2021183718 | A1 | 9/2021 |
| WO | 2021213975 | A1 | 10/2021 |
| WO | 2021214479 | A1 | 10/2021 |
| WO | 2021239197 | A1 | 12/2021 |
| WO | 2021242487 | A1 | 12/2021 |
| WO | 2021242676 | A1 | 12/2021 |
| WO | 2021242745 | A1 | 12/2021 |
| WO | 2021250243 | A1 | 12/2021 |
| WO | 2022111779 | A2 | 6/2022 |
| WO | 2022221509 | A1 | 10/2022 |
| WO | 2022224071 | A1 | 10/2022 |
| WO | 2022231941 | A1 | 11/2022 |
| WO | 2022243688 | A1 | 11/2022 |
| WO | 2022245585 | A1 | 11/2022 |
| WO | 2023278344 | A1 | 1/2023 |
| WO | 2023154700 | A1 | 8/2023 |
| WO | 2023163704 | A1 | 8/2023 |
| WO | 2023217727 | A1 | 11/2023 |
| WO | 2023232212 | A1 | 12/2023 |
| WO | 2024006777 | A2 | 1/2024 |
| WO | 2024137166 | A1 | 6/2024 |
| WO | 2024137169 | A1 | 6/2024 |
| WO | 2024191800 | A2 | 9/2024 |
| WO | 2024192040 | A1 | 9/2024 |
| WO | 2024229021 | A1 | 11/2024 |
| WO | 2024233231 | A1 | 11/2024 |
| WO | 2024243603 | A1 | 11/2024 |
| WO | 2025019209 | A1 | 1/2025 |
| WO | 2025037089 | A1 | 2/2025 |
| WO | 2025037091 | A1 | 2/2025 |
| WO | 2025054378 | A1 | 3/2025 |
| WO | 2025054686 | A1 | 3/2025 |

* cited by examiner

CATHETER

CROSS-REFERENCE TO RELATED APPLICATIONS

This application is a continuation of United States Non-Provisional Ser. No. 19/263,935, filed Jul. 9, 2025, which is a continuation of United States Non-Provisional Ser. No. 18/928,643, filed Oct. 28, 2024, which claims the priority benefit of United Kingdom Application No. GB 2316498.1 filed Oct. 27, 2023 and GB 2400820.3 filed Jan. 22, 2024, the contents of all of which are hereby incorporated herein by reference in their entireties for all purposes.

FIELD

The present invention relates to catheters for urinary flow.

BACKGROUND

Transurethral catheterisation or urinary catheterisation involves passage of a catheter into the urinary bladder via the urethra.

Typically, a Foley catheter is used for continuous drainage of the bladder. It is usually defined as an indwelling balloon-retention catheter used by medical professionals to provide a means of bladder drainage through the urethra. A Foley catheter usually has at least two separated channels, or lumens, running down its length. One lumen, open at both ends, drains urine from the bladder. The other has a valve on the outside end and connects to a balloon at the inside tip. The balloon is usually inflated with sterile water or saline when it lies inside the bladder to stop it from slipping out. Manufacturers usually produce Foley catheters using silicone or coated natural latex. Foley catheters may be coated with e.g. polytetrafluoroethylene, hydrogel, silicon elastomer, or various antimicrobial agents.

Foley catheters may have 3 lumens where the third lumen is used for bladder irrigation, or 4 lumens where the fourth lumen is used for irrigation or aspiration of a surgical site. It can also be used to medicate the lower urinary tract.

Indications for urinary catheterisation include urinary retention, including, e.g. acute and chronic urinary retention, maintaining a continuous outflow of urine for patients with voiding difficulties, perioperative use for selected surgical procedures, patients undergoing urological surgery, anticipated prolonged duration of surgery, patient requires prolonged immobilisation, to assist in healing of open sacral or perineal wounds in incontinent patients, to facilitate continence and maintain skin integrity, management of intractable incontinence, and to improve comfort for end of life care.

Indications for urinary catheterisation further include urinary incontinence. One of the causes of urinary incontinence (UI)—the involuntary leakage of urine—is the loss or weakening of the urethral sphincter which affects approximately 5% of people around the globe. In men, UI is particularly common in people with prostate cancer who have undergone a prostatectomy, affecting approximately 10% of patients undergoing prostatectomy annually in the USA. UI is also a common problem for patients with an enlarged prostate, affecting 30-40% of patients undergoing transurethral resection of the prostate (TURP) annually in the USA. In women, pregnancy and childbirth may lead to weak pelvic floor muscles or damage the surrounding nerves which can make the urethral sphincter incompetent. UI severely affects the quality of life in patients of all ages.

Intermittent catheters are inserted into the bladder for just long enough to drain the bladder, and can be removed when the flow of urine stops. Such catheters are generally single-use catheters with a single lumen to drain urine from the bladder and are disposed of after use.

SUMMARY OF THE INVENTION

When viewed from a first aspect, the invention provides a catheter insertable into a urethra for installation in a user's bladder and urethra, the catheter comprising:

- a urine conduit comprising a first urine inlet and a urine outlet; and
- an inlet protector extending outwardly from the urine conduit from a position between the first urine inlet and the urine outlet.

The inlet protector functions to protect the urine inlet by separating it from contact with the bladder wall and thus keeping it out of contact with tissue. Problems can arise in existing catheters when the process of evacuating the bladder causes tissue from the bladder wall to be sucked into the urine inlet. There are a number of issues with this. For example, the tissue can get stuck to the catheter which blocks the urine inlet. The tissue can also be damaged by this process, resulting in bleeding. Also, small pieces of tissue can lodge within the catheter causing blockage and biofouling. This reduces the available size of the urine inlet and/or urine conduit which reduces the flow rate. A high flow rate is better as it flushes any fouling or urine deposits (e.g. due to crystallisation over time of residual urine) out of the catheter. A lower flow rate is less effective at such flushing so that deposits build up quicker and present a greater infection risk, thus reducing the time that the catheter can remain in place. As the inlet protector extends outwardly from the urine conduit from a position between the urine inlet and the urine outlet (i.e. so that the urine inlet is held more towards the bladder, away from the urethra and the urethral opening of the bladder (where the urethra enters the bladder), i.e. the urethral neck) it keeps the urine inlet slightly separated from the bladder wall tissue and thus ensures a good flushing flow rate with reduced risk of fouling.

In a set of embodiments, the inlet protector is foldable such that it axially overlaps the first urine inlet. Here, axially should be interpreted to mean in a direction parallel to a longitudinal axis of the catheter. In other words, the inlet protector is foldable such that at least one plane can be drawn perpendicular to the longitudinal axis of the catheter that intercepts both the first urine inlet and the inlet protector. The inlet protector may be foldable such that it axially overlaps the entirety of the inlet, or it may axially overlap only a portion of the first urine inlet. In some embodiments there may also be overlap in the circumferential direction (either full or partial circumferential overlap) between the inlet protector and the first urine inlet. However, in other embodiments there could be axial overlap, but no circumferential overlap, e.g. where the inlet protector comprises flaps that fold up circumferentially adjacent to the first urine inlet. Where the first urine inlet comprises a plurality of holes in the side wall of the urine conduit, the inlet protector may axially overlap at least a hole located axially closest to the urine outlet.

Overlapping of the urine inlet by the inlet protector during insertion and/or removal can also result in less damage during the insertion/removal process. In particular, depending on the method of manufacturing, the urine inlet may have sharp edges. For example, a common way of manufacturing catheters is to punch the urine inlet in the side of the urine conduit. This punching operation can leave a relatively sharp edge that scrapes the tissue as the catheter is inserted and/or removed along the urethra. The tissue in the urethra and bladder is very soft and so, even though the materials of the catheter may be relatively soft and flexible, the sharp edge from punching the urine inlet can still cause abrasion of the tissue. Having the inlet protector overlap the urine inlet during insertion and/or removal can therefore reduce the damage or irritation caused by such edges. Such damage arises from any catheter use, but it is of particular concern in relation to intermittent catheters which may be used repeatedly for single use bladder emptying. In particular, some patients may self-catheterise and may therefore use such an intermittent catheter many times a day for bladder emptying. Each use involves an insertion process and a removal process which means that there is significant potential for damage or irritation.

It will be appreciated that an inlet protector as described above (i.e. with the first urine inlet between the inlet protector and the proximal end of the urine conduit, i.e. the end furthest from the urine outlet and first inserted into the urethral meatus during insertion of the catheter into a user) can overlap with the urine inlet during removal. An inlet protector may additionally (or alternatively) be located between the first urine inlet and the proximal end of the urine conduit and arranged to at least partially overlap the urine inlet during insertion. In some embodiments the (or each) inlet protector may fully overlap the urine inlet during the insertion/removal process so as to fully cover all edges of the urine inlet (i.e. such that the inlet protector is interposed between the urine inlet and the urethra wall during the insertion/removal process).

In a set of embodiments, the first urine inlet is located in a side wall of the urine conduit. The first urine inlet may comprise a hole formed in a side wall of the urine conduit. The first urine inlet may comprise a plurality of holes formed in a side wall of the urine conduit. The plurality of holes may be located at substantially the same longitudinal position along the urine conduit. In other words, the plurality of holes may be located around the cross-sectional perimeter of the urine conduit at substantially the same location along the length thereof.

In a set of embodiments, the inlet protector is located substantially adjacent to the first urine inlet such that, in use, the first urine inlet is located near to the urethral neck. In a set of embodiments, the urine outlet is located outside of the body when the catheter is installed in a user.

In a set of embodiments, the urine conduit has a substantially circular cross-section. The urine conduit may have a substantially tubular shape. The urine conduit may be formed from a flexible material e.g. silicone, so as to allow the conduit to conform to the longitudinal shape of the urethra. It may also be able to laterally conform to the cross-sectional shape of the urethra.

In a set of embodiments, the proximal end of the urine conduit may have a rounded shape. This may advantageously reduce pressure on the urethral meatus, and the urethra, during insertion of the catheter, thereby improving comfort and decreasing risk of damage to the user. The rounded end may also advantageously improve comfort and reduce risk of damage while the catheter is installed in a user, by ensuring that no sharp or angled edges may come into contact with the bladder wall. The rounded proximal end of the urine conduit may be closed off. In a set of embodiments, the proximal end of the urine conduit comprises a hole sized to accommodate insertion of instruments therethrough (e.g. pH sensors, temperature sensors, etc.).

The inlet protector may be arranged to be movable between a covering position in which it covers the first urine inlet and an open position in which it does not cover the first urine inlet.

The inlet protector may be or may comprise a skirt, a disk, plate, membrane, dish, one or more flaps or an outwardly extending border. The inlet protector may be or may comprise a resilient skirt, a resilient disk, a resilient plate, a resilient dish, or an outwardly extending resilient border.

In a set of embodiments, the inlet protector contacts the bladder wall if the catheter moves in the direction of removal from the urethra. The inlet protector may thereby inhibit the catheter from moving further into the urethra.

In a set of embodiments, the inlet protector is positioned substantially adjacent to the first urine inlet. This ensures that if the first urine inlet moves into the urethra, the inlet protector will fold over the urine inlet thereby protecting it from tissue contact and thus protecting it from potential tissue suck-in or fouling problems. When the urine inlet moves back into the bladder, the inlet protector can fold back away from the urine inlet, leaving it open for urine flow. If the inlet protector is resilient, the resilience will aid in positioning of the catheter by resisting movement of the urine inlet into the urethra. Such movement may prevent (or hinder) fluid communication between the first urine inlet and urine contained in the bladder, so ensuring that the urine inlet remains in the bladder or returns to it quickly, ensures that the catheter remains functional while it is installed in a user. If the inlet protector does move into the urethra and block flow, it will generally move back into the bladder even in the absence of significant resilience in the inlet protector. Normal movement of the body will generally cause the catheter to move up and down a bit such that it will eventually return to the optimal position. A resilient inlet protector makes this process a little faster and increases the likelihood that the catheter remains in the optimal position. A patient can also learn to manually adjust the catheter position by pushing it in slightly in case they sense that the bladder is not emptying properly.

In a set of embodiments, the inlet protector and the urine conduit are integrally moulded. This may provide a convenient mechanism for manufacturing the catheter in a manner which ensures the inlet protector remains attached to the catheter in the same position when it is installed.

The inlet protector may comprise a skirt. The skirt may surround (or substantially surround) the circumference of the urine conduit. This can increase the protection provided by the inlet protector as it provides a separator that surrounds the urine inlet (or inlets).

The inlet protector may comprise a resilient skirt. The inlet protector may function as a first positioning structure. The skirt being resilient may help ensure that it can conform to the shape of the urethral opening when the catheter is installed, and thus prevent it from digging into the bladder wall and causing damage or discomfort to the user.

In some embodiments the inlet protector may be smooth and substantially flat. In other embodiments it may comprise at least one radially extending ridge. The radially extending ridge may have a greater thickness than the rest of the inlet protector. For example, the inlet protector may be formed as a substantially smooth and thin disc with one or more radially extending ridges of greater thickness. In a set of embodiments, the inlet protector comprises a plurality of radially extending ridges having a portion of material extending therebetween, each of the radially extending ridges having a greater thickness than the material extending therebetween. The ridges and the material extending therebetween may be integrally moulded and may be formed from the same material—e.g. silicone. These ridges may provide resiliency to the inlet protector so as to cause it to return to a non-stressed position after deviating from the non-stressed position due to external forces applied thereto. In such embodiments the inlet protector may be a resilient skirt.

In some embodiments, at least one radially extending ridge is positioned adjacent to the urine inlet. When the inlet protector folds over the urine inlet (e.g. during insertion or removal), the radially extending ridge prevents the inlet protector from completely obstructing the urine inlet. Although the urine inlet may be obstructed to a large degree in this configuration, ensuring that a small opening remains allows urine to exit from the bladder through the catheter, even if the flow rate is reduced, i.e. complete blockage is prevented.

As the inlet protector folds over the urine inlet, it may wrinkle due to its change of shape. Such wrinkles can also have the desired effect of preventing complete blockage of the urine inlet, but an appropriately designed and/or positioned radially extending ridge (or ridges) improves the reliability.

The wrinkles that may form during the folding process can also affect the overall width of the urine conduit during insertion and removal. It is thus desirable to direct such wrinkles in a predictable manner so as to distribute them evenly around the conduit and minimise the overall diameter. The positioning of radial ridges can be selected so as to bias the folding process into a particular configuration, e.g. one that is optimal for insertion/removal. It will be appreciated that the number and position of radial ridges for such folding may be influenced by various factors such as size, thickness and stiffness of the inlet protector and size and thickness of the conduit. However, in some particularly preferred embodiments, it has been found that five radially extending ridges result in a folding process that distributes the inlet protector evenly around the conduit during insertion/removal.

In a set of embodiments, the outer ends of the radially extending ridges taper in thickness from their thickest points to the thickness of the material extending therebetween. The upper surfaces of the ridges may also have a rounded profile. Such embodiments may advantageously ensure that the surface of the inlet protector having the radially extending ridges protruding therefrom has an overall smooth surface without any sharp or angled edges.

In some embodiments, each of the radially extending ridges has a thickness at its thickest point that is at least 2 times greater than a thickness of the material extending therebetween. In some embodiments, each of the radially extending ridges has a thickness at its thickest point that is up to 10 times greater than a thickness of the material extending therebetween. In some embodiments, the radially extending ridges have a thickness at their thickest points of from 0.1 mm to 2 mm. In some embodiments, the portions of material extending between the radially extending ridges have a thickness of from 0.05 mm to 0.5 mm. Such thickness ratios and ranges may provide a good balance of flexibility and resiliency for the skirt.

In a set of embodiments, when in a non-stressed position, the inlet protector comprises a first face which is substantially smooth and a second face comprising the radially extending ridges protruding therefrom, the first face facing away from the first urine inlet and the second face facing towards the first urine inlet. In other words, the radially extending ridges may only be present on one face of the inlet protector. This may provide the inlet protector with a required level of resiliency through inclusion of the ridges while also ensuring that the face which may contact the bladder wall (i.e. the first face facing away from the first urine inlet) is smooth so as to minimise the risk of urine getting trapped underneath the inlet protector. It may also help improve comfort by ensuring that the ridges do not protrude into the bladder wall.

In a set of embodiments, the inlet protector, when in a non-stressed position, is substantially planar. The inlet protector may form a substantially disc-like shape when in a non-stressed position. Such embodiments may enable the inlet protector to function as a positioning structure as described above.

In some embodiments, the inlet protector may be substantially flat on both faces (i.e. without any ridges to provide resiliency). The inlet protector may still have sufficient resiliency to bias it to a non-stressed planar shape, extending away from the urine conduit.

In a set of embodiments, the inlet protector permits folding so as to conform to the shape of the exterior surface of the urine conduit. In a set of embodiments, the inlet protector permits folding in two different directions—towards the first urine inlet, and towards the urine outlet. This may advantageously allow the inlet protector to collapse around the urine conduit when sufficient force is applied thereto so as to enable easy insertion and extraction of the catheter. In a set of embodiments, the inlet protector permits folding so as to wrap around the exterior surface of the urine conduit. In a set of embodiments, the inlet protector permits folding into a substantially tube-shaped configuration wrapping around the urine conduit. The inlet protector may be arranged to fold into the substantially tube-shaped configuration wrapping around the urine conduit in a direction towards the urine outlet during insertion of the catheter into a urethra, and to fold into the substantially tube-shaped configuration wrapping around the urine conduit in a direction towards the first urine inlet during removal of the catheter through the urethra.

In a set of embodiments, the inlet protector is arranged, in use, to permit folding into a substantially truncated-cone-shaped configuration located at least partially in a urethral opening of a bladder, with the base of the truncated-cone shape facing towards the bladder. This may enable the inlet protector to conform to the shape of the urethral neck and thus allow the catheter to sit comfortably within the urethral opening, with the first urine inlet located close to the urethral opening as possible without being obstructed by it, or by the inlet protector.

In a set of embodiments, the inlet protector, e.g. skirt, may comprise one or more holes therethrough. In some embodiments, at least one such hole is located such that when the inlet protector is folded against the urine inlet, the hole overlaps at least partially with the urine inlet. This provides a safety feature in use, so that the urine inlet is not fully obstructed by such folding of the inlet protector. If such folding does occur, urine can still pass through the hole (and thus across the inlet protector) and into the urine inlet, thereby permitting emptying of the bladder. In some embodiments a plurality of such holes is provided. Multiple holes provide redundancy (in case one gets blocked) as well as allowing the required or desired area of the holes to be distributed better across the inlet protector. The (or each) hole may have a diameter of no more than 0.5 mm, optionally no more than 0.4 mm. Such holes are small enough that they do not introduce any significant leakage across the inlet protector, but they can still allow urine to pass through the inlet protector when a pressure difference is applied across it. Where multiple urine inlets are provided, it may be desirable to provide holes in the inlet protector adjacent to each urine inlet (i.e. such that each urine inlet remains unblocked in the event of folding). This functionality may be combined with the functionality described above in which a ridge is arranged adjacent to the urine inlet to prevent blockage of the urine inlet. The combination of a ridge and hole further improves safety.

In a set of embodiments, the inlet protector, e.g. skirt, reduces in thickness between its radially inner edge and its radially outer edge. The reduction in thickness may be effected by a smooth taper or a stepped taper. In the case of a smooth taper, the thickness may taper between an inner radius and an outer radius. In some examples the inner radius may be the inlet protector's radially inner edge. In some embodiments the outer radius may be the inlet protector's radially outer edge. In other embodiments the smooth tapered section may extend across only a part (e.g. a middle part) of the inlet protector. In the case of a stepped taper, the inlet protector may include one or more step reductions in thickness. These step reductions may each be at a given radius (although in other examples they need not necessarily be symmetrical). A stepped taper may be easier to manufacture. The taper (stepped or smooth) is arranged such that the inlet protector gets thinner towards its radially outer edge (i.e. it gets thinner as the radius increases). This reduces the volume of material in the outer parts of the inlet protector. The outer parts of the inlet protector experience more folding (e.g. overlapping) when the inlet protector is folded up against the urine conduit or over the urine inlet and therefore when the outer parts of the inlet protector are thinner, these folded sections have a reduced thickness. Thus, in the folded state, the catheter overall has a smaller diameter which is easier and more comfortable to insert and remove through the urethra. The thicker parts of the inlet protector at the radially inner side provide the required stiffness to ensure that the inlet protector unfolds when the catheter is deployed and resists folding up in normal use (e.g. so that the catheter is located correctly in the urethral neck). Where the inlet protector has one or more radially extending ridges as discussed above, these may have a uniform thickness (i.e. be non-tapered) so as to provide greater resilience for deploying and maintaining the inlet protector in its non-stressed configuration. However, in other examples, the (or each) radially extending ridge may also reduce in thickness between its radially inner edge and its radially outward edge, e.g. it may be tapered (smooth or stepped). The tapering of the radially extending ridges may match the tapering of the thinner material between ridges, i.e. the ridges may maintain a consistent increase in thickness relative to the thinner material between ridges.

The inlet protector may in some embodiments have a substantially circular shape, centred on the urine conduit. However, in other examples, the inlet protector is asymmetrical about the urine conduit. For example, the inlet protector may not be rotationally symmetric about the urine conduit. In some such examples, the inlet protector may fully surround the urine conduit, but is asymmetric in that it extends further in a radially outward direction on one side than the opposite side, when in its non-stressed configuration. In other examples, the inlet protector may not extend fully around the urine conduit, but instead only extends partly round the urine conduit. The inlet protector needs to have a circumferential extent sufficient to cause it to unfold into the deployed position once it is able to do so, inside the bladder. In some examples, the inlet protector extends at least 120 degrees around the circumference of the urine conduit, or at least 150 degrees or at least 180 degrees. An asymmetric shape has the advantage that the amount of material can be reduced. The inlet protector needs to have a certain minimum size on the side of the inlet that it is to protect. However, the opposite side will often not have an inlet that requires protection. Therefore, material can be minimised by reducing the size of the inlet protector on that opposite side. A reduction in material means that when folded against the urine conduit (either over the urine inlet or not), the inlet protector takes up less space and thus contributes less to the overall diameter of the catheter. The maximum diameter of the catheter defines its size rating and thus reducing this diameter allows the catheter to be used in more situations (which may have size limits) as well as being more comfortable for a user.

In some embodiments the inlet protector may have a lobed structure, having a radius that varies with angle around the urine conduit, the inlet protector having at least one minimum radius located between two maximum radii. The minimum radius allows a reduction in material of the inlet protector and also encourages folding of the inlet protector in a particular region when the inlet protector is folded against the urine conduit. By encouraging folding to occur in one or more particular regions, the inlet protector can ensure a good distribution of material around the urine conduit, thus minimising the overall diameter of the catheter during insertion and removal. At least one of the regions of maximum radius may be aligned with the urine inlet so as to provide best protection of the urine inlet during insertion and/or removal and best protection of tissue from the bladder to be sucked into the urine inlet when the catheter is in use.

Where more than one inlet protector is provided for protecting a second urine inlet as discussed below which is positioned further away from the urine outlet than the first urine inlet, each inlet protector may be arranged for optimal protection of its respective urine inlet. As the two urine inlets may be positioned so as to face in different directions (e.g. on opposite sides of the urine conduit), asymmetrical inlet protectors for the two different urine inlets will also be preferably arranged with their maximum radius facing in different directions. This also helps to distribute material around the urine conduit.

During the process of evacuating urine from the bladder, a high flow rate can in some circumstances cause a high suction force through the urine inlet which can in some cases be sufficient to draw the inlet protector against or even into the urine inlet. As discussed above, providing a radially extending ridge on the inlet protector adjacent to the urine inlet may help to ensure that inlet protector does not get sucked in and the urine inlet is not completely blocked. However, in case of a very high suction force, with a large enough urine inlet, even a ridge may get sucked in to the point of blocking the urine inlet. To prevent this from occurring, in a set of embodiments, the shape of the urine inlet includes a blocking structure to block entry of the inlet protector (and particularly a radial ridge of the inlet protector) from entering the urine inlet. In some embodiments, the blocking structure comprises a bar extending across the urine inlet. The bar essentially divides the urine inlet into two adjacent urine inlets of smaller size, both of which are covered by the same inlet protector. In some embodiments, the bar extends across the urine inlet at an angle that is not parallel to the radially extending ridge that folds over the urine inlet. In some embodiments the bar extends substantially perpendicular to the radially extending ridge so that they form a cross when they meet. This provides a reliable way to prevent the ridge from being sucked into the urine inlet.

As noted above, the inlet protector may be integrally moulded with the urine conduit. However, in some embodiments the inlet protector may be formed on a separate inlet protector part that is attached to the urine conduit. This may be particularly convenient for adapting existing manufacturing processes. For example, a common manufacturing process is to attach a soft tip (proximal end) to a separate conduit of stiffer material (e.g. PVC). The soft tip allows for comfortable insertion while the stiffer conduit allows for easier handling (if the conduit is too floppy then the catheter is difficult to insert). Such processes typically involve attaching the tip to the conduit using adhesive or a heating process that melts the two parts together. It is then usually necessary to form the urine inlet afterwards, e.g. by punching a hole (or holes) in the side of the conduit beneath the tip. When the inlet protector is formed on a separate inlet protector part, it can be added to the catheter after the tip and conduit have been bonded and after the urine inlet has been formed. The inlet protector part can be pushed over the tip and/or conduit into the required position, e.g. adjacent to the urine inlet. The frictional forces acting on the inlet protector during the insertion/removal process are not high. Therefore a press-fit arrangement may be sufficient such that there is no need for adaptation of the existing catheter parts and low risk of the inlet protector part separating from the catheter in use. However, in some embodiments the inlet protector part may be attached or mounted to the conduit such that its axial position is fixed by something other than friction. The inlet protector part may be fixed to the conduit by adhesive or by some adhering process (e.g. heat). However, such processes add complexity and time to the manufacturing. Therefore in some embodiments the inlet protector part is attached to the urine conduit by an interlocking arrangement. The interlocking arrangement may comprise a male or female interlocking structure on the conduit and a corresponding female or male interlocking structure on the inlet protector part. For example, a recess on the conduit may engage with a corresponding projection on the inlet protector part. Likewise, a projection on the conduit may engage with a corresponding recess on the inlet protector part. In either case, more than one such recess and projection may be used if desired. A projection on the conduit may be formed as an annular rib, surrounding the conduit. A recess on the conduit may be formed as an annular groove, surrounding the conduit. An annular groove is particularly convenient as it can be formed by a material removal process on existing conduit designs (or by a mould insert) and when the inlet protector part is formed as a ring to be pushed over the conduit, its inner diameter can already form an appropriate male interlocking structure. In some embodiments the inlet protector part may have an inner ring structure of a higher rigidity than the inlet protector for improved engagement with the urine conduit.

In some embodiments the inlet protector may be integrally formed with a tip part of the catheter. The tip part may be attachable to an outlet tube to form the urine conduit. The first urine inlet may be integrally formed in the tip part such that when the tip part is attached to the outlet tube, the first urine inlet is in fluid communication with the urine outlet. Forming the inlet protector integrally with a tip part means that there is only one part to attach to the outlet tube to form the urine conduit during assembly. When the first urine inlet is also integrally formed in the tip part, there may be no need for a subsequent process (such as punching) to create the first urine inlet. The tip part may be moulded as a single piece, including the inlet protector and the first urine inlet. Moulding the first urine inlet allows the edges of the inlet to be formed much more smoothly than with a punching process. The smoother edges are much less likely to cause damage or irritation during the insertion/removal process. Nevertheless, covering the first urine inlet with the inlet protector during at least one of the insertion process and the removal process can still be beneficial. When integrally formed in the tip part, the edges of the first urine inlet may be formed with a radius that reduces the damage and/or irritation. In some embodiments the radius is at least 0.3 mm, at least 0.4 mm, at least 0.5 mm or at least 0.6 mm.

A further benefit of integrally forming the inlet protector and the first urine inlet in the tip part is that the relative positioning of the inlet protector and the first urine inlet can be very well controlled, thus ensuring a good and reliable evacuation of the bladder when the inlet protector locates in the urethral neck. Additionally, the inlet protector can be located to ensure good (e.g. complete) protection of the first urine inlet when folded over it.

As noted above, certain existing designs affix a tip part to a conduit part using a heating process that melts the two parts together. Such processes are not always suitable for allowing fluid communication from the tip to the conduit as the melting process can cause any such fluid pathway to close up. Thus, the integral tip part described above is preferably affixed to the outlet tube in a manner such that it forms (and retains) a fluid communication between the urine inlet and the urine outlet. In some embodiments the tip part may be adhered to the outlet tube with an adhesive. However, for easier manufacturing, in some embodiments the tip part is mounted to the outlet tube with an interference fit. In other words, the tip part is press-fitted to the outlet tube. The tip part may thus be engaged with the outlet tube only by the interference (e.g. the friction) between the two parts. To increase the strength of the engagement, one or more projections may be formed on at least one of the parts (i.e. on the tip part and/or the outlet tube) arranged to project towards and into the other part when engaged. The one or more projections may be one or more annular (or substantially annular) ribs. The one or more projections may include a thread. Either part may be on the inside when engaged, i.e. the tip part may be pressed inside the outlet tube or the outlet tube may be pressed inside the tip part, so long as a fluid communication is maintained when the two parts are engaged.

As the tip part is formed from a soft material for comfortable insertion of the catheter and to avoid damages to the bladder wall, if the tip comes into contact with the bladder wall, while the catheter is located in the bladder, it may be desirable to increase the rigidity of the tip part in the region of engagement with the outlet tube for an improved and easier connection. This may readily be achieved in the tip part by using an overmoulding or bi-injection moulding technique. A rigid connection piece may be provided in the engagement region of the tip part, formed from a first material of a first hardness, and the remainder of the tip part may be formed over/around the rigid connection piece from a second material of a second hardness which is lower than the first hardness. By way of example, the rigid connection piece may be formed from a plastic or from a metal. In either case, the first material is preferably biocompatible, even if it is completely covered by the second material. The rigid connection piece may be formed as a tube such that it forms (and maintains) a fluid pathway therethrough from the first urine inlet to the outlet tube when the two parts are engaged.

In addition, or as an alternative, to increase the rigidity of the tip part in the region of engagement with the outlet tube, the stiffness of the material used for the whole tip part may be increased. To reduce the effect of the increased stiffness of the material, the tip part may be made hollow along a substantial part of its length (e.g. at least 50 percent, or at least 60 percent or at least 70 percent of its length). Accordingly, in some embodiments the tip part may comprise an inner lumen extending along at least 50, at least 60 or at least 70 percent of its length. As the amount of material is reduced, the tip part becomes less stiff, thus compensating for any increase in stiffness of the material and thereby ensuring that the tip part remains soft and compliant such that it does not cause damage or discomfort when contacting the bladder wall. The hollow interior has benefits other than reducing stiffness and therefore a hollow interior may be provided regardless of the stiffness of the tip part material. For example, a longer hollow interior allows more small urine inlets to connect to a common drainage channel which connect to the outlet tube and thus the urine outlet and help with draining the bladder. Thus, in some embodiments, the tip part comprises several small urine inlets, e.g. up to 100 small urine inlets, such as up to 80, 70, 60, 50, 40, 30, 20 or up to 10 small urine inlets. Such small urine inlets are typically formed with a diameter that is smaller than the first urine inlet (and the second urine inlet discussed below) and they need not be circular. By way of example, such small urine inlets may be formed with a largest dimension less than 1 mm, less than 0.7 mm or less than 0.5 mm. Such small urine inlets may be formed with an area less than 1 mm 2, less than 0.5 mm 2, or less than 0.2 mm 2. Such small urine inlets are small enough that they have minimal risk of causing damage to the tissue during insertion and do not result in tissue being sucked into them when draining urine from the bladder. Such small urine inlets may be too small to allow draining of debris (a problem with a subset of patients), but such debris can still be drained via the larger first urine inlet (and second urine inlet if present).

The inlet protector may be formed in other ways. For example, the inlet protector may comprise or consist of one or more straps or braces that extend outwardly from the urine conduit. The straps or braces may be arranged to collapse or fold inwards for insertion and removal of the catheter and may be pulled outwards after insertion of the catheter.

In some embodiments, webbing extends between the straps or braces so as to form a skirt around the urine conduit.

In some embodiments the inlet protector may be an expandable structure which can be adjusted between a first configuration in which the inlet protector is foldable against the urine conduit and a second configuration in which the inlet protector projects away from the urine conduit. The expandable structure may be formed from an expandable chamber. Such an expandable inlet protector can be folded thin and close against the urine conduit for insertion and extraction and can be expanded to become a fairly rigid structure when in use in the bladder. This provides excellent resistance against removal (i.e. it acts as a first positioning structure) and also provides good protection for the urine inlet by separating the urine inlet from the bladder wall. The expandable structure may be an expandable skirt, which is formed from an expandable skirt chamber. The inlet protector may be expanded by means of its own conduit (i.e. so that it can be expanded separately from other structures such as a balloon as discussed herein). However, in some embodiments the inlet protector may be expanded via the same conduit that supplies a balloon (or other anti-removal structure as discussed herein). This saves space in the catheter as no additional lumens are required. Since each lumen takes up space in the catheter it reduces the potential urine flow rate. As it is desirable to maintain a high flow rate for flushing, it is beneficial to reduce the number of lumens in the catheter.

In some embodiments, the inlet protector comprises one or more straps or braces and may further comprise a balloon with the straps or braces attached to it, or passing over it. The balloon may be intended to be inflated inside the bladder, and expansion of the balloon may pull the straps or braces away from the urine conduit. In this position, the inlet protector protects the urine inlet by ensuring that the bladder wall does not come into contact with the urine inlet.

Straps may also be attached to the inlet protector (as opposed to being attached to the urine conduit). In such embodiments, the straps can be arranged to pull the inlet protector into a deployed (and protecting) position. This can be useful to ensure that the inlet protector takes the appropriate form once the catheter is installed in a patient. For example, in some embodiments, as discussed elsewhere in this document, the inlet protector may fold towards the urine outlet during the insertion of the catheter into a patient. To function optimally, the inlet protector needs to be moved away from that folded configuration and into a configuration in which it lies between the urine inlet and the bladder wall. Thus, straps may be used to pull the inlet protector into such suitable configuration. As above, such straps may be pulled by some actuating device, such as inflation of a balloon, after insertion of the catheter. The balloon may serve other functions as discussed elsewhere.

In other embodiments, the straps or braces described above are not comprised in the inlet protector but are an additional feature of the claimed catheter which may provide a supporting structure which is used together with the inlet protector, which may be in any of the forms discussed above (e.g. a skirt extending outwardly from the urine conduit). If the inlet protector is mounted closer to the urine outlet than the straps or braces (but adjacent thereto), the straps or braces then limit movement of the inlet protector towards the urine inlet. Thus the urine inlet will not be fully closed off by the inlet protector.

The straps or braces also provide a positioning structure which can prevent the catheter from being withdrawn through the urethra (e.g. until the balloon or other support is deflated or collapsed or until the inlet protector is folded). The straps or braces may be arranged to extend from the urine conduit at an angle that approximates the angle of the urethral neck so that a comfortable fit is obtained. This angle may be varied for different patients (for example, several devices with different geometries may be manufactured so that an appropriate geometry can be selected for a given patient).

In a set of embodiments, the urine conduit further comprises a second urine inlet positioned further away from the urine outlet than the first urine inlet. In other words, the second urine inlet may be positioned at a more proximal location along the urine conduit than the first urine inlet. In such embodiments the second urine inlet may thus be positioned further away from the urethral neck when the catheter is installed in a user than the first urine inlet. The second urine inlet may be located at or near to a proximal end of the urine conduit. The inclusion of such a second urine inlet may advantageously provide a backup urine inlet which may ensure that evacuation of the bladder is still possible in the event that the first urine inlet is obstructed by the inlet protector and/or the urethral neck e.g. as a result of the catheter being pulled in a distal direction (away from the body) through the urethra.

In a set of embodiments, the second urine inlet is located in a side wall of the urine conduit. The second urine inlet may comprise a hole formed in a side wall of the urine conduit. The second urine inlet may comprise a plurality of holes formed in the side wall of the urine conduit. The plurality of holes may be located at substantially the same longitudinal position along the urine conduit. In other words, the plurality of holes may be located around the cross-sectional perimeter of the urine conduit at substantially the same location along the length thereof.

When a second urine inlet is provided at a different axial location than the first urine inlet, it provides a backup inlet in the event that the lower (more distal) inlet gets blocked or lodged in the urethra. With two such urine inlets, an inlet protector may be provided for both urine inlets or multiple inlet protectors may be provided so that both urine inlets are protected during at least one of the insertion process and the removal process. In some embodiments, at least one inlet protector is located between the first urine inlet and the second urine inlet and is arranged to fold over one urine inlet during insertion and is arranged to fold over the other urine inlet during removal. This inlet protector may be the same inlet protector as has been discussed above (with the second urine inlet then located more distal than the first urine inlet). In other embodiments where the second urine inlet is located more proximal than the first urine inlet, this inlet protector may be in addition to an inlet protector between the first urine inlet and the urine outlet. In other implementations (discussed below), there may be no inlet protector between the first urine inlet and the urine outlet, e.g. there may only be an inlet protector between the first urine inlet and the second urine inlet (the intermediate inlet protector). It will be appreciated that the axial distance between the urine inlets and the size of the inlet protector will affect the degree of overlap that is possible, but in some embodiments they are arranged to permit full overlap of the respective inlet during respective insertion and removal. It will be appreciated that this intermediate protector may be the only inlet protector. However, where two inlet protectors are provided, both the first and second urine inlets may be protected during either insertion or removal. For example, with a first urine inlet located between a first inlet protector and a second inlet protector (the intermediate inlet protector), and with the second urine inlet located nearer the tip than the second inlet protector, both urine inlets are protected during the removal process. On the other hand, with a first inlet protector (the intermediate inlet protector) located between the first urine inlet and the second urine inlet and a second inlet protector located nearer the tip than the second urine inlet, both urine inlets are protected during the insertion process (provided that the distances between urine inlets and the size of the inlet protectors allow for appropriate folding over the respective urine inlet). In some embodiments three inlet protectors may be provided with two urine inlets such that both urine inlets are protected during both the insertion and removal processes. For example, with a first urine inlet located between a first inlet protector and a second inlet protector (the intermediate inlet protector) and a second urine inlet located between the second inlet protector and a third inlet protector, both urine inlets can be protected during both insertion and removal of the catheter. In particular, during insertion, the first urine inlet is protected by the second inlet protector and the second urine inlet is protected by the third inlet protector. During removal, the first urine inlet is protected by the first inlet protector and the second urine inlet is protected by the second inlet protector. It will be appreciated that this arrangement may readily be extended to protect more than two urine inlets at different axial positions.

In other embodiments, an additional opening is provided for instruments (e.g. with its own separate lumen traversing the length of the catheter). In another set of embodiments the second urine inlet or an additional opening is located on the tip of the catheter (e.g. on the rounded end). The second urine inlet or additional opening may be substantially on the longitudinal axis of the catheter. Such an inlet or opening is more likely to remain open for urine flow if the catheter is pulled down into the urethra. In some embodiments, the second urine inlet (whether on the tip or on the side) may additionally function to allow insertion of instruments into the bladder.

In a set of embodiments, the catheter further comprises an anti-removal structure (which may act as a second positioning structure) located between the first urine inlet and the second urine inlet. In a set of embodiments, the anti-removal structure is adjustable from a first configuration in which the anti-removal structure permits removal of the catheter through the urethra, and a second configuration where the anti-removal structure prevents removal of the catheter through the urethra. The anti-removal structure may permit insertion of the catheter through the urethra when in the first configuration. The anti-removal structure may have a cross-sectional area that is larger than the cross-sectional area of the urethral neck when in the second configuration. The presence of such an anti-removal structure may advantageously ensure that the catheter does not exit the bladder when the catheter is pulled in a distal direction through the urethra with sufficient force that the inlet protector folds and thus moves into the urethra.

The anti-removal structure may be located close to the inlet protector such that when the anti-removal structure contacts the urethral neck, when in the second configuration, the inlet protector is arranged to push against the neck so as to cause the catheter to move back in the direction towards the bladder. The anti-removal structure may be located substantially adjacent to the first urine inlet.

In a set of embodiments, the longitudinal separation between the anti-removal structure when in the second configuration and the inlet protector when in its non-stressed position is less than the maximum lateral separation between an edge of the inlet protector and an exterior surface of the urine conduit. In such embodiments, if the inlet protector is caused to fold or contract towards the anti-removal structure, the inlet protector will overlap the anti-removal structure which may advantageously prevent the inlet protector form blocking the urine inlet. A larger inlet protector may also allow a better seal against the bladder wall so as to minimise leakage.

In other embodiments the longitudinal separation between the anti-removal structure when in the second configuration and the inlet protector when in a non-stressed position is greater than or equal to the maximum lateral separation between an edge of the inlet protector and an exterior surface of the urine conduit. This allows the inlet protector to fold up against the urine conduit without interfering with the anti-removal structure so as to keep the overall diameter of the catheter small for insertion. By way of example, the separation may be less than a distance that is 100% greater than, preferably 50% greater than, preferably 30%, preferably 20% greater than, preferably 10% greater than, the maximum lateral separation between an edge of the inlet protector and an exterior surface of the urine conduit. In other words, the longitudinal separation (along the axis of the catheter) may be less than twice the width of the inlet protector, where the width of the inlet protector is the distance from the urine conduit's outer radius to the inlet protector's outer radius. Such separations may advantageously ensure that the urine conduit is prevented from moving far enough into the urethra to cause the inlet protector to fully enter the urethra and thus prevent the resiliency of the inlet protector from moving the catheter back towards the bladder.

In some embodiments, the surface of the inlet protector facing towards the first urine inlet may comprise ridges which protrude outwardly so as to maintain a flow path to allow urine to enter the first urine inlet when the inlet protector is folded up against the anti-removal structure or against the urine conduit.

In a set of embodiments, the anti-removal structure comprises a positioning balloon. The positioning balloon may be attached to the exterior surface of the urine conduit. The positioning balloon provides an expandable chamber. The positioning balloon may be adjustable between a contracted configuration in which the positioning balloon permits removal of the catheter through the urethra, and an expanded configuration in which the positioning balloon prevents removal of the catheter through the urethra.

In a set of embodiments, when viewed along a longitudinal axis of the urine conduit, the positioning balloon has a larger cross-sectional area than the urethral neck when in the expanded configuration. When in the contracted configuration, the positioning balloon may have cross-sectional area small enough that it can easily be pulled through the urethra. In the contracted configuration, the cross-sectional area may be smaller than the urethral neck. The positioning balloon may be adjustable from the contracted configuration to the expanded configuration through insertion of fluid into the expandable chamber, and adjustable from the expanded configuration to the contracted configuration through removal of fluid from the expandable chamber. The fluid may be any suitable fluid, e.g. air, water, saline solution, or any another biocompatible or non-toxic fluid in order to avoid harm in case of leakage.

In a set of embodiments, the catheter comprises a fluid supply conduit through which fluid may be inserted and/or removed from the positioning balloon. The fluid supply conduit may be coupled to the positioning balloon in order to allow fluid communication therebetween. The fluid supply conduit may be integrally moulded with the urine conduit. The fluid supply conduit may be formed in a side wall of the urine conduit and extend parallel thereto along a majority of the length of the urine conduit. The fluid supply conduit may comprise an opening arranged to be located outside of the body when the catheter is installed in a user. The fluid supply conduit may protrude outwardly from the wall of the urine conduit at a distal end of the catheter to form a distinct opening thereof. The opening of the fluid supply conduit may comprise a valve. A pump may be removably attachable to the opening of the fluid supply conduit for forcing fluid therethrough into the positioning balloon. Such a pump may comprise e.g. a syringe. The valve may be operable to prevent fluid from passing through the opening of the fluid supply conduit in a first configuration, and to allow fluid to pass through the opening of the fluid supply conduit when in a second configuration.

In a set of embodiments the catheter may further comprise at least one strap or at least one brace extending over the positioning balloon. In the following, the terms "straps" and "braces" are used for ease, and are intended to denote one or a plurality of straps and one or a plurality of braces respectively. The straps/braces may help to hold the shape of the positioning balloon in a stable and preferred form. An advantage of this is that less fluid pressure is required to provide that form. If a lower fluid pressure is used without straps/braces then the balloon may deform too much away from the desired shape (which may for example result in it receding too far into the urethral neck), but a higher fluid pressure requires a stiffer balloon and results in a stiffer and less comfortable balloon. The straps/braces can hold the balloon in the preferred form while allowing it to be softer and more malleable while still performing its desired function. The straps/braces can provide additional functionality as follows.

In some embodiments the straps/braces provide the inlet protector, i.e. are comprised in or are the inlet protector, and as the positioning balloon expands, the straps/braces which are attached to the urine conduit below the fluid inlet will project outwards from the urine conduit. This reduces the number of parts required. The straps/braces may be aligned with the first urine inlet so that when the balloon is deflated, the straps/braces cover the first urine inlet, thereby protecting it from tissue contact. When the straps/braces are in the deployed configuration, the first urine inlet is open for urine flow and it is separated from the bladder wall, thereby protecting it from blockage or fouling.

Where a plurality of straps or braces are provided (e.g. distributed around the circumference of the urine conduit), webbing may be provided between the straps/braces to provide an inlet protector that surrounds the urine conduit, thereby improving the protection of the urine inlet and providing some of the functionality of a skirt as discussed above. In some embodiments, at least three straps or braces or at least four straps or braces are provided.

In some embodiments the straps/braces attach to the urine conduit at an upper attachment point near the proximal end of the catheter. Such arrangements can provide similar functionality to the lower attachment point below the first urine inlet, as discussed above, but for a second urine inlet near the tip of the catheter as discussed herein. Accordingly, the urine conduit may comprise a second urine inlet (e.g. the same second urine inlet referred to previously herein) between the upper attachment point and the positioning balloon. Existing catheters which have a single inlet at the tip can suffer from problems where the inlet can become blocked or fouled by tissue contact with the bladder wall. Providing straps/braces which extend from a positioning balloon over the second urine inlet to an upper attachment point above the second urine inlet protects the second urine inlet from tissue contact and fouling. It may also have an additional benefit of making the tip of the catheter less pointy, thereby making it less likely to damage the bladder wall as well as less likely to stick to it.

It will be appreciated that straps/braces (whether for attachment near the tip end of the catheter or for attachment below the first urine inlet) may be attached to the balloon so that the balloon pulls the straps/braces outwardly as it expands. The straps or braces may be made from an elastic material so that they stretch as the balloon expands. In other embodiments, the straps/braces may be attached at both a lower attachment point (between the first urine inlet and the urine outlet) and an upper attachment point (near the proximal end of the catheter). In such embodiments, the straps/ braces need not be affixed to the balloon, but may rather simply pass over it such that expansion of the balloon stretches the straps/braces radially outwardly away from the urine conduit. Such straps/braces can provide both of the benefits discussed above, e.g. protecting both a first urine inlet and a second urine inlet.

In a set of embodiments, the catheter comprises a fluid-based actuator comprising an expandable chamber, the fluid-based actuator being adjustable between a contracted configuration in which the expandable chamber contains a first volume of fluid and an expanded configuration in which the expandable chamber contains a second volume of fluid, the second volume being greater than the first volume;

wherein:

when the fluid-based actuator is in one of the contracted and the expanded configurations, urine is able to flow from the first urine inlet to the urine outlet; and when the fluid-based actuator is in the other of the contracted and the expanded configurations, urine is prevented from flowing from the first urine inlet to the urine outlet. Such embodiments may advantageously provide a mechanism by which flow of urine through the urine conduit may be controlled by a user.

When the fluid-based actuator is in said one of the contracted and the expanded configurations, urine may also be able to flow from the second urine inlet to the urine outlet, and when the fluid-based actuator is in said other of the contracted and the expanded configurations, urine may be prevented from flowing from the second urine inlet to the urine outlet. Thus, the fluid-based actuator may be used to controllably prevent all urine flow from the bladder through the urine conduit irrespective of which urine inlet it enters.

In some embodiments, such catheters with a fluid-based actuator are for treating urinary incontinence as the fluid-based actuator provides a mechanism to stop (and to control) the urination process.

In a set of embodiments, the catheter comprises an actuation conduit through which fluid may be forced into the expandable chamber of the fluid-based actuator, and an actuation conduit through which fluid may be removed from the chamber of the fluid-based actuator. In a set of embodiments, the actuation conduit through which fluid may be forced into the chamber and the actuation conduit through which fluid may be removed from the chamber are the same actuation conduit—i.e. in such embodiments, the catheter comprises an actuation conduit through which fluid may be forced into the chamber and through which fluid may be removed from the chamber. Such embodiments may advantageously reduce the number of parts required for the catheter. It will be appreciated that other embodiments may use separate conduits for supply and removal of fluid.

In a set of embodiments, the actuation conduit may have a first opening operably coupled to a fluid inlet of the fluid-based actuator, and a second opening arranged to be located outside the body when the catheter is installed in a user. The first opening may be located at or near to a first end of the actuation conduit, and the second opening may be located at or near to a second end of the actuation conduit. This enables the actuation conduit to be accessed by the user when the catheter is installed in the body and thus allows control of the fluid-based actuator by a user from outside of the body.

In a set of embodiments, the actuation conduit extends through the urine conduit to a location outside the body when the catheter is installed in a user. Although it is normally desirable not to obstruct the urethra (so as to allow near normal urination flow rate), a small enough conduit will not compromise flow too much.

In a set of embodiments, the actuation conduit extends through the urine conduit. The actuation conduit may be located in the flow path between the first urine inlet and the urine outlet. This provides a relatively straightforward arrangement and thus reduces overall manufacturing complexity (and therefore cost).

In a set of embodiments, the catheter comprises a valve for preventing fluid from exiting the expandable chamber of the fluid-based actuator. The valve may be a manually operable valve. The valve may be located at or towards the second end of the actuation conduit and may thus be located outside of the body when the catheter is installed in a user. The actuation conduit may comprise the valve or the valve may be attached to the actuation conduit. The inclusion of a valve enables the fluid-based actuator to be maintained in the expanded configuration until it is desired to change it to the contracted configuration. The valve may be releasable by the user so as to allow the user to easily commence urination. In a set of embodiments, the valve can be operated between a first configuration and a second configuration. In the first configuration fluid is prevented from passing through the actuation conduit from the expandable chamber of the fluid-based actuator to the second opening of the actuation conduit. In the second configuration fluid is able to pass through the actuation conduit from the expandable chamber of the fluid-based actuator to the second opening of the actuation conduit.

The catheter may further comprise a pump for forcing liquid through the actuation conduit into the fluid-based actuator. The pump may be located outside the body when the catheter is installed in a user. The pump may comprise the valve. In a set of embodiments, the pump is releasably attachable to the second end of the actuation conduit. Such embodiments may advantageously enable the pump to be detached from the actuation conduit when not in use. Detaching the pump may be convenient and it may reduce potential discomfort for the user. The pump may be stored remotely from the actuation conduit and not permanently attached to it. In other embodiments, the pump may be permanently attached to the second end of the actuation conduit. The pump may be integrally moulded with the actuation conduit. Such embodiments may advantageously improve sealing between the pump and the actuation conduit, thus preventing fluid from leaking out of the actuation conduit and/or the pump. In a set of embodiments, the pump is manually operable.

The pump may be a positive displacement pump. The pump may be a peristaltic pump. Such pumps can be operated manually without requiring a power source. They may also function as the valve by preventing movement of fluid in both directions unless such movement is caused by the pump.

The pump, the actuation conduit and the fluid-based actuator may form a sealed system. A sealed system does not require topping up of fluid and instead simply moves fluid from one location to another. For example, in a sealed system, the fluid may be moved between the expandable chamber and a storage reservoir. The pump may be located between the expandable chamber and the storage reservoir.

In a set of embodiments, the pump comprises a squeeze pump. The squeeze pump may be relatively small—e.g. operable using a single hand, operable using a thumb and a finger on the same hand, etc. The squeeze pump may be integrally moulded with the actuation conduit which simplifies manufacture and reduces cost.

In a set of embodiments, the pump is arranged to force enough fluid into the fluid-based actuator to change it from the contracted configuration to the expanded configuration with a single actuation thereof. Such embodiments may improve usability of the catheter, since a user can quickly and conveniently commence urination at a maximum flow rate with a single actuation. In some embodiments a single actuation of the pump in the opposite direction is also sufficient to change the expandable chamber to the fully contracted configuration. Such embodiments may provide a convenient feedback mechanism for the user, allowing them to determine the configuration of the fluid-based actuator based on the configuration of the pump, which they can see and/or feel.

It will be appreciated that in other embodiments the expandable chamber may collapse to the contracted state without actuation of the pump (e.g. by opening a valve).

In a set of embodiments, the pump comprises a syringe. The syringe may be attachable to (e.g. insertable into or onto) the second end of the actuation conduit. The valve may be operable through insertion and removal of the syringe. The valve may be arranged to allow fluid to pass therethrough when the syringe is inserted into the actuation conduit, and it may be arranged to prevent fluid from passing therethrough when the syringe is removed from the actuation conduit. Such embodiments may provide a convenient mechanism for forcing fluid into and removing fluid from the fluid-based actuator.

In a set of embodiments, the fluid-based actuator comprises an actuation balloon. The actuation balloon may be made of an elastic material, e.g. silicone. In a set of embodiments, the actuation balloon is located in the flow path between the first urine inlet and the urine outlet.

In a set of embodiments, the actuation balloon is arranged to abut the first urine inlet when in the expanded configuration thereby blocking or closing off the first urine inlet and preventing urine from entering the urine conduit therethrough. The actuation balloon may be configured to contract away from the first urine inlet when in the contracted configuration thereby allowing urine to enter the urine conduit through the first urine inlet. Such embodiments may advantageously ensure that urine is not allowed to enter the urine conduit through the first urine inlet when the actuation balloon is in the expanded configuration, thereby preventing urine from being held or stored within the urine conduit. Stored urine can crystallise and leave residue which can result in damage to the internals of the catheter and can present a health hazard to the user.

In a set of embodiments, the first urine inlet comprises one or more holes formed in a side wall of the urine conduit, and the actuation balloon is arranged to abut a peripheral wall of each of said holes when in the expanded configuration thereby preventing urine from entering the urine conduit therethrough. The actuation balloon may be arranged to protrude into each hole when in the expanded configuration so as to form a seal with the peripheral wall of each hole. Such embodiments may advantageously improve sealing between the actuation balloon and the first urine inlet and thus prevent leakage of urine through the catheter.

In a set of embodiments, the actuation balloon is arranged to abut an internal wall of the urine conduit between the first urine inlet and the urine outlet when in the expanded configuration so as to prevent urine from flowing from the first urine inlet to the urine outlet through the urine conduit. Such an arrangement may further prevent urine from flowing from the second urine inlet to the urine outlet through the urine conduit. The urine conduit may comprise a constricted portion located between the first urine inlet and the urine outlet. The actuation balloon may be arranged to abut an inner surface of the constricted portion of the urine conduit when in the expanded configuration so as to prevent urine from flowing from the first urine inlet to the urine outlet through the urine conduit. The actuation balloon may be arranged to protrude into the constricted portion of the urine conduit when in the expanded configuration so as to form a seal with the inner surface of the constricted portion.

In a set of embodiments, the actuation balloon is arranged to abut an internal wall of the urine conduit between the second urine inlet and the urine outlet when in the expanded configuration. This may form a seal between the second urine inlet and the urine outlet, and thus prevent urine from flowing through the urine conduit through the second urine inlet.

The actuation balloon may have any appropriate shape depending on the shape of the catheter, particularly the urine conduit. The actuation balloon may have a substantially spherical shape when in the expanded configuration. It may have a substantially ovoid shape when in the expanded configuration. It may have a substantially elongate shape when in the expanded configuration. It may have a substantially cylindrical shape with rounded ends when in the expanded configuration. It may have a substantially tube-like shape when in the expanded configuration. It may have a substantially toroidal shape when in the expanded configuration. The substantially toroidal shape may have a circular cross-section. In other words, if the toroidal shape is described as a tubular ring, with the major radius being the distance from the centre of the tube to the centre of the torus and the minor radius being the radius of the tube, then the tube may have a circular cross-section in a plane that includes the centre of the torus. It may instead have a substantially oval shaped cross-section. It may have a substantially pill-shaped cross-section. The actuation balloon may have an overall elongated donut-shape when in the expanded configuration.

In a set of embodiments, the actuation conduit extends at least partially through the expandable chamber of the actuation balloon. The actuation conduit may extend fully through the expandable chamber of the actuation balloon. The actuation conduit may be fixed to a proximal end of the catheter so as to provide an anchor for the actuation conduit and optionally also the actuation balloon, so as to keep the actuation balloon in place relative to the urine conduit. A surface of the actuation balloon may be fixed to a surface of the actuation conduit so as to seal the surface of the actuation balloon to the actuation conduit. The second opening of the actuation conduit may be formed in a side wall thereof and communicate directly with the expandable chamber of the actuation balloon.

In a set of embodiments, the actuation balloon has a substantially toroidal shape having a central opening extending along a longitudinal axis of the catheter. The actuation conduit may at least partially extend through the central opening, and the first opening of the actuation conduit may communicate with the expandable chamber of the actuation balloon at the central opening.

The central opening of the actuation balloon may be sized so as to accommodate insertion of instruments therethrough (e.g. pH sensors, temperature sensors, etc.). This may advantageously provide a convenient mechanism for monitoring the user and/or the catheter without requiring the catheter to be removed from the user. Where the urine conduit has a rounded proximal end, an instrument hole may be provided in the urine conduit so that instruments may be inserted into the bladder. A flow path between the instrument hole and the urine outlet may be ideally blocked or closed off by the actuation balloon when it is in its expanded configuration so as to prevent urine passing to the urine outlet through the instrument hole in normal use.

In a set of embodiments, the actuation balloon has a fluid inlet located in a side-wall of the central opening. The actuation conduit may comprise one or more fluid outlets located in the side wall thereof and operably coupled to the fluid inlet(s) of the actuation balloon. The actuation conduit may extend through the central opening and be fixed to the interior surface of a proximal end wall of the urine conduit. Such embodiments may advantageously provide a mechanism for holding the actuation balloon in place relative to the urine conduit.

In some embodiments, the catheter as disclosed herein is an intermittent catheter, i.e. a catheter that is inserted into the bladder for just long enough to drain the bladder, and removed when the flow of urine stops. Such catheter preferably does not comprise an anti-removal structure as described herein. Typically, an intermittent catheter is a single-use catheter with a single lumen to drain urine from the bladder and is disposed of after use.

In some embodiments, the catheter as disclosed herein is an indwelling catheter, i.e. a catheter that is left in place in a user for an extended time. Such catheter preferably comprises an anti-removal structure as described herein.

When viewed from a second aspect, the invention provides a catheter insertable into a urethra for installation in a user's bladder and urethra, the catheter comprising:

a urine conduit comprising a first urine inlet and a urine outlet; and a resilient skirt arranged, in use, to inhibit removal of the catheter through the urethra, the resilient skirt being positioned between the first urine inlet and the urine outlet.

It will be appreciated that the resilient skirt of the second aspect is an embodiment of the inlet protector/can provide the same functionality as the inlet protector of the first aspect. Therefore any of the preferred and optional features discussed above in relation to the inlet protector should be considered equally applicable to the resilient skirt of the second aspect. In addition, the other features (other than the resilient skirt) discussed above in relation to the first aspect, are likewise equally applicable to the catheter of the second aspect.

When viewed from a third aspect, the invention provides a catheter insertable into a urethra for installation in a user's bladder and urethra, the catheter comprising:

a urine conduit comprising a first urine inlet and a urine outlet;

a first positioning structure arranged, in use, to inhibit removal of the catheter through the urethra.

a second positioning structure adjustable from a first configuration in which it does not significantly inhibit removal of the catheter through the urethra and a second configuration in which it prevents removal of the catheter through the urethra;

wherein:

the first positioning structure is positioned between the first urine inlet and the urine outlet; and the first urine inlet is positioned between the second positioning structure and the first positioning structure.

Thus it will be seen that the catheter of the third aspect comprises two positioning structures positioned either side of the urine inlet. One of the positioning structures inhibits (but does not necessarily prevent) removal from the urethra, and the other positioning structure is adjustable between one configuration which permits removal of the catheter through the urethra and another configuration which prevents removal of the catheter through the urethra. Thus, the second positioning structure acts as a backup positioning structure in case the catheter is pulled out of the urethra with sufficient force to enable the first positioning structure to enter the urethra, thereby ensuring that the catheter cannot be removed through the urethra unless desired.

In a set of embodiments, the catheter comprises a second urine inlet, wherein the second positioning structure is positioned between the second urine inlet and the first urine inlet. This may provide a backup urine inlet in case the first urine inlet becomes blocked, e.g. in the event that the catheter is pulled with sufficient force to cause the first urine inlet to enter the urethra and thus prevent fluid communication between the first urine inlet and urine in the bladder.

It will be appreciated that the first positioning structure of the third aspect may be the inlet protector of the first aspect. The second positioning structure of the third aspect may be the anti-removal structure of the first aspect. Accordingly, any preferred or optional features discussed above in relation to the inlet protector or the anti-removal structure of the first aspect should be considered equally applicable to the first positioning structure and the second positioning structure of the third aspect. Other features of the first aspect are also equally applicable to the third aspect.

According to a fourth aspect, the invention provides a catheter insertable into a urethra for installation in a user's bladder and urethra, the catheter comprising:

a urine conduit comprising a urine inlet;

an anti-removal structure adjustable between a first configuration in which the anti-removal structure permits removal of the catheter through the urethra and a second configuration in which the anti-removal structure prevents removal of the catheter through the urethra; and at least one strap extending from the anti-removal structure to an upper attachment point on the urine conduit;

wherein the urine inlet is located between the upper attachment point and the anti-removal structure.

It will be appreciated that this fourth aspect relates to a subset of features that are discussed above in relation to the first aspect, but otherwise may generally relate to the same types of catheter. In particular, while according to the most general forms of the fourth aspect, there may be a single urine inlet located proximally of the anti-removal structure (which may correspond to the second urine inlet discussed in relation to the first aspect), there may be an additional urine inlet distal of the anti-removal structure (e.g. corresponding to the first urine inlet discussed in relation to the first aspect). In addition, the other features discussed above in relation to the first aspect (such as the inlet protector, fluid-based actuator, valve, pump, etc.) may all equally be applied to this fourth aspect.

According to a fifth aspect, the invention provides a method of making a catheter comprising assembling an inlet protector part to a urine conduit part such that the inlet protector part is located adjacent to a first urine inlet of the urine conduit part. The first urine inlet may be formed in any suitable manner (e.g. by punching) and it may be formed before or after the assembly of the inlet protector part to the urine conduit part. It will be appreciated that any of the structural features discussed above may also be features of this aspect, e.g. the assembly via male and female interlocking structures or friction fit, the structure of the inlet protector (e.g. the provision of radial ridges on the inlet protector), etc.

According to a sixth aspect, the invention provides a tip for a catheter, the tip comprising an integral inlet protector. The tip may in some embodiments further comprise an integral urine inlet. The urine inlet may be located between the inlet protector and a first end of the tip and may be arranged to provide a fluid communication channel to a second, opposite end of the tip. Again, it will be appreciated that the various structural features discussed above may equally be applied to this sixth aspect, e.g. the provision of second (or further) urine inlets, the provision of second (or further) inlet protectors, the provision of a rigid connection part, the specific structure of the (or each) inlet protector (e.g. the provision of radial ridges), etc.

According to a seventh aspect, the invention provides a method of making a tip for a catheter, comprising moulding as one piece, a tip having an inlet protector. As above, all structural features of the tip discussed above that can be moulded with the inlet protector are also optional features of the seventh aspect. For example, the urine inlet and its fluid communication channel, further urine inlets and further inlet protectors, the rigid connection part and the structure of the inlet protector(s) may all be features of the seventh aspect.

According to an eighth aspect, the invention provides a catheter insertable into a urethra for installation in a user's bladder and urethra, the catheter comprising: a urine conduit comprising a first urine inlet and a urine outlet; and an inlet protector extending outwardly from the urine conduit from a position between the first urine inlet and proximal end of the catheter. As above, the inlet protector may feature any of the optional features discussed above in relation to other inlet protectors, e.g. radial ridges, being inflatable, formed separately and mountable via friction fit or grooves, or moulded integrally with a separate tip. The inlet protector may be supplemented by other inlet protectors as discussed above for any number of urine inlets.

Generally, features of any embodiment described herein may, wherever appropriate, be applied to any other embodiment described herein. Where reference is made to different embodiments or sets of embodiments, it should be understood that these are not necessarily distinct but may overlap.

BRIEF DESCRIPTION OF THE DRAWINGS

Certain embodiments of the invention will now be described, by way of example only, and with reference to the accompanying drawings in which.

DETAILED DESCRIPTION OF THE DRAWINGS

Figure 1:
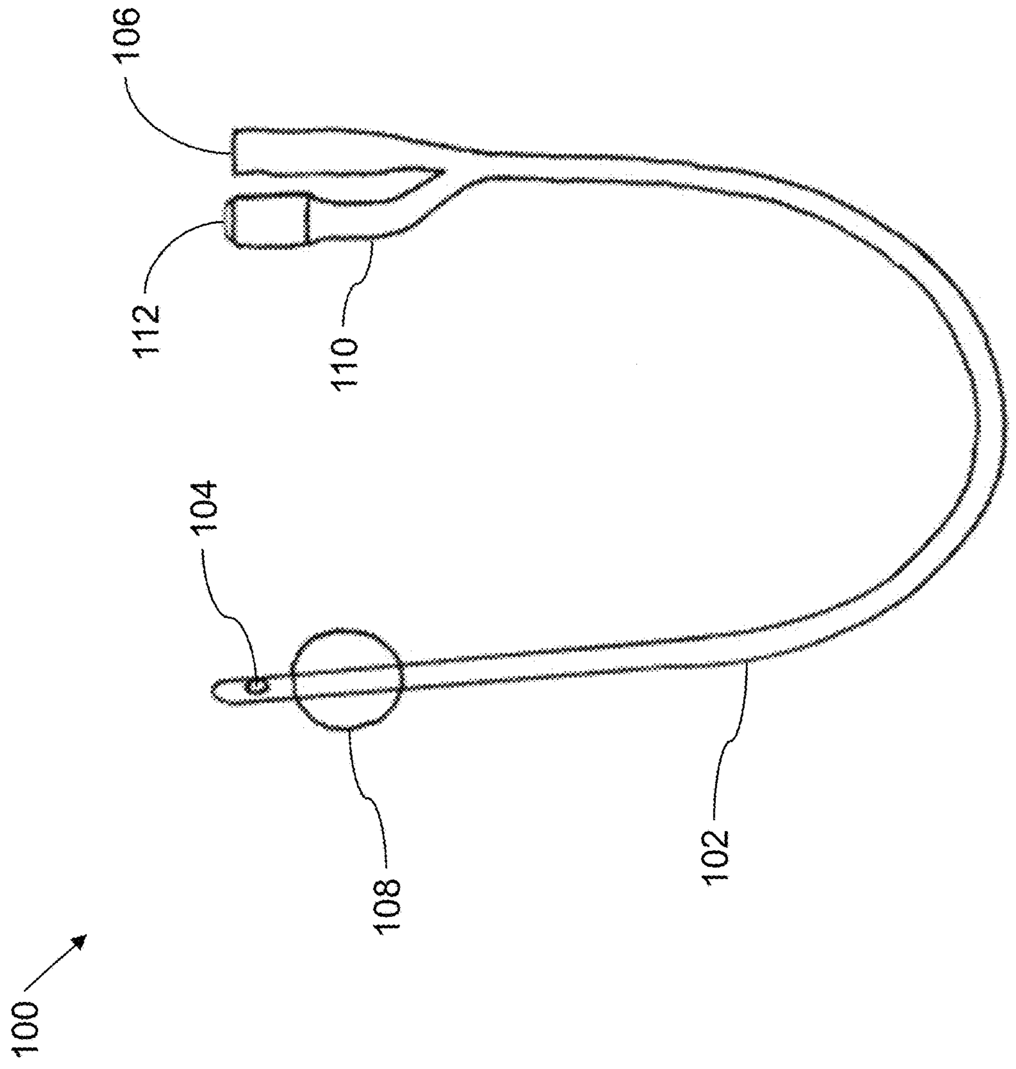
FIG. 1 (Prior art)
FIG. 1 is a schematic side view of a prior-art Foley catheter.

FIG. 1 shows a schematic side view of a prior-art Foley catheter 100. The catheter 100 comprises a urine conduit 102 having a urine inlet 104 formed in a side wall thereof close to the proximal end thereof and a urine outlet 106 located at the distal end thereof. A positioning balloon 108 is located between the urine inlet 104 and the urine outlet 106, close to the urine inlet 104. The catheter 100 further comprises a fluid supply conduit 110 having an opening 112. The fluid supply conduit 110 extends from the opening 112 into the side wall of the urine conduit 102, and extends parallel to the urine conduit 102 inside the side wall thereof. Thus the catheter 100 has two lumens extending therethrough, one for evacuating urine from the bladder and one for inflating/deflating the positioning balloon.

The catheter 100 is insertable through the urethra for positioning in the bladder of a user, with the urine conduit 102 extending through the urethra, the urine outlet 106 and opening 112 of the fluid supply conduit 110 being located outside of the body, and the positioning balloon 108 and the urine inlet 104 being positioned inside the bladder. Urine in the bladder enters the urine inlet 104 and passes through the urine conduit 102 to the urine outlet 106, thus allowing urine to be drained from the bladder.

The fluid supply conduit 110 is in fluid communication with the positioning balloon 108. The positioning balloon 108 provides an expandable chamber and is adjustable between a contracted configuration when little or no fluid is held inside the expandable chamber and an expanded configuration (the expanded configuration being shown in FIG. 1) when the expandable chamber is filled with fluid. When the positioning balloon 108 is in the contracted configuration, the catheter 100 can be inserted into and removed from a user through the urethra since it is able to pass through the urethra. When the positioning balloon 108 is in the expanded configuration, the catheter 100 is prevented from exiting the urethra since it has a larger cross-sectional area than the cross-sectional area of the urethral neck, and therefore abuts the bladder wall when the catheter 100 is pulled in a distal direction away from the body.

Fluid is inserted into and removed from the expandable chamber of the balloon 108 using the fluid supply conduit 110. The fluid supply conduit 110 comprises a valve (not shown) at the outside end thereof which is operable to allow fluid to pass therethrough only when a suitable pump (e.g. a syringe) is releasably coupled to the opening 112 of the fluid supply conduit 110. Thus, fluid can be inserted into and removed from the positioning balloon 108 by actuation of the pump. When the pump is removed, the valve prevents fluid from exiting the expandable chamber of the positioning balloon 108, causing it to maintain its current configuration. The positioning balloon 108 can therefore be maintained in the expanded configuration shown in FIG. 1 in order to keep the catheter 100 in position in a user. It can be maintained in the contracted configuration in order to allow the catheter to be inserted into and removed from the user through the urethra.

Since the positioning balloon 108 is quite large, the urine inlet 104 is located a substantial distance away from the urethral neck when the catheter 100 is installed in a user. This leads to a urine pooling problem whereby a significant volume of urine is able to pool in the bladder below the urine inlet 104 and is not able to exit the bladder via the urine conduit 102. Pooled urine can crystallise and leave residue which can result in damage to the catheter 100 and can present a health hazard (e.g. infection risk) to the user.

Figure 2:
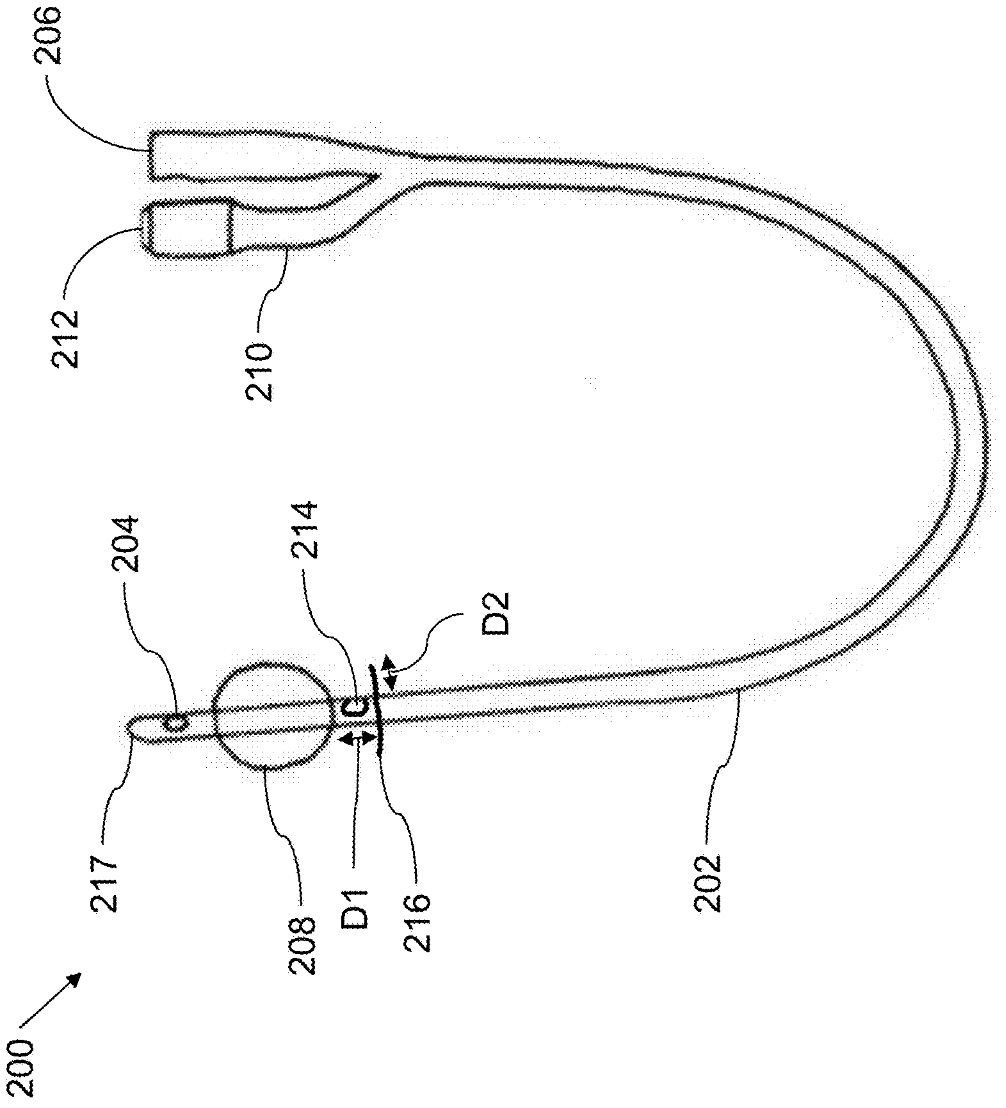
FIG. 2 is a schematic side view of a catheter in accordance with an embodiment of the invention.

FIG. 2 shows a schematic side view of a catheter 200 in accordance with an embodiment of the invention. The catheter 200 comprises a urine conduit 202 having a first urine inlet 214 formed in a side wall thereof, a urine outlet 206 at a distal end thereof, and an inlet protector in the form of a resilient skirt 216 located between the first urine inlet 214 and the urine outlet 206, close to the first urine inlet 214. The catheter 200 is insertable through the urethra for positioning in the bladder, with the urine conduit 202 extending through the urethra such that the urine outlet 206 is located outside of the body of the user. When the catheter 200 is installed in a user, the resilient skirt 216 acts as a (first) positioning structure inhibiting movement of the catheter 200 out of the bladder through the urethra. The resilient skirt 216 also permits folding from its non-stressed position. This is described in more detail later with reference to FIGS. 3 and 4.

In this particular embodiment, the catheter 200 further comprises a second urine inlet 204, a second positioning structure (or anti-removal structure) 208 formed as an expandable balloon 208, and a fluid supply conduit 210 having an opening 212. The second positioning structure 208 is located between the second urine inlet 204 and the first urine inlet 214. The fluid supply conduit 210 extends from the opening 212 into the side wall of the urine conduit 202, and runs parallel to the urine conduit 202 inside the side wall thereof. The second urine inlet 204, the second positioning structure 208, and the fluid supply conduit 210 are optional features of the catheter in accordance with the invention, but advantageous as set out below.

When the catheter 200 is installed in a user, in normal use, urine enters the first urine conduit 202 through the first urine inlet 214 and exits the urine conduit 102 at the urine outlet 206 outside of the body. In normal use, the resilient skirt 216 sits adjacent to the urethral neck such that the first urine inlet 214 is located close to the neck. As such, only a small volume of urine (or substantially no urine) is able to pool within the bladder below the first urine inlet 214. This helps alleviate the above-mentioned problems with pooling in the prior art catheter 100.

The resilient skirt 216 permits folding towards the urine conduit 202 in order to allow insertion and removal of the catheter 200 from a user. The resiliency of the skirt 216 causes it to return to a substantially planar shape when no external force is applied thereto. As a result of this, if sufficient pulling force is applied to the catheter 200 while it is installed in a user, the skirt 216 will fold in a proximal direction towards the first urine inlet 214 to wrap around the urine conduit 202. As a result of this, it may be possible for the resilient skirt 216 to enter into the urethra from the bladder if the catheter 200 is pulled in a distal direction out of the urethra, and the first urine inlet 214 may therefore also enter into the urethra. This may prevent urine in the bladder entering the first urine inlet 214. The second urine inlet 204, and the positioning balloon 208, are therefore provided in this embodiment to serve as a backup mechanism to ensure that urine may continue to drain from the bladder through the urine conduit 202 in such an event, through the second urine inlet 204. The positioning balloon 208 prevents the catheter 200 from being removed from the user in the manner described previously in relation to FIG. 1 unless the positioning balloon 208 is first deflated or collapsed.

When the resilient skirt 216 is deployed in the substantially planar configuration shown in FIG. 2, it protects the first urine inlet 214 from contact with the bladder wall. The resilient skirt 216 extends outwardly from the urine conduit 202 from a position between the first urine inlet 214 and the urine outlet 206. Thus the first urine inlet 214 is situated closer to the bladder than the resilient skirt 216, with the resilient skirt 216 lying against, and in contact with, the bladder wall. Therefore, as urine flows into the first urine inlet 214, the resilient skirt 216 acts as an inlet protector to prevent any of the bladder tissue from being sucked into the inlet. Additionally, as there is no tissue contact with the first urine inlet 214, there is less risk of damage to the bladder wall, less risk of blockage due to tissue particles and less risk of biofouling at the first urine inlet 214. All together, these benefits result in the first urine inlet 214 remaining unblocked for longer, thereby ensuring that a higher urine flow rate can be maintained for longer. This higher flow rate in turn ensures good flushing through the first urine inlet 214 which maintains a clear first urine inlet 214.

With less blockage of the first urine inlet 214 and less risk of infection due to lower residual urine retention, the catheter may be less of a risk to the user and it may be possible to leave the catheter in place for longer without risk to the user.

In a set of embodiments, the longitudinal separation D1 between the distal surface of the positioning balloon 208 when in the expanded configuration shown in FIG. 2 and the resilient skirt 216 when in the non-stressed position shown in FIG. 2 is only marginally greater than the maximum lateral separation D2 between an edge of the resilient skirt 216 and an exterior surface of the urine conduit. In this particular embodiment, the longitudinal separation D1 is 20% greater than the maximum lateral separation D2. Such a separation advantageously ensures that the catheter 200 is prevented from being pulled into the urethra so as to cause the skirt 216 to fold and fully enter the urethra. This allows the resiliency of the skirt 216 to push against the urethral neck and move the catheter 200 back into the optimal position with the first urine inlet 214 being located in the bladder, close to the urethral neck. The urethral neck is tapered as the urethra widens into the bladder. So long as the resilient skirt 216 is not pulled so far down into the urethra that it is folded fully against the urine conduit 202, there will be some biasing force from the contact of the resilient skirt 216 with the urethral neck that urges the catheter 200 in the proximal direction so that it remains inside the bladder with the first urine inlet 214 open.

In other embodiments, the longitudinal separation D1 may be smaller than the maximum lateral separation D2, or it may be larger, e.g. up to 100% larger, than the maximum lateral separation D2. Such embodiments may also provide the above-mentioned advantages in relation to the resilient skirt 216 moving the catheter 200 back into the optimal position.

FIGS. 4*a-d* show an embodiment in which the longitudinal separation D1 is smaller than the maximum lateral separation D2 such that the skirt 216 overlaps with the balloon 208 as it folds towards the urine conduit (e.g. as the catheter 200 moves towards the urethra). In this configuration, the first urine inlet 214 remains open as the balloon 208 prevents the skirt 216 from folding up completely over the first urine inlet 214.

The proximal end 217 of the urine conduit 202 is rounded, and the urine conduit 202 has a substantially circular cross-section. This ensures that there are no sharp or angled edges present on the urine conduit which could damage or cause discomfort to a user during insertion or removal of the catheter 200 or while it is installed in a user. The rounded proximal end 217 of the urine conduit 202, which is the first portion of the catheter 200 to enter the urethra during insertion of the catheter 200, furthermore reduces the pressure applied to the urethral meatus during such insertion, thereby reducing risk of damage and increasing comfort during insertion.

The urine conduit 202 is formed from a flexible biocompatible material e.g. silicone to allow it to conform to the natural longitudinal shape of the urethra. The urine conduit 202 is also slightly laterally compressible thereby allowing it to conform to the cross-sectional shape of the urethra.

In some embodiments, the catheter 200 may include a manually operable valve mechanism therein which allows the user to control whether urine is allowed to pass through the urine conduit 202 or not, and thus control when urination occurs. This is described in more detail with reference to FIGS. 5*a-d.*

Figure 3:
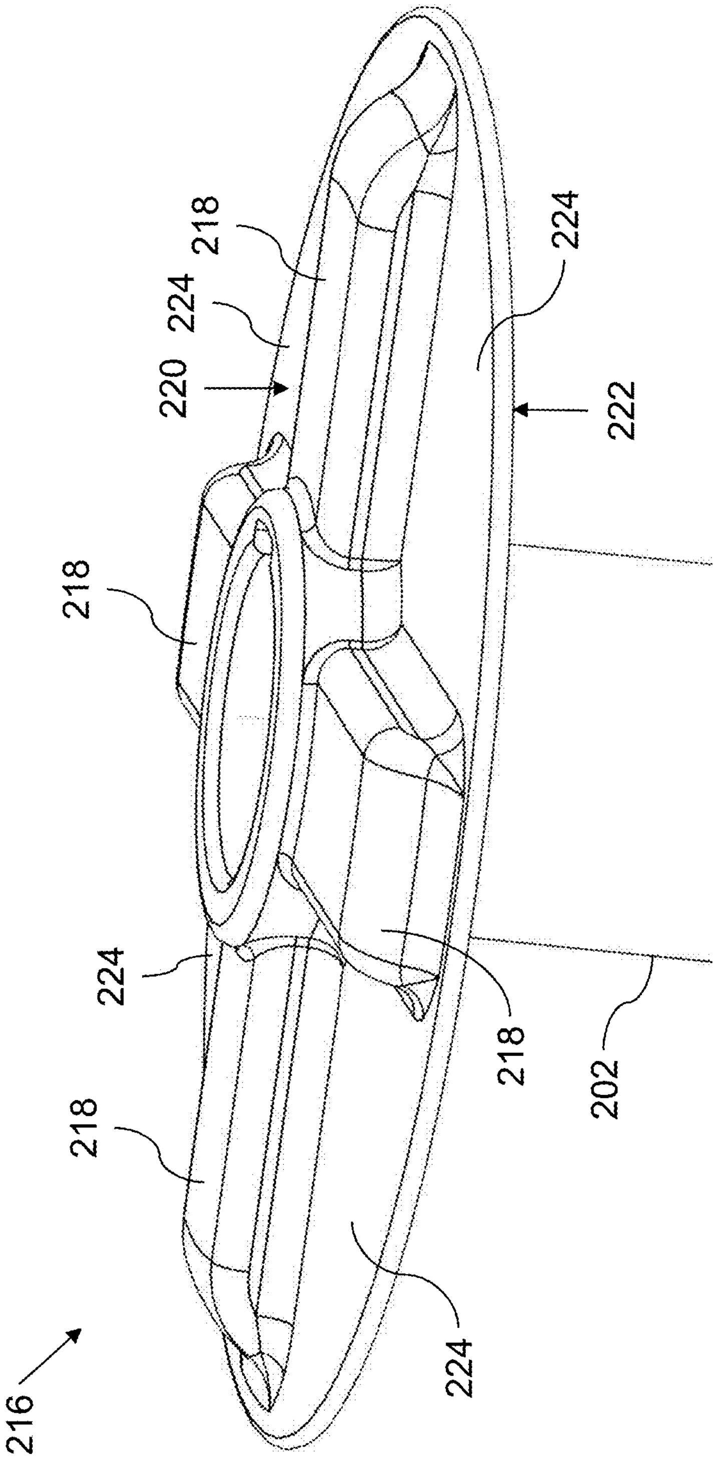
FIG. 3 is a perspective view of a resilient inlet protector skirt for a catheter in accordance with an embodiment of the invention.

FIG. 3 shows the resilient skirt 216 in more detail, shown in its non-stressed position. The skirt 216, in its non-stressed position, is substantially planar, and forms an overall disc-like shape. It comprises four radially extending ridges 218 protruding from a first face 220 thereof (facing towards the first urine inlet 214 of the catheter 200). The second, opposite face 222 is substantially smooth, and is designed for contact with the bladder wall when the catheter 200 is installed in a user. Extending between the four radially extending ridges 218 is a portion of comparatively thin material 224.

The four radially extending ridges 218 provide the skirt 216 with resiliency—i.e. they ensure that the skirt 216 returns to the non-stressed position shown in FIG. 3 after being deformed away therefrom though application of an external force. The portions of comparatively thin material 224 provides the skirt 216 with flexibility. These portions are able to fold in on themselves in certain circumstances. The skirt 216 in this embodiment is formed as a single integrally moulded piece, which may be integrally moulded with the urine conduit 202 or attached thereto e.g. using a biocompatible adhesive. The skirt 216 may be formed from silicone. The outer ends of the radially extending ridges 218 taper in thickness from their thickest points to the level of the thin material 224 extending therebetween so as to form an overall smooth surface without any sharp or angled edges. The upper surfaces of the ridges 218 (the surface furthest from the thin material 224) also have a rounded profile without sharp edges.

In this embodiment, the radially extending ridges 218 are about five times thicker (at their thickest points) than the portions of comparatively thin material 224 extending therebetween—with the ridges 218 being approximately 1 mm thick and the material 224 being approximately 0.2 mm thick. This is not limiting, however. Different thicknesses and/or ratios could be applied in other embodiments.

Figure 11A:
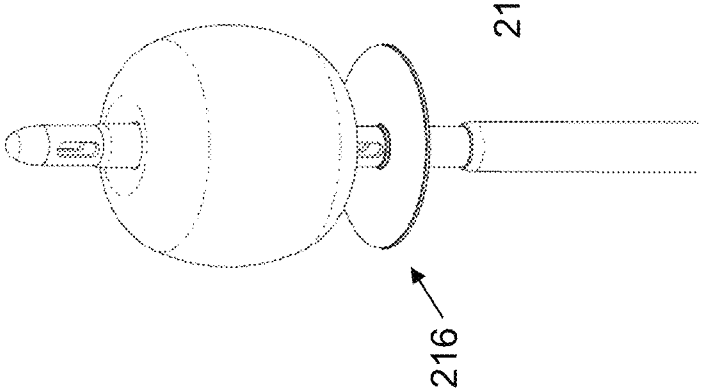
FIGS. 11*a-e* show various forms of an inlet protector, in the form of a resilient skirt for a catheter in accordance with an embodiment of the invention.
Figure 11B:
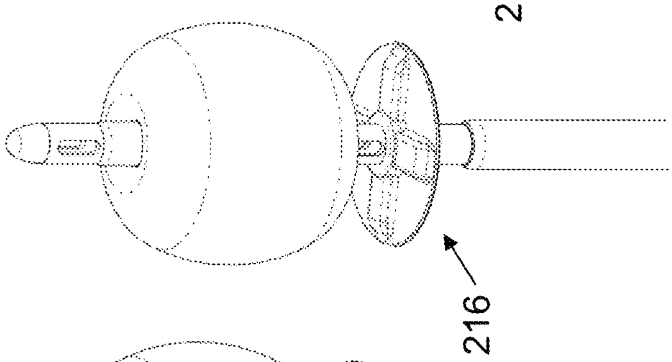
Figure 11C:
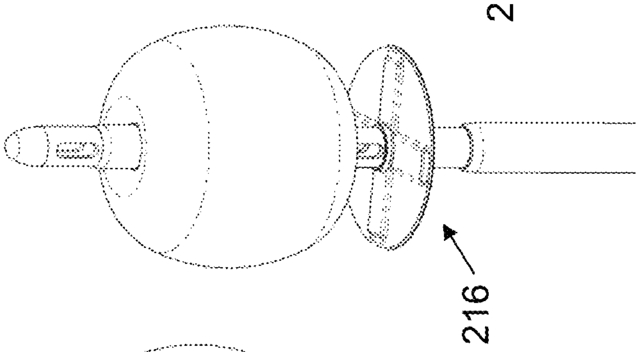
Figure 11D:
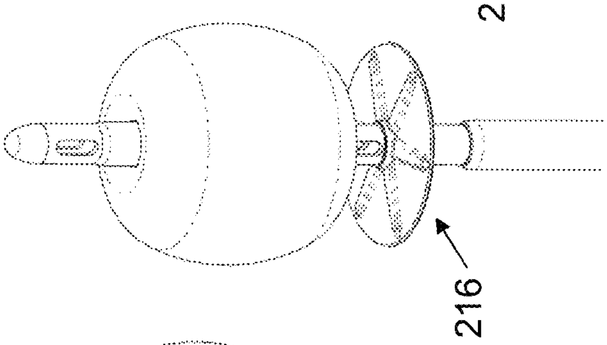
Figure 11E:
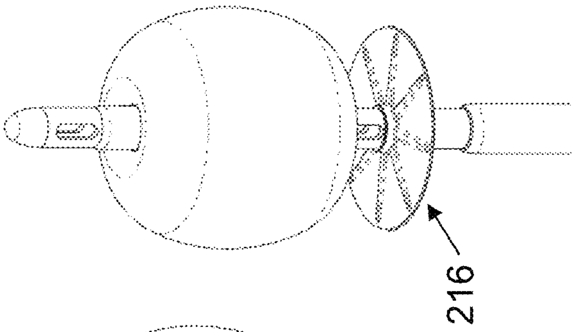

FIGS. 11*a* to 11*e* show alternative forms of the inlet protector or skirt 216. FIG. 11*a* shows a skirt with no ridges on it. Such a skirt may have no, or minimal, resilience, but still acts as an inlet protector. FIGS. 11*b* and 11*c* show arrangements of a skirt 216 with four ridges 218. FIG. 11*b* has the ridges 218 extending from a central circular hub, while FIG. 11*c* has no such hub. FIG. 11*d* shows a skirt 216 with six ridges 218 and FIG. 11*e* shows a skirt 216 with eight ridges 218.

Figures 4A, 4B, 4C, 4D:
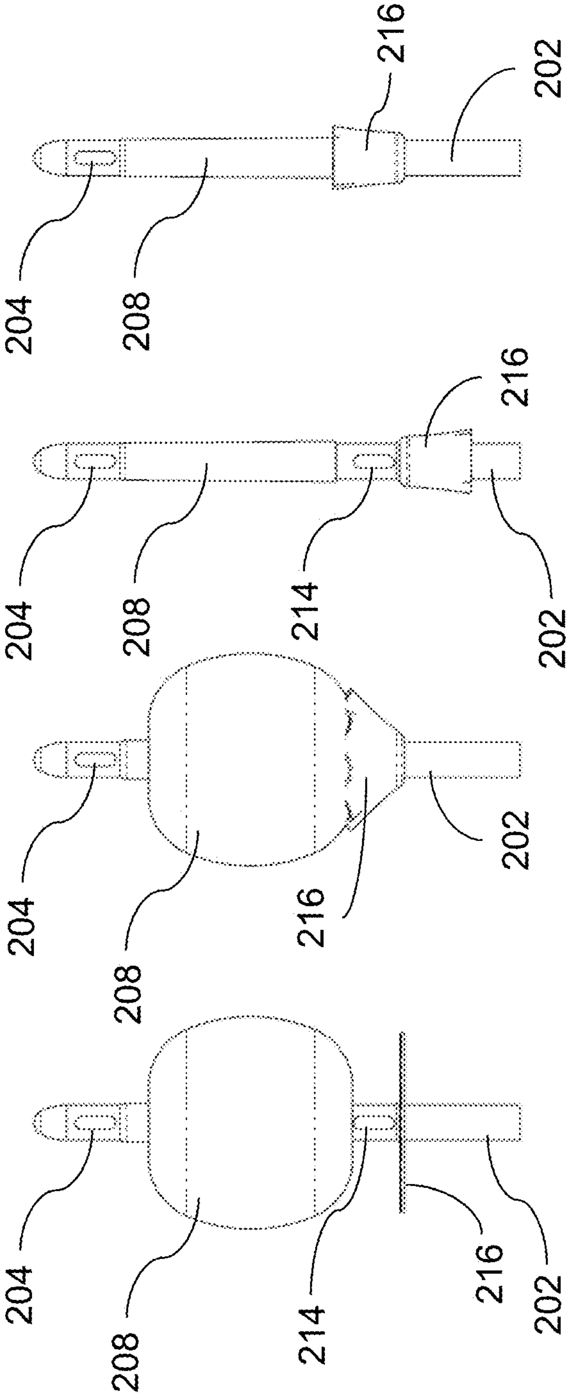
FIGS. 4*a-d* are perspective views of a resilient inlet protector skirt on a catheter in accordance with embodiments of the invention in various positions.

FIGS. 4*a-d* show various side views of the resilient skirt 216 illustrating how it can deform in various ways. FIG. 4*a* shows the resilient skirt 216 in a non-stressed position, extending radially from the urine conduit 202 and forming a substantially planar shape as discussed previously with reference to FIG. 3. The skirt 216 permits folding in a distal direction towards the urine outlet 206 (not shown in FIGS. 4*a-d*), and in a proximal direction towards the first urine inlet 214.

FIG. 4*c* shows the skirt 216 in a folded configuration wrapping around urine conduit 202 in a distal direction towards the urine outlet 206 (not shown) and a deflated balloon 208. The skirt 216 adopts this configuration while the catheter 200 is being inserted into a urethra. This allows the catheter 200 to have an overall small cross-sectional area, and avoids the skirt 216 from inhibiting insertion of the catheter 200 into a user.

FIG. 4*b* shows the skirt 216 folded into a substantially truncated-cone-shaped configuration. FIG. 4*b* shows the skirt 216 folded up against the balloon 208, representing a limit to the extraction of the catheter while the balloon 208 is deployed. This cone-shaped configuration is similar to the natural state of the skirt 216 whilst it is installed in a user when it is held in the optimal position. In that position, the proximal portion of the urine conduit 202 relative to the skirt 216 is located within the bladder, the distal portion of the urine conduit 202 relative to the skirt 216 is located within the urethra, and the skirt 216 is located at least partially in the urethral neck and conforming to the shape thereof. In that natural state, the cone shape is slightly flatter than shown in FIG. 4*b* such that there is a separation between the skirt 216 and the balloon 208 allowing urine to flow towards the first urine inlet 214 at a high rate. It may be noted that this configuration is different from the non-stressed configuration of FIG. 4 *a. A* combination of gravity, friction and pressure from urine in the bladder can bias the skirt 216 into this configuration. It can also be seen that in this configuration the skirt 216 axially overlaps with the first urine inlet 214, i.e. there is a range of axial positions of the urine conduit 202 at which both the skirt 216 and the first urine inlet 214 can be found. In this example, there is a full overlap, i.e. when the skirt 216 is in the position shown in FIG. 4*b*, it overlaps the full axial extent of the first urine inlet 214.

FIG. 4*d* shows the skirt 216 is in a folded configuration wrapping around the urine conduit 202 in a proximal direction towards the first urine inlet 214. The skirt 216 adopts this configuration while the catheter 200 is being removed from a urethra. The balloon 208 is shown deflated in FIG. 4*d*, ready for extraction. The first urine inlet 214 is completely covered and protected by the skirt 216 in this configuration. It can be seen that here there is also full axial overlap between the skirt 216 and the first urine inlet 214.

The skirt 216 moves between the various positions shown in FIGS. 4*a-d* through application of external force thereto, and can return to the non-stressed position shown in FIG. 4*a* by action of its resiliency. Alternatively, in embodiments in which the skirt 216 has little or no resiliency, the skirt 216 can return to this position through manual manipulation of the catheter by the user, or it may return through natural body movements.

FIGS. 5*a-d* show schematic cross-sections of catheters 200*a-d* in accordance with embodiments of the invention illustrating manually operable valve mechanisms which can be used to control urine flow.

All of FIGS. 5*a-d* show the urine conduit 202*a-d* having a rounded proximal end 217 *a-d*, the first urine inlet 214 *a-d* and the second urine inlet 204*a-d*. The inlet protector (e.g. resilient skirt 216), the positioning balloon 208 and the fluid supply conduit 210 are not shown in FIGS. 5*a-d* for the sake of simplicity. Each of the valve mechanisms comprise a fluid-based actuator 226*a-d* comprising an expandable chamber which is adjustable from a contracted configuration where it contains little or no fluid and an expanded configuration where it is filled with fluid, and an actuation conduit 228*a-d* operably coupled to the expandable chamber of the fluid-based actuator 226*a-d* to allow fluid to be forced into and/or removed therefrom.

Figure 5B:
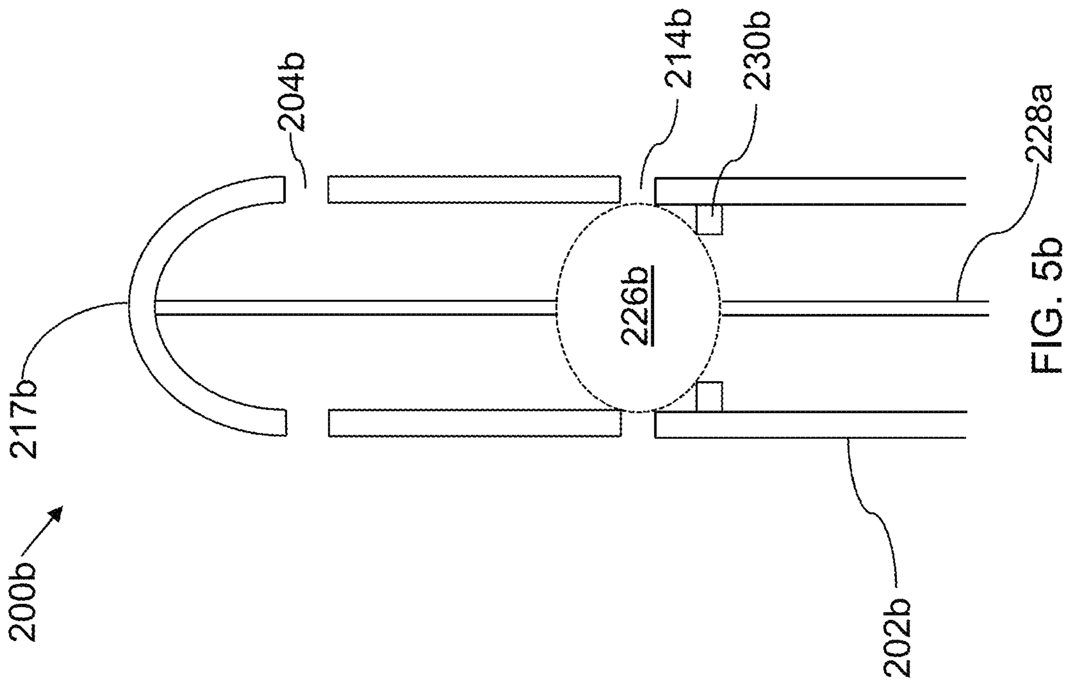
FIGS. 5*a-d* are schematic cross-sections of catheters in accordance with embodiments of the invention illustrating manually operable valve mechanisms for controlling urine flow.
Figure 5A:
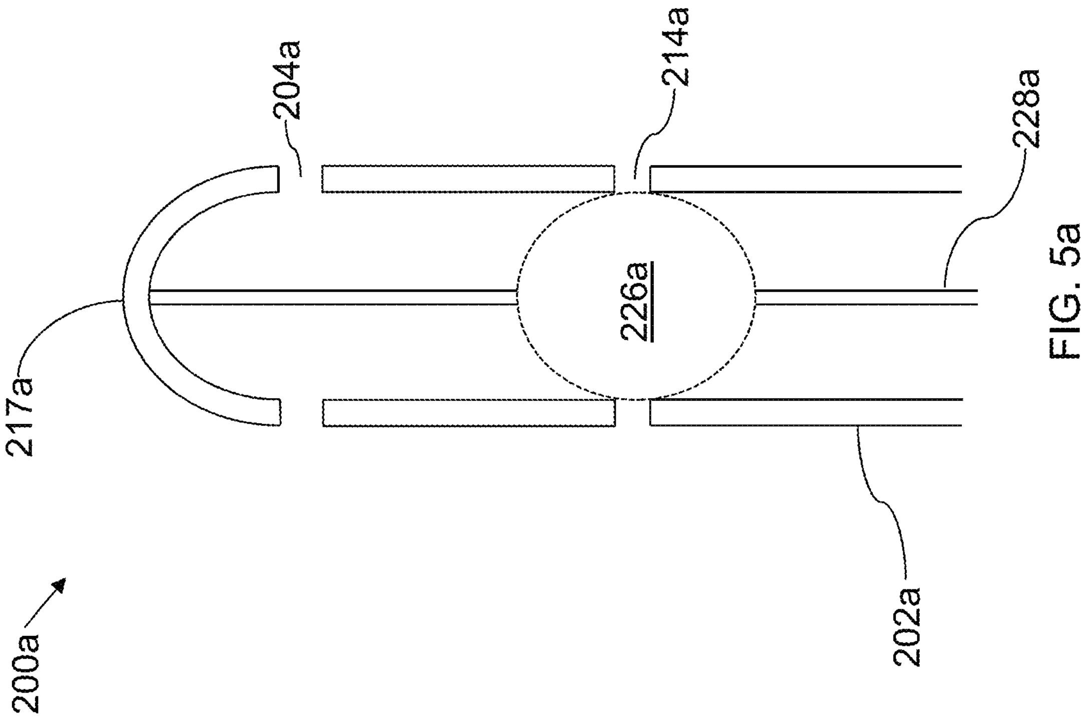

In the embodiment of FIG. 5*a*, catheter 200*a* comprises an actuation balloon 226*a* formed from resilient material e.g. silicone which functions as a manually operable valve mechanism, with the actuation balloon 226*a* functioning as the fluid-based actuator. The actuation balloon 226*a* is located in the flow path between the first urine inlet 214*a* and the urine outlet (not shown in FIG. 2*a*), as well as between the second urine inlet 204*a* and the urine outlet. The actuation balloon 226*a* has an expandable chamber which, when filled with fluid (e.g. air, water, or any other biocompatible fluid), expands from a contracted configuration to an expanded configuration (the expanded configuration being illustrated in FIG. 2*a*). When in the expanded configuration, the actuation balloon 226*a* has a substantially ovoid shape.

The actuation conduit 228*a* extends through the urine conduit 202*a* and is operably coupled to the actuation balloon 226*a* in order to allow fluid to be forced into and removed from the expandable chamber of the actuation balloon 226*a*. The actuation conduit 228*a* also extends through the actuation balloon 226*a* and is attached to the internal surface of the rounded proximal end 217*a* of the urine conduit 202*a* in order to keep the actuation balloon 226*a* in position relative to the first urine inlet 214*a*. One or more holes are formed in the side wall of the actuation conduit 228*a* in order to allow fluid communication between the actuation conduit 228*a* and the expandable chamber of the balloon 226*a*. Since the cross-sectional area of the actuation conduit 228*a* is small relative to the cross-sectional area of the urine conduit between the urine inlets 214*a*, 204*a* and the urine outlet, its presence in the flow path does not significantly impact the overall flow rate of urine out of the bladder.

When the actuation balloon 226*a* is in the contracted configuration, the surface thereof contracts away from the first urine inlet 214*a*, thereby allowing urine to enter the urine conduit 202*a* through the first urine inlet 214*a* and allowing urine to pass from the second urine inlet 204*a* to the urine outlet. Urine can then flow out of the bladder, past the actuation balloon 226*a*, through the urine conduit 202*a* and out of the urine outlet. When fluid is forced into the expandable chamber of the actuation balloon 226*a* using the actuation conduit 228*a*, it expands into the expanded configuration shown in FIG. 5*a* and abuts the peripheral walls of the first urine inlet 214*a*, thereby forming a seal which prevents urine from entering the urine conduit therethrough. When the actuation balloon 226*a* is in the expanded configuration, it protrudes slightly into the first urine inlet 214*a* in order to ensure that a tight seal is formed therewith. The actuation balloon 226*a* also abuts the interior wall of the urine conduit 202*a* when in the expanded configuration thereby preventing urine that enters the urine conduit via the second urine inlet 204*a* from flowing through to the urine outlet. Fluid can then be removed from the actuation balloon 226*a* in order to move it back to the contracted configuration and thus allow urine to flow through the urine conduit 202*a*.

In the embodiment of FIG. 5*b*, the catheter 200*b* comprises an actuation balloon 226*b* formed from resilient material which functions as a manually operable valve mechanism, with the actuation balloon 226*b* functioning as a fluid-based actuator. The catheter 200*d* functions in much the same manner as described previously in relation to FIG. 5*a*. However, in addition to abutting the peripheral walls of the first urine inlet 214*b* and forming a seal therewith when in the expanded configuration, the urine conduit 202*b* further comprises a constricted portion 230*b*, formed as an annular rim protruding from the internal surface thereof, which the actuation balloon 226*b* also abuts when in the expanded configuration. This provides additional sealing between the first and second urine inlet 214*b*, 204*b* and the urine outlet (not shown in FIG. 5*b*), thereby reducing the risk of urine leakage particularly where the catheter 220*b* is installed in a user for an extended period of time. This is also particularly useful in embodiments where additional holes are provided in the walls of the urine conduit 202*b*—e.g. additional holes at the rounded proximal end 217*b* of the urine conduit 202*b* for allowing instrument insertion therethrough (not shown in FIG. 5*b*)—since urine flow through such holes to the urine outlet is also prevented by the actuation balloon 226*b* when in the expanded configuration. In other embodiments, the balloon 226*b* may not abut the first inlet holes 214*b* in the expanded configuration, but rather only abut the constricted portion 230*b* of the urine conduit 202*b*, provided the constricted portion 230*b* is located between both urine inlets 214*b*, 204*b* and the urine outlet.

Figure 5D:
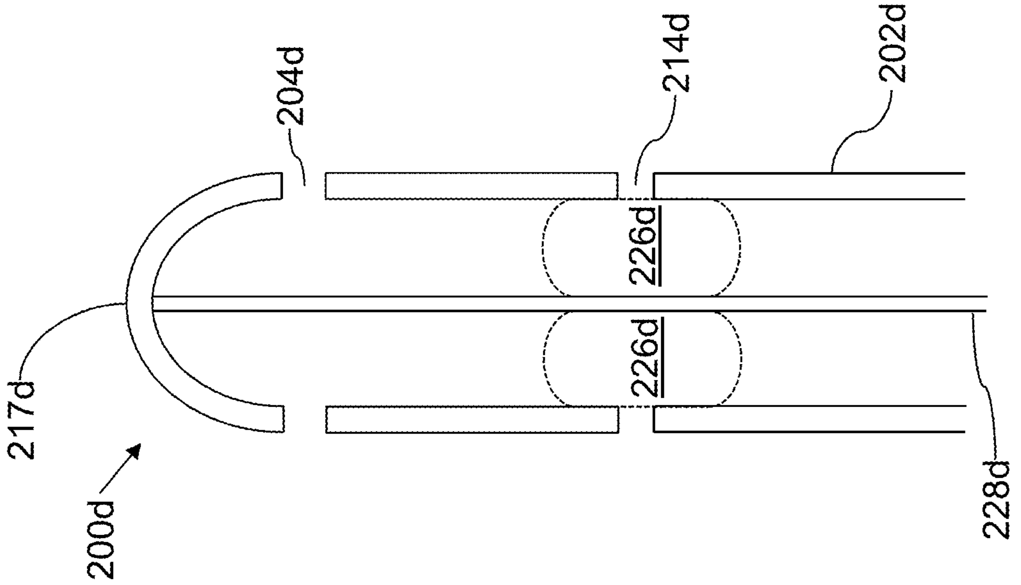
Figure 5C:
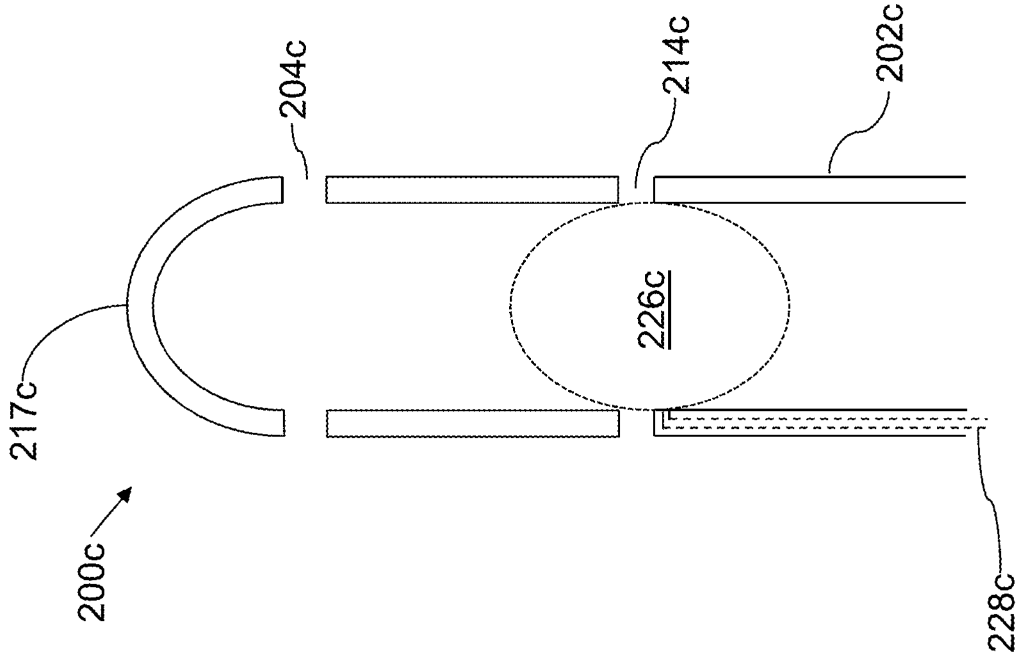

In the embodiment of FIG. 5*c*, the catheter 200*c* comprises an actuation balloon 226*c* formed from resilient material which functions as a manually operable valve mechanism, with the actuation balloon 226*c* functioning as a fluid-based actuator, in much the same manner as described above with reference to FIG. 5*a*. The catheter 200*c* differs from the catheter 200*a* shown in FIG. 5*a* in that the actuation conduit 228*c* is embedded in the wall of the urine conduit 202*c*, rather than located in the flow path between the urine inlets 214*c*, 204*c* and the urine outlet (not shown in FIG. 5*c*). This maximises the cross-sectional area of the flow path between the urine inlets 214*c*, 204*c* and the urine outlet, thus increasing flow rate, while also protecting the actuation conduit 228*c* from damage e.g. due to deposits thereon from urine passing through the urine conduit 202*c*. The actuation conduit 228*c* exits the walls of the urine conduit 202*c* at a location corresponding to the location of the actuation balloon 226*c*, and extends partially into the expandable chamber of the actuation balloon 226*c* so as to enable fluid communication therebetween. The actuation balloon 226*c* also has a slightly different overall ovoid shape compared to the balloon 226*a* shown in FIG. 5*a*, but otherwise operates in a similar manner.

In the embodiment of FIG. 5*d*, the catheter 200*d* comprises an actuation balloon 226*d* formed from resilient material which functions as a manually operable valve mechanism, with the balloon 226*d* functioning as a fluid-based actuator, in much the same manner as described above with reference to FIGS. 5*a-c*. The actuation balloon 226*d* differs from the actuation balloons 226*a-c* in that it has an overall toroidal shape having a central opening through which the actuation conduit 228*d* extends. One or more holes are formed in the side wall of the central opening of the toroidal actuation balloon 226*d*, and in the side wall of the actuation conduit 228*d*, which enable fluid communication between the actuation conduit 228*d* and the actuation balloon 226*d*.

It will thus be seen that each of the catheters 200*a-d* discussed above comprises a fluid-based actuator 226 with an expandable chamber adjustable from a contracted configuration to an expanded configuration via insertion and removal of fluid through an actuation conduit 228, and that in one of the expanded or contracted configurations urine is prevented from flowing from the first urine inlet 214 (and the second urine inlet 204 where present) to the urine outlet 206, and in the other configuration urine is able to flow from the first urine inlet 214 (and the second urine inlet 204 where present) to the urine outlet 206. It will be appreciated by those skilled in the art that the various features discussed above in relation to the embodiments of FIGS. 5*a-d* could be combined in any appropriate manner, e.g. by changing from an embedded actuation conduit 228 to an actuation conduit 228 located in the flow path or vice versa, etc.

FIGS. 6 to 11 show a number of embodiments that show variations and additional features of the catheter 200.

Figure 6:
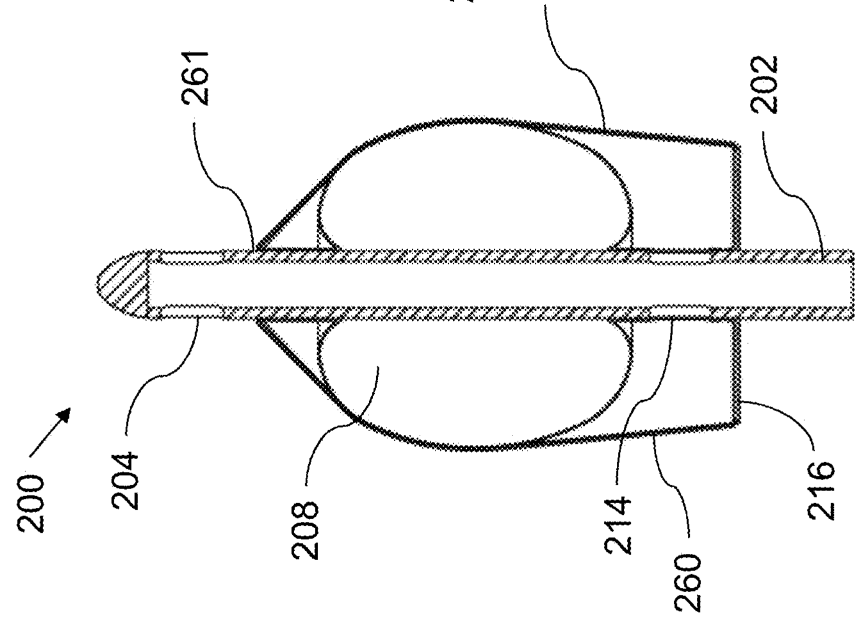
FIG. 6 is a schematic cross-section of another catheter in accordance with an embodiment of the invention.

FIG. 6 shows a catheter 200 similar to that of FIG. 2. The catheter 200 is shown in cross-section illustrating the toroidal shape of the balloon 208 and its position between the first fluid inlet 214 and the second fluid inlet 204. FIG. 6 additionally shows straps 260 which attach to an upper attachment point 261 on the urine conduit 202 and at a lower end to the skirt 216. The straps 260 serve to pull the skirt 216 into the desired deployed position as the balloon 208 expands. This ensures that the skirt 216 unfolds from its insertion position (shown in FIG. 4*c* where it is folded towards the distal end of the catheter 200) so that it correctly deploys to the position shown in FIG. 6 in which it protects the first urine inlet 214 and optionally holds the catheter 200 in position at the urethral neck so as to guide urine into the urine inlet 214 without any urine pooling.

Figure 7B:
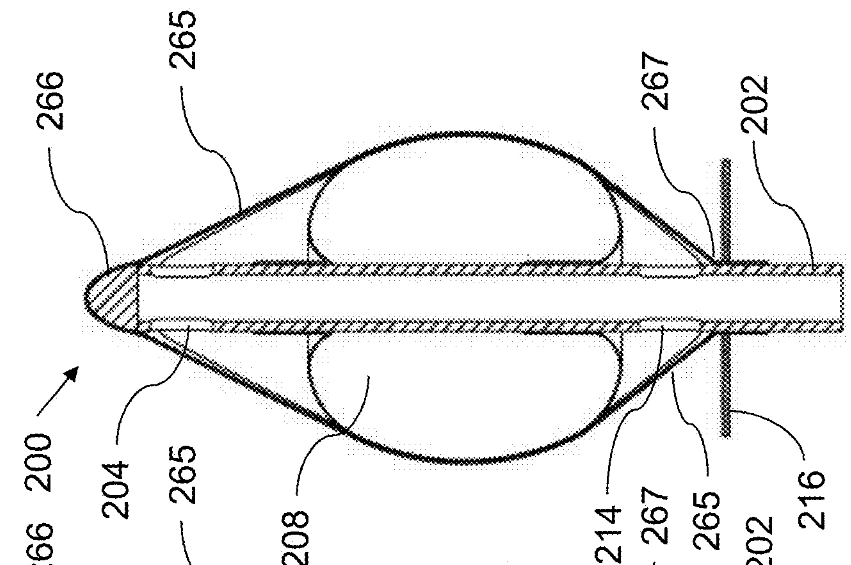
FIG. 7*a-b* are a schematic side view and cross-section respectively of another catheter in accordance with an embodiment of the invention.
Figure 7A:
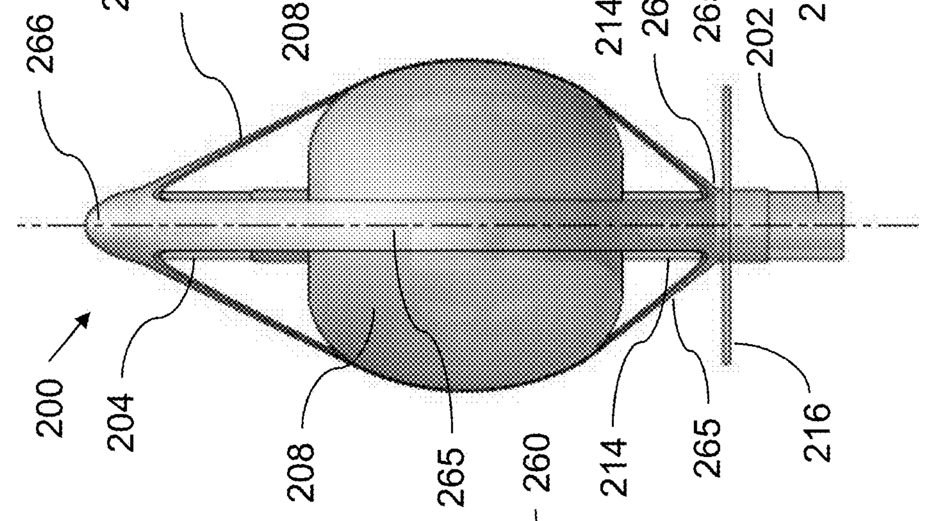

FIGS. 7*a* and 7*b* show a different set of straps 265. FIG. 7*a* shows a side view and FIG. 7*b* shows a cross-section view. Four straps 265 are provided in this embodiment, equally distributed around the urine conduit 202, although other numbers of straps 265 are possible. Each strap 265 is attached at an upper end to the tip 266 of the urine conduit 202 and at a lower end to a lower attachment point 267 adjacent to the first urine inlet 214, between the first urine inlet 214 and the urine outlet (not shown). The straps 265 pass over the outer surface of the balloon 208 and are elastic (e.g. silicone) such that as the balloon 208 is expanded inside the bladder, the straps 265 are stretched into the position shown in FIGS. 7*a* and 7*b*. When the balloon 208 collapses, the straps 265 also collapse to a position parallel to the urine conduit 202 for ease of extraction.

In the expanded configuration shown in FIGS. 7*a* and 7*b*, the straps 265 serve a number of functions. The lower part of the straps 265 serves as a barrier that prevents the skirt 216 from folding up completely against the first urine inlet 214. This ensures that the first urine inlet 214 remains open in use. Notably, there are gaps between the straps 265 so that urine can flow between them into the first urine inlet 214. The shape of the straps 265 (in particular the angle that they make between the urine conduit 202 and the balloon 208) also matches the shape of the urethral neck such that when the catheter 200 is pulled into the neck with the balloon 208 inflated, any pressure is distributed over a large area of the neck, reducing discomfort and potential damage. This shape (the angle) can be adjusted for different patient anatomies by adjusting the size of the balloon 208 and/or the position of the lower attachment point 267 on the urine conduit 202. The upper end of the straps 265 provide a protective function for the second urine inlet 204 by preventing tissue contact between the second urine inlet 204 and the bladder wall. This reduces fouling of the second urine inlet 204 and reduces suck-in of tissue during evacuation of the bladder which can cause blockage of the second urine inlet 204 and damage to the bladder wall. Finally, the cone shape provided by the straps 265 at the tip of the catheter 200 provides a more blunt shape than for example can be seen in FIG. 6 which reduces damage and/or discomfort to the user when the tip 266 contacts the bladder wall.

Figure 8A:
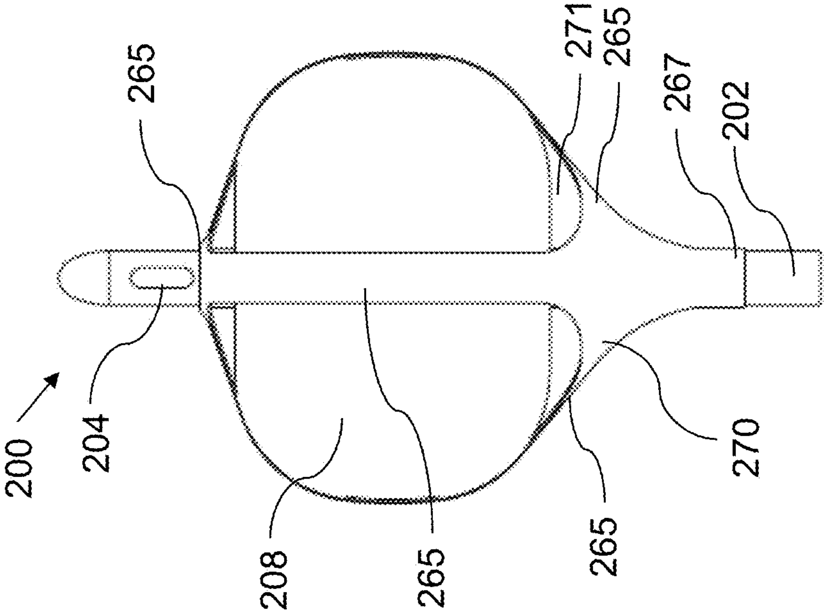
FIGS. 8*a-b* are schematic cross-sections of another catheter in accordance with an embodiment of the invention illustrating an anti-removal structure in an expanded configuration and a contracted configuration.

FIG. 8*a* shows a side view of a catheter 200 in which no skirt 216 is present. In this embodiment, the straps 265, i.e. the lower part thereof are the inlet protector, separating the first urine inlet 214 (not shown, but hidden behind the straps 265) from the bladder wall. Webbing 270 extends between the lower parts of the straps 265 so as to form a skirt-like structure around the first urine inlet 214. The extent of the webbing is selected to ensure that gaps 271 remain between the webbing 270 and the balloon 208 so that urine can flow easily to the first urine inlet 214.

Figure 8B:
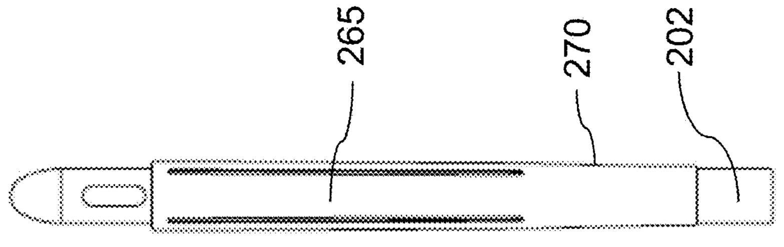

FIG. 8*b* shows the embodiment of FIG. 8*a* in the collapsed state with the balloon 208 deflated and the straps 265 contracted into a configuration parallel with the urine conduit 202 ready for insertion or extraction. In this configuration the balloon 208 is contained underneath the straps 265.

Figure 9:
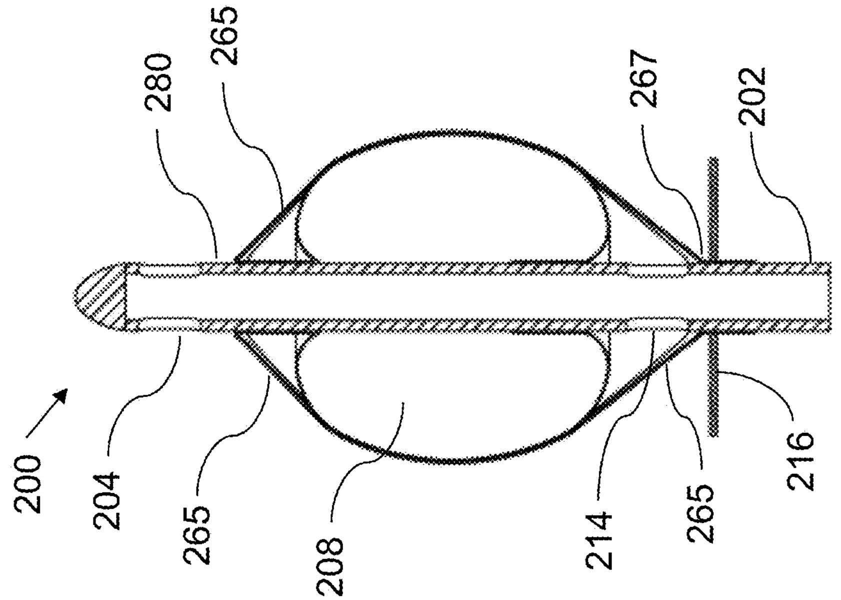
FIG. 9 is a schematic cross-section of another catheter in accordance with an embodiment of the invention.

FIG. 9 shows an embodiment which is similar to FIG. 7 but with the straps 265 attached at an upper attachment point 280 which is between the second urine inlet 204 and the balloon 208.

Figures 10A, 10B:
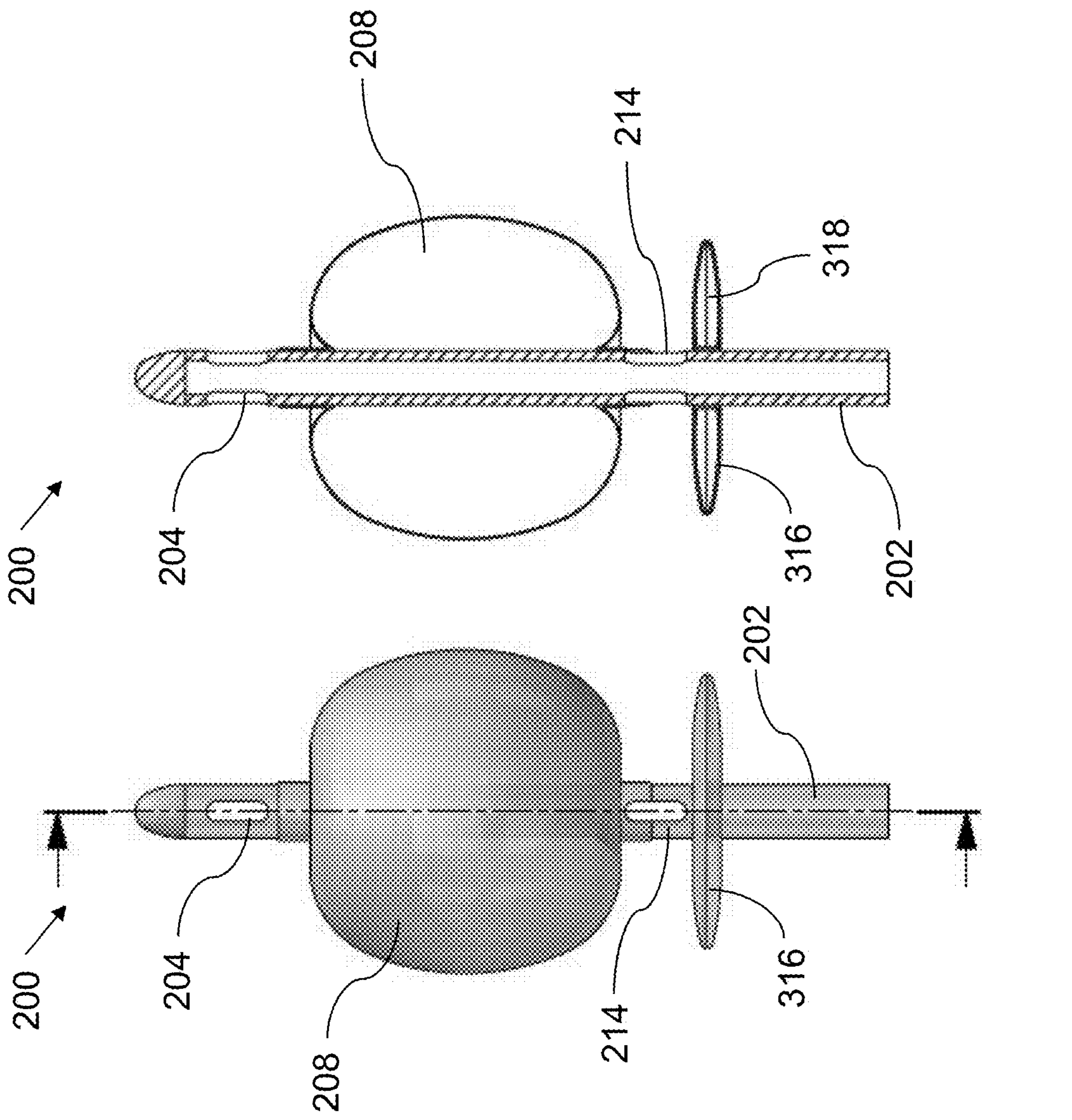
FIGS. 10*a-b* are a schematic side view and cross-section respectively of another catheter in accordance with an embodiment of the invention.

FIGS. 10*a* and 10*b* show an embodiment in which the inlet protector is an expandable skirt 316. The expandable skirt 316 is formed from an expandable skirt chamber 318 which, in use, is expanded by filling it with fluid e.g. with a sterile or non-toxic fluid such as water or saline solution. This allows the skirt 316 to vary its stiffness over a large range. In particular, when the skirt 316 is collapsed for insertion and removal, it can have a very low stiffness (and low volume) so that it is easily inserted and removed. On the other hand, when it is deployed (inflated) in the bladder, it can have a high stiffness which gives it strong resilience and strong resistance against movement out of the bladder. It thus aids in the function of positioning the first urine inlet 214 low in the bladder for maximum evacuation of urine (leaving very low quantities of residual urine) and also aids in the function of separating the first urine inlet 214 from the tissue of the bladder wall by holding the first urine inlet 214 at a distance from the bladder wall so that there is low risk of blockage and fouling. In order to maintain a high urine flow rate out of the urine conduit 202 (and thus good flushing of the bladder), the expandable skirt 316 and the balloon 208 are both inflated by the same fluid supply conduit (not shown in the figure). This is a space efficient design and makes use of the fact that both the skirt 316 and the balloon 208 will generally be deployed at the same time. However, it will be appreciated that in other embodiments the expandable skirt 316 and the balloon 208 may be separately inflatable. This may be useful if it is desired to inflate them to different pressures, e.g. to attain different stiffnesses.

Figure 12:
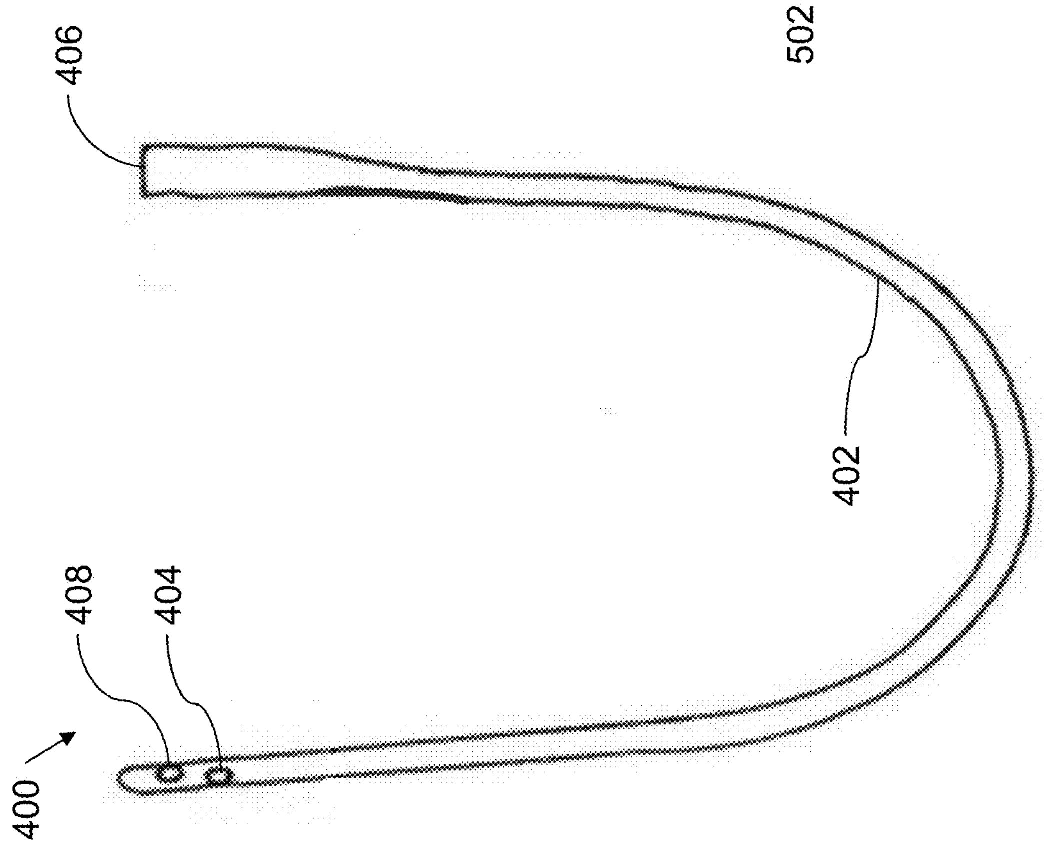
FIG. 12 (Prior art)
FIG. 12 is a schematic side view of a prior-art intermittent catheter.

FIG. 12 shows a prior art intermittent catheter 400. Such catheters are designed for temporary insertion into the bladder of a user to allow drainage of urine therefrom. After use, the catheter 400 is removed from the bladder and is typically disposed of. The intermittent catheter 400 comprises a urine conduit 402, a first urine inlet 404, a urine outlet 406, and a second urine inlet 408. The second urine inlet 408 is located axially further away from the urine outlet 406 than the first urine inlet 404.

Figure 13:
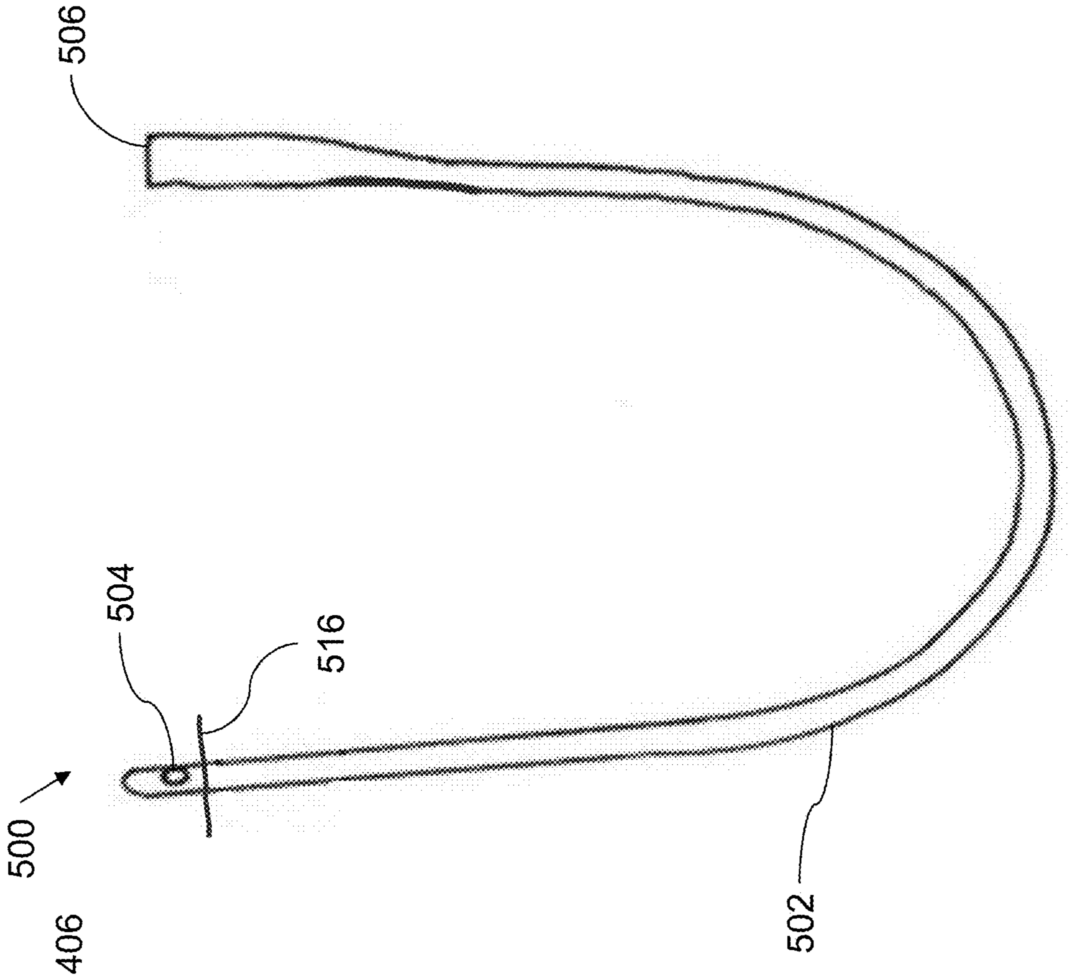
FIG. 13 is a schematic side view of an intermittent catheter in accordance with an embodiment of the invention.

FIG. 13 shows an intermittent catheter 500 in accordance with an embodiment of the invention. The intermittent catheter 500 is also designed for temporary insertion into the bladder of a user to allow drainage of urine therefrom. Unlike the prior art intermittent catheter 400, the intermittent catheter 500 comprises a resilient skirt 516 with the same function as the resilient skirts 216, 316 described previously. This means that the catheter 500 maintains its position in the bladder more effectively than the prior art catheter 400 once inserted therein by virtue of the resilient skirt 516 as described previously, while still providing easy insertion and removal by virtue of the resilient skirt 516 being able to fold around the urine conduit 502 as described previously. The resilient skirt 516 also protects the urine inlet 504 by holding it away from contact with the tissue of the bladder, thereby avoiding suck-in effects that can hinder draining of the bladder and can damage the bladder wall. It will be appreciated that in embodiments where the skirt 516 is not resilient, it still provides this inlet protecting function. The intermittent catheter 500 also comprises only a single urine inlet 504 in this embodiment, thought it will be appreciated that this is not limiting and that it may instead comprise any appropriate number of urine inlets.

The intermittent catheter 500 therefore offers the advantage of self-positioning over the prior art catheter 400, as well as offering the advantage of providing a user thereof with some feedback allowing them to feel when the catheter 500 is in the correct position (due to contact between the skirt 516 and the bladder wall).

Figures 14A, 14B, 14C, 14D:
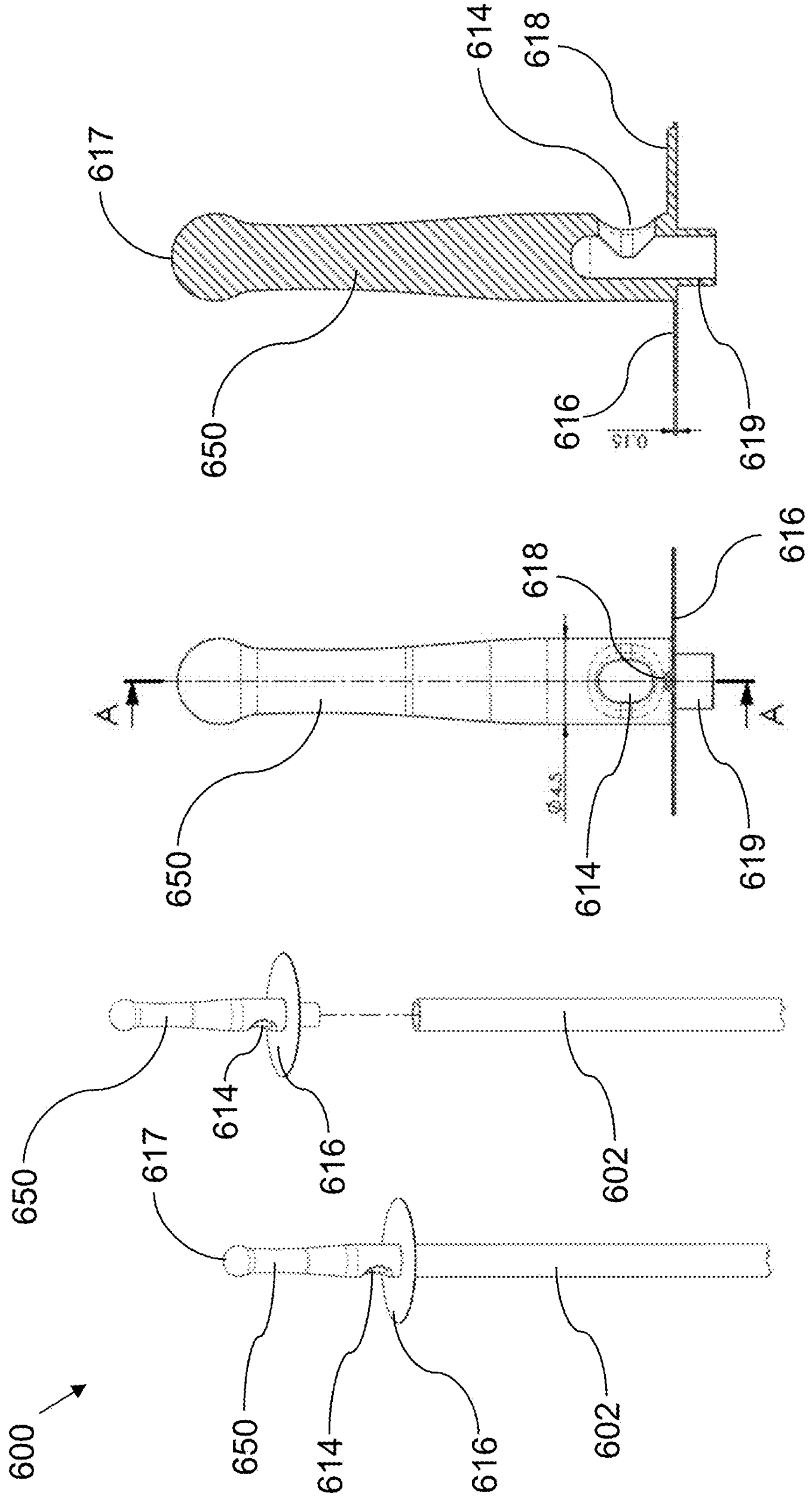
FIGS. 14*a-d* show a separate tip part and an assembly process.

FIGS. 14*a* to 14*d* show an intermittent catheter 600 comprising an outlet tube 602 and a separate tip part 650. As shown in FIG. 14*b*, the catheter 600 can be assembled by attaching the tip part 650 to the outlet tube 602. FIG. 14*a* shows the two parts in the assembled state. A tip part 650 is shown in more detail in FIG. 14*c* and the cross-section of FIG. 14*d* taken along the line A-A of FIG. 14*c*.

The tip part 650 has a proximal end 617 which is rounded to avoid sharp or angled edges which could damage or cause discomfort to a user during insertion or removal of the catheter 600. The rounded proximal end 617 is the first portion of the catheter 600 to enter the urethra during insertion of the catheter 600 and reduces the pressure applied to the urethral meatus during insertion. The tip part 650 is formed from a flexible biocompatible material e.g. silicone to allow it to conform to the natural longitudinal shape of the urethra.

The tip part 650 also includes a first urine inlet 614 and an inlet protector 616 arranged adjacent to the first urine inlet 614. The inlet protector 616 in FIGS. 14*a* and 14*b* is in the form of a flexible skirt. In this embodiment, the skirt is smooth and has no radial ridges such as are shown in FIG. 3. As the catheter 600 is an intermittent catheter, the primary function of the inlet protector 616 is to cover the first urine inlet 614. The additional resilience (e.g. for positioning or for hindering removal) that is provided by the radial ridges 218 is not necessary for this function. However, it may still be beneficial in some embodiments. For example, the tip part 650 shown in FIGS. 14*c* and 14*d* has a single radial ridge 618 positioned adjacent the first urine inlet 614 so that when the inlet protector 616 folds over the inlet 614, the ridge 618 lies over the inlet 614. The radial ridge 618 therefore prevents the inlet protector 616 from completely blocking the first urine inlet 614. Although the inlet 614 is substantially obstructed in this configuration, the radial ridge 618 maintains a small opening so that a low flow is still possible.

Figure 15D:
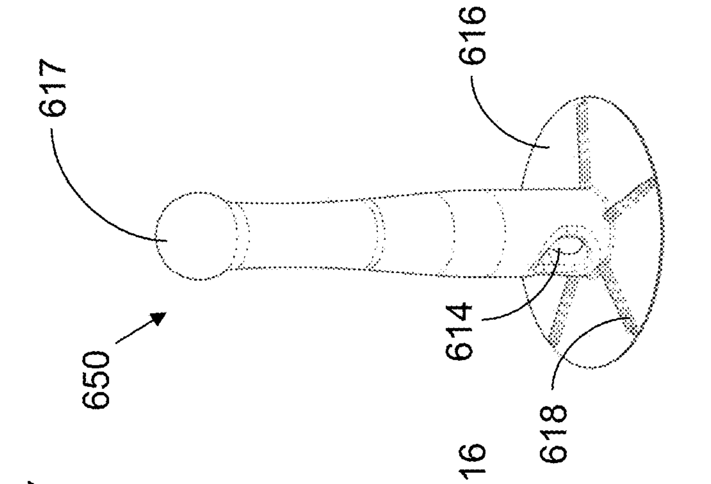
FIGS. 15*a-d* show some variations of a separate tip part.
Figure 15C:
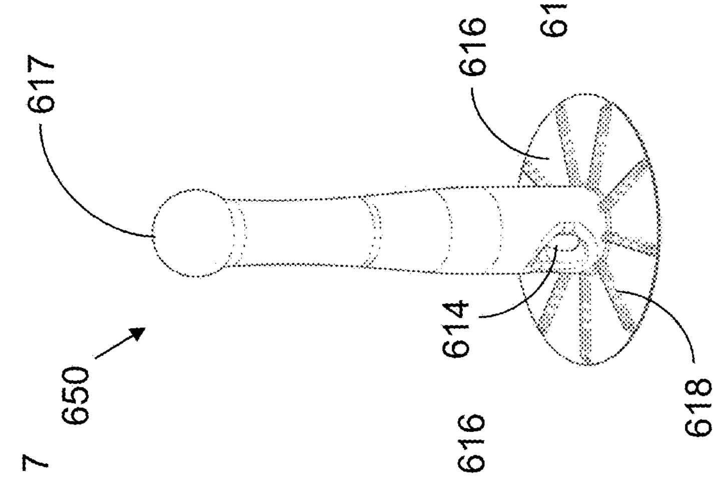
Figure 15B:
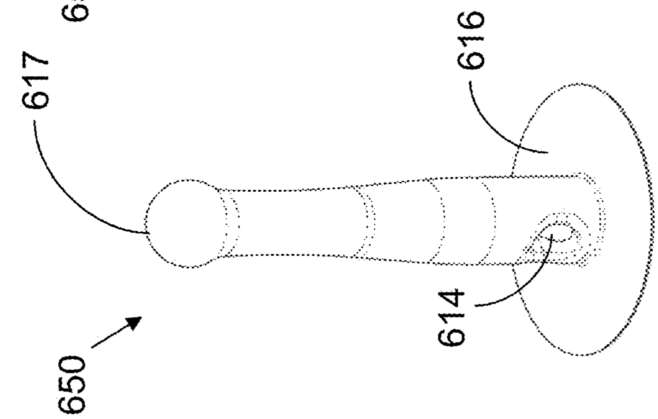
Figure 15A:
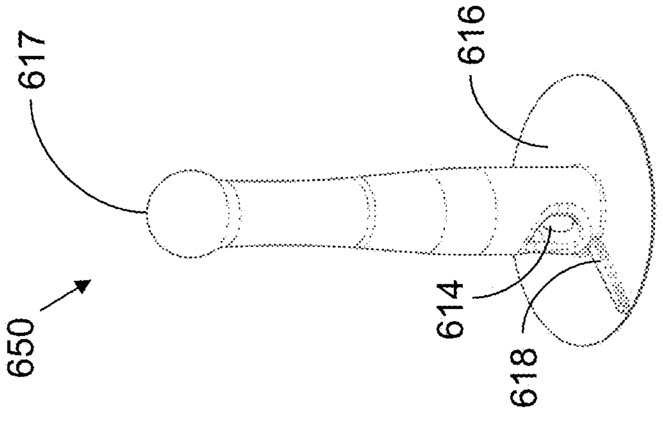

The radial ridges can provide additional functionality. For example, when the inlet protector 616 folds up or down, i.e. adjacent to the outlet tube 602 or the first urine inlet 614, it typically wrinkles as its outer circumference has to be reduced (folded) around the smaller circumference of the outlet tube 602 (or the tip 650). The number and position of radial ridges 618 can influence how the inlet protector 616 wrinkles and folds and can thus encourage a configuration in which the folds are evenly distributed around the catheter so that the maximum diameter of the folded configuration is minimised. FIGS. 15*a* to 15*d* show a number of different configurations. FIG. 15*a* shows a configuration with a single radial ridge 618. FIG. 15*b* shows no radial ridges (a smooth inlet protector 616). FIG. 15*c* shows a configuration with nine radial ridges 618 and FIG. 15*d* shows a configuration with five radial ridges 618.

As can be seen in FIG. 14*d*, the first urine inlet 614 opens into a fluid channel 615 that fluidly connects with the inside of outlet tube 602 via an attachment part 619. The attachment part 619 extends downwardly (in the figure), i.e. away from the proximal end 617. The tip part 650 is attached to the outlet tube 602 by inserting the attachment part 619 into the inside of outlet tube 602 where it may be held by a friction fit or by adhesive or by other mechanisms discussed further below.

As can best be seen in FIG. 14*d*, the first urine inlet 614 has a smooth edge with a radius of curvature that reduces its sharpness so as reduce damage and/or irritation of the user. The radius of curvature in this embodiment is about 0.6 mm.

Figure 16A:
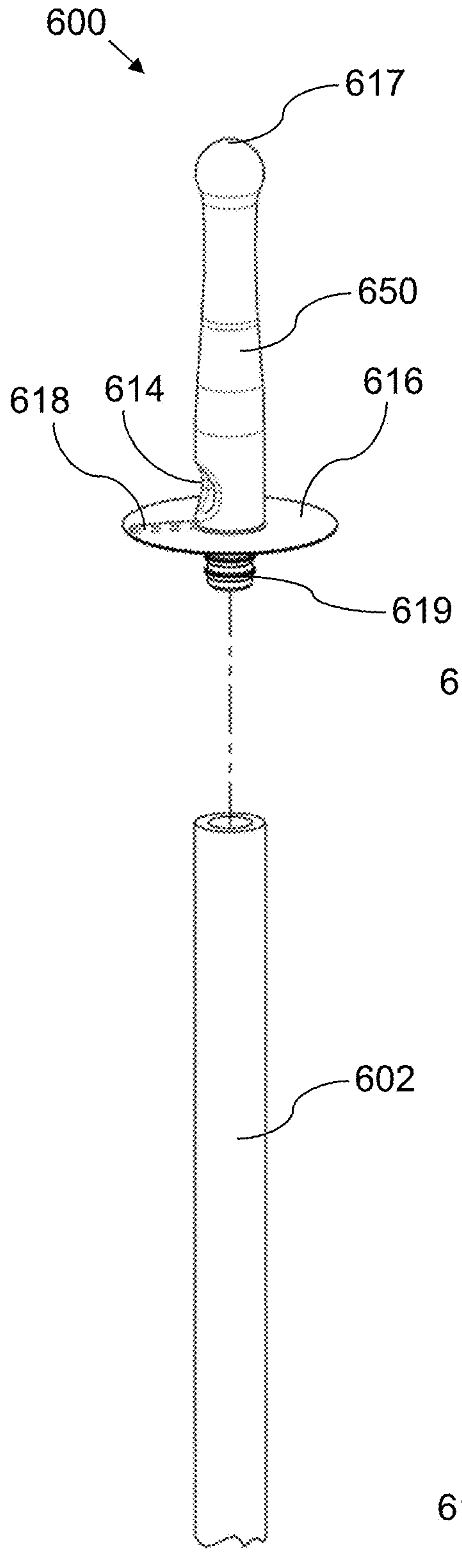
FIGS. 16*a-c* show another separate tip part and assembly process.
Figure 16B:
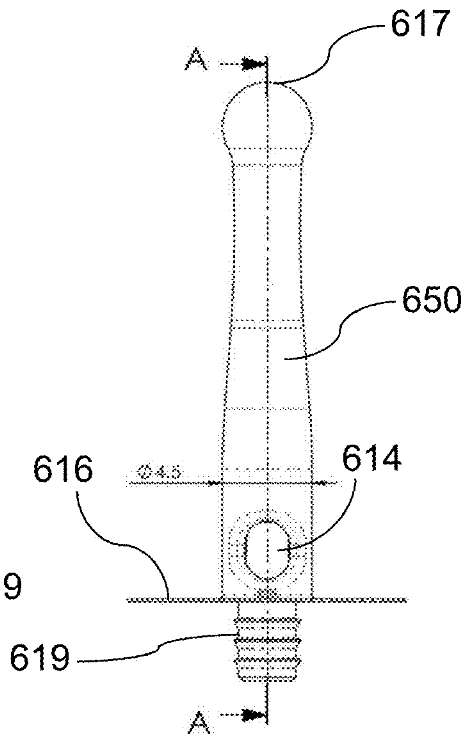
Figure 16C:
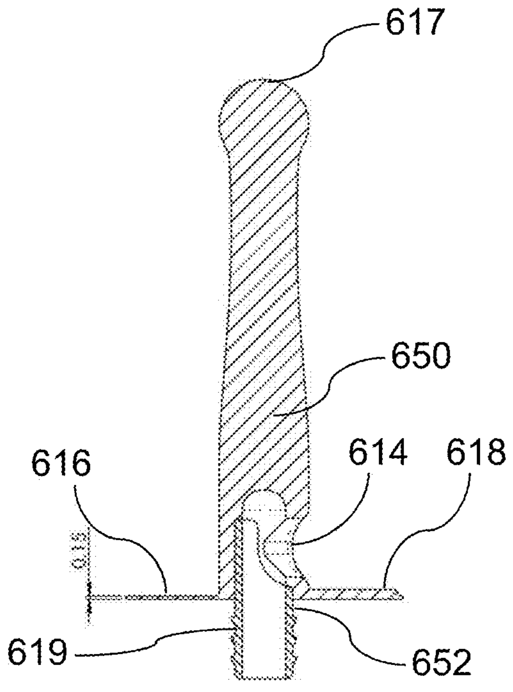

FIGS. 16*a* to 16*c* show another embodiment of a tip part 650 similar to that shown in FIGS. 14*a* to 14*d*. In this embodiment the attachment part 619 is formed from a rigid connection piece 652 that has three projections formed on it, each in the form of an annular ridge. These projections, when inserted into the outlet tube 602 as illustrated in FIG. 16*a*, press into the inside of the outlet tube 602 and increase the strength of the interference fit between them. The rigid connection piece 652 is formed from a separate, more rigid material in this embodiment as can be seen in the cross-section of FIG. 16*c*. The material should be a biocompatible material and may be a hard plastic or metal in some examples. The remainder of the tip part 650 is overmoulded over the rigid connection piece 652 using a softer material. The rigid connection piece 652 is formed as a tube and the first urine inlet 614 fluidly connects with the inside of this tube so as to provide a fluid communication path between the first urine inlet 614 and the inside of the outlet tube 602.

Figure 17A:
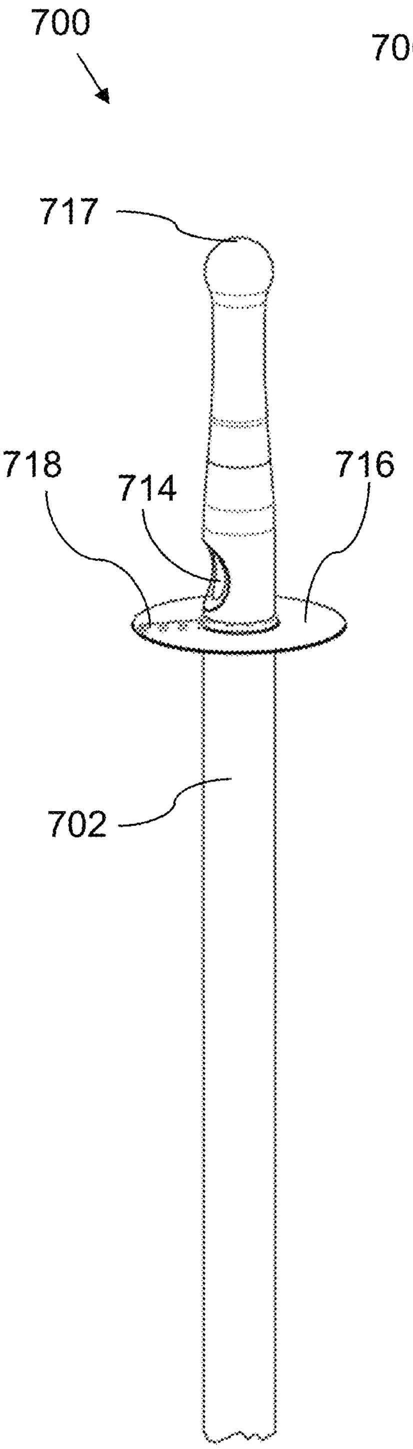
FIGS. 17*a-b* show a separate inlet protector part and an assembly process.
Figure 17B:
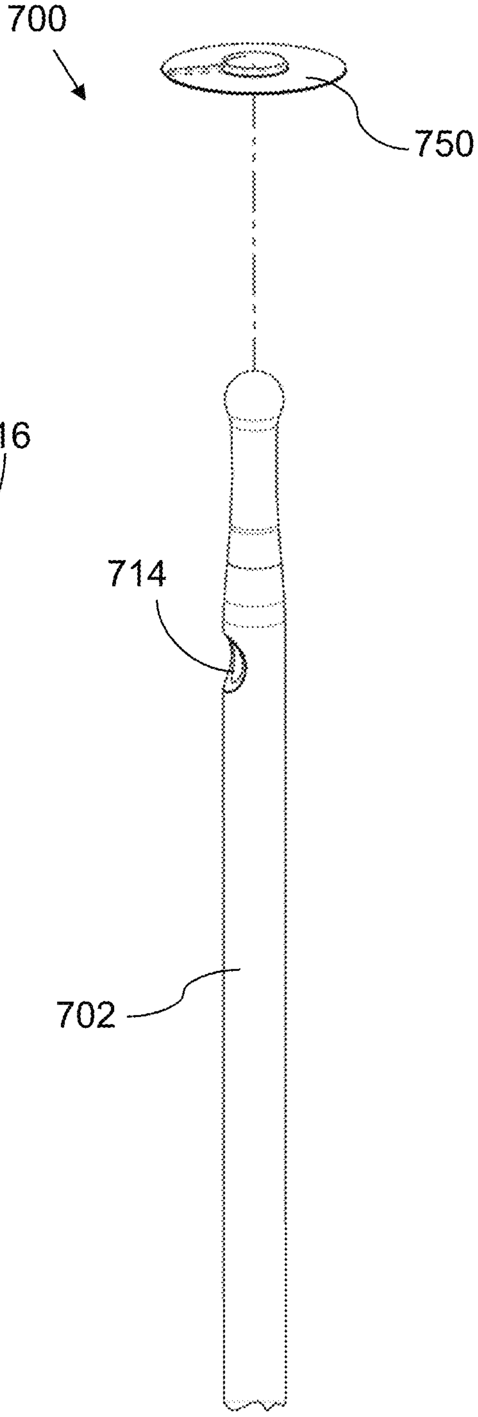

FIGS. 17*a* and 17*b* illustrate how a catheter 700 can receive a separate inlet protector part 750. The inlet protector part 750 has an inlet protector 716 extending radially outwardly therefrom and it could take many forms, e.g. as discussed above in relation to the skirt 216. In this embodiment the inlet protector 716 is a flat skirt with a single radial ridge 718 formed thereon. Ideally, when assembled, the ridge 718 is positioned adjacent to the first urine inlet 714 as shown in FIG. 17*a*. As is illustrated in FIG. 17*b*, the assembly process in this embodiment is simply to press-fit the inlet protector part 750 over the rest of the catheter 700. In other words, the only force holding the inlet protector part 750 in place is friction. The inlet protector part may have its inner diameter formed slightly smaller than the outer diameter of the catheter 700 so that the two parts form an interference fit. As the forces acting on the inlet protector 716 are low during insertion and removal (friction forces with the inner wall of the urethra are lower than the frictional forces holding the inlet protector part 750 in place against the rest of the catheter 700), there is no need for additional manufacturing steps to secure the inlet protector part 750 in place. This makes for fast assembly. Of course if further security is desired then an adhesive may be applied or a further adhering process (such as heating) can be applied.

Figure 18A:
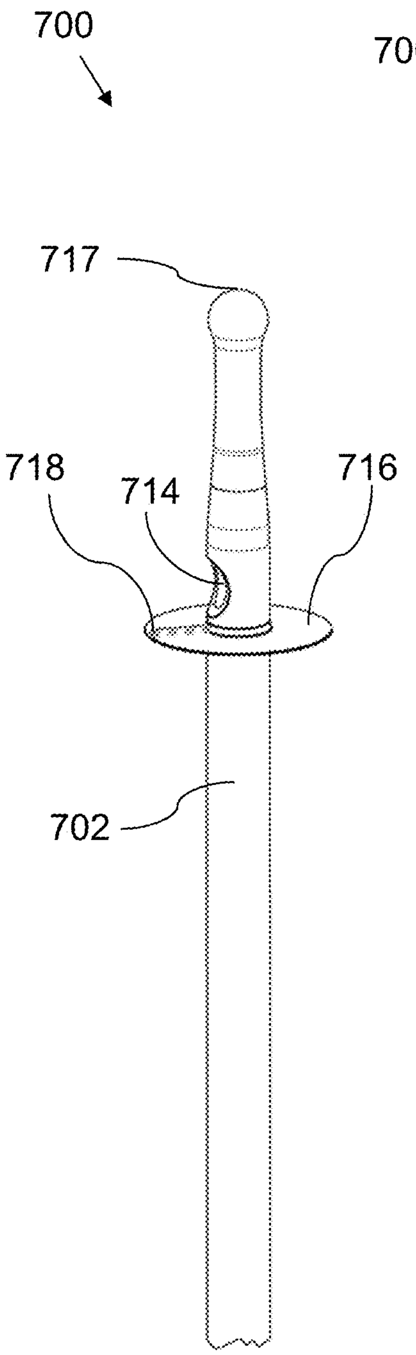
FIGS. 18*a-b* show another separate inlet protector part and an assembly process.
Figure 18B:
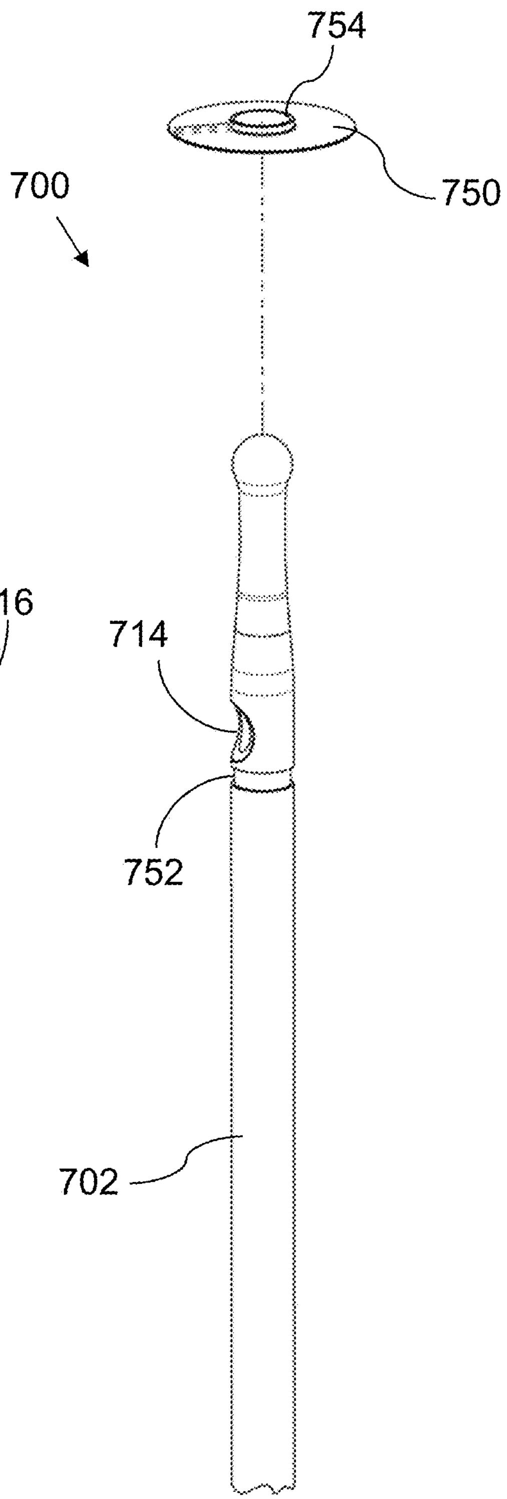

FIGS. 18*a* and 18*b* are similar to FIGS. 17*a* and 17*b*, but with a variation in how the inlet protector part 750 attaches to the rest of the catheter 700. In this embodiment the urine conduit 702 has an annular groove 752 formed in its outer circumference that is arranged to receive the inlet protector part 750. The groove 752 limits axial movement of the inlet protector part 750 once it is installed so that the inlet protector 716 remains in the correct place throughout use. The groove 752 forms a female connector part, while the inner diameter 754 of the inlet protector part 750 forms a male connector part that engages with the female connector part. It will be appreciated that these could be arranged the opposite way around, i.e. with a groove on the inside of the inlet protector part 750 and an annular ridge on the urine conduit 702.

Figure 19A:
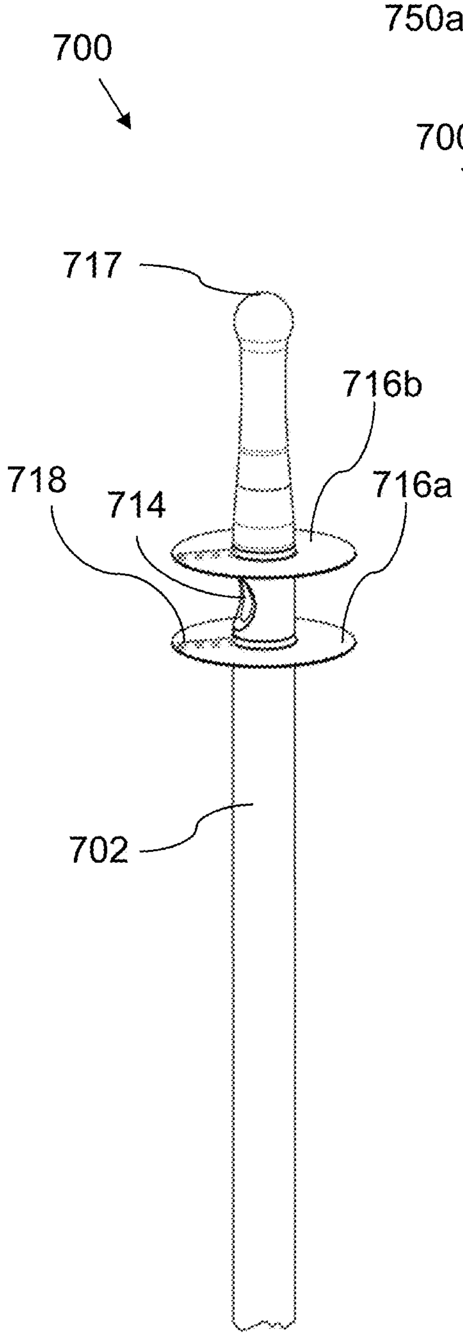
FIGS. 19*a-b* show a catheter with two inlet protectors and an assembly process.
Figure 19B:
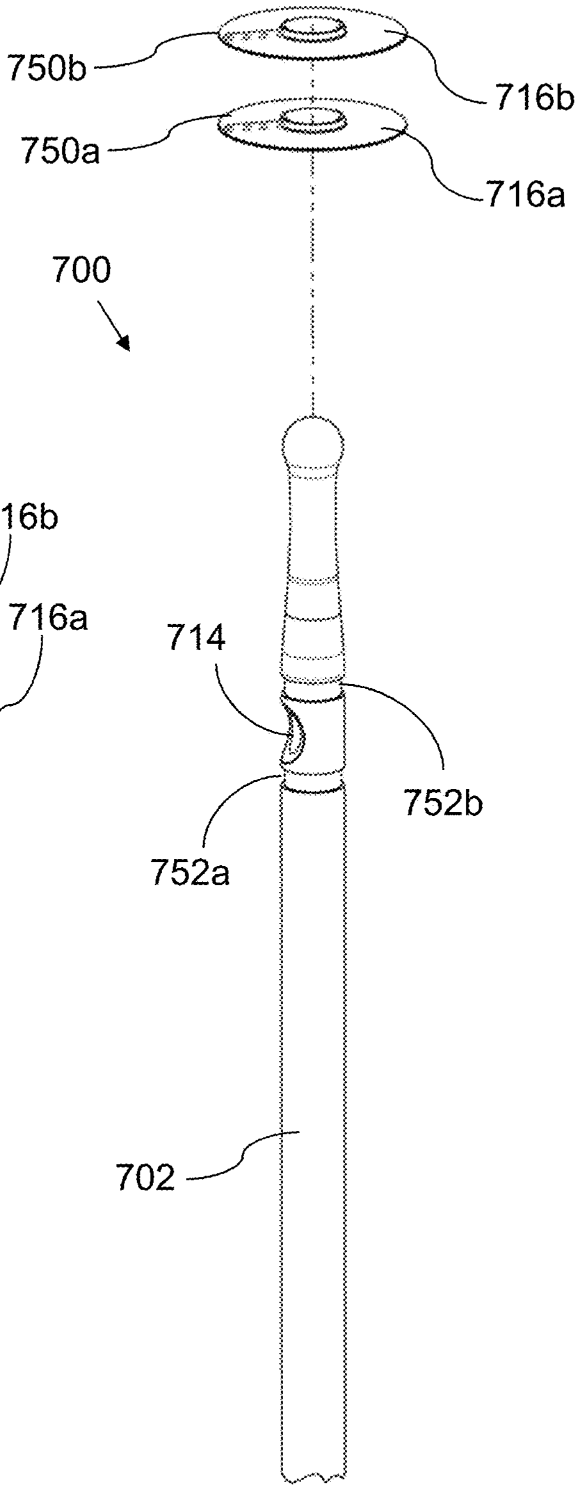

FIG. 19*a* shows a variation of a catheter 700 in which two inlet protectors 716*a* and 716*b* are provided. A first inlet protector 716*a* is essentially as described above (according to any of the various embodiments) and is located adjacent to the first urine inlet 714 such that the urine inlet 714 lies between the first inlet protector 716*a* and the proximal end 717. The second inlet protector 716*b* lies between the first urine inlet 714 and the proximal end 717. The second inlet protector 716*b* protects the first urine inlet 714 during the insertion procedure, whereas the first inlet protector 716*a* protects the first urine inlet 714 during the removal procedure. Thus the first inlet protector 716*a* folds over the inlet 714 during removal and the second inlet protector 716*b* folds over the inlet during insertion. Thus the edges of the first urine inlet 714 are separated from the tissue of the urethra and bladder during the entire passage through the urethra. FIG. 19*b* illustrates one way of mounting two inlet protectors by forming each inlet protector as an inlet protector part (a first inlet protector part 750*a* and a second inlet protector part 750*b*) which are mounted to the rest of a catheter 700 similar to the method shown in FIG. 16*b*. However, it will be appreciated that the principle can be applied for any method of providing the two inlet protectors (e.g. both may be integrally formed with a tip part in the manner described above in relation to FIGS. 14 and 15).

Figures 20A, 20B:
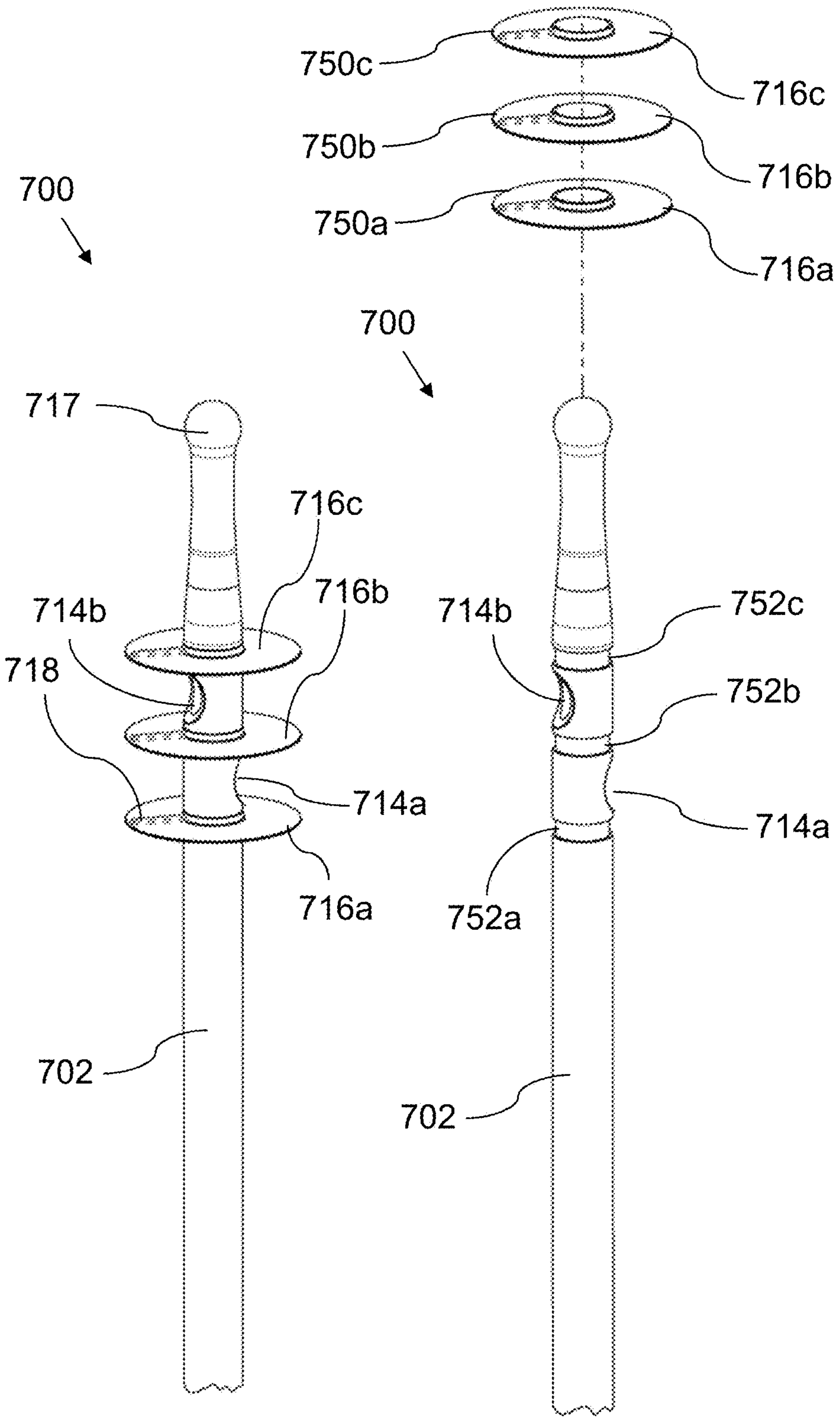
FIGS. 20*a-b* show a catheter with three inlet protectors and an assembly process.

FIGS. 20*a* and 20*b* illustrate a further development of the embodiment shown in FIGS. 19*a* and 19*b*. As shown in FIG. 20*a*, the catheter 700 in this embodiment has two urine inlets, i.e. a first urine inlet 714*a* and a second urine inlet 714*b*. The two inlets 714*a*, 714*b* are arranged at different axial positions on the catheter 700 and thus the second urine inlet 714*b* provides a backup flow path in case the first urine inlet 714*a* is blocked or is lodged in the urethra. The two urine inlets 714*a*, 714*b* also face in opposite directions in this embodiment, providing further reliability in case one side is hindered by an obstruction such as the bladder wall. As can be seen in FIG. 20*a*, three inlet protectors are provided in this embodiment, i.e. a first inlet protector 716*a*, a second (intermediate) inlet protector 716*b* and a third inlet protector 716*c*. The first and second inlet protectors are arranged as described above for FIG. 19*a*. The second urine inlet 714*b* is then arranged between the second inlet protector 716*b* and the proximal end 717 and the third inlet protector 716*c* is arranged between the second urine inlet 714*b* and the proximal end 717. Thus, during insertion, the second inlet protector 716*b* folds over the first urine inlet 714*a* and the third inlet protector 716*c* folds over the second urine inlet 714*b*. During removal, the first inlet protector 716*a* folds over the first urine inlet 714*a* and the second inlet protector 716*b* folds over the second urine inlet 714*b*. Thus both urine inlets 714*a*, 714*b* are protected during both the insertion process and the removal process. FIG. 20*b* shows one way of assembling three inlet protectors by forming each inlet protector as an inlet protector part 750*a-c* which are then mounted onto the rest of a catheter 700 as described above in relation to FIG. 16*b*, although it will be appreciated that other methods of forming or fitting the inlet protectors 716*a-c* may be used instead, e.g. integral moulding on a separate tip part as described in relation to FIGS. 14 and 15.

Figure 21B:
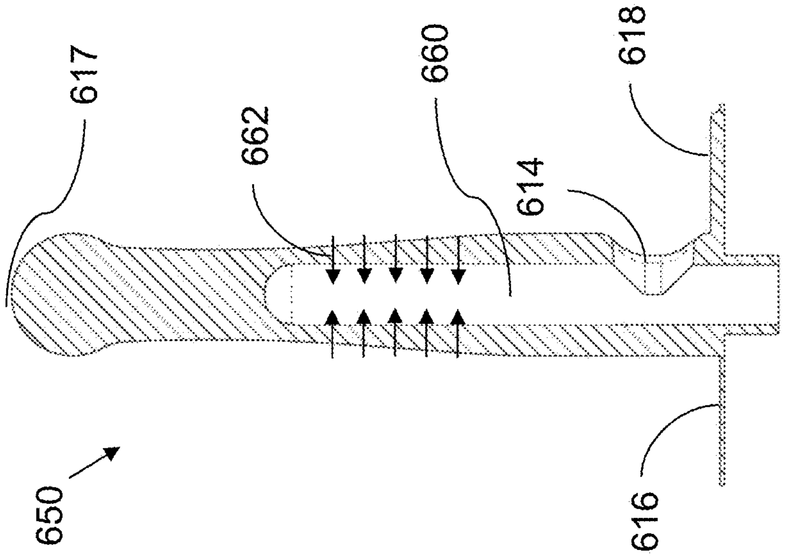
FIGS. 21*a-b* show a catheter tip part with different lengths of inner lumen.
Figure 21A:
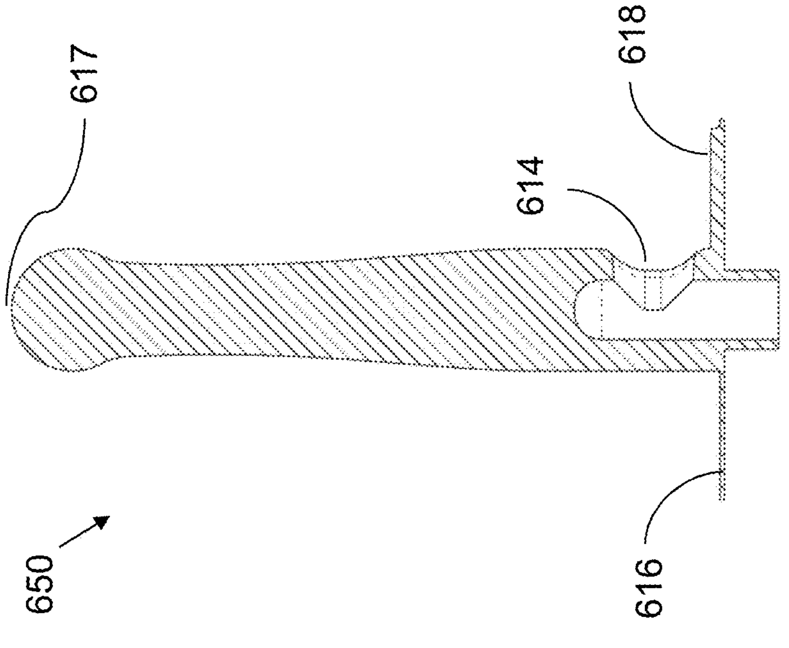

FIG. 21*a* shows a cross-section of a tip part 650 similar to that of FIG. 14*d*. FIG. 21*b* shows a cross-section of a tip part 650 similar to FIG. 21*a* but with an extended inner lumen 660 that extends through about two thirds the overall length of the tip part 650. The inner lumen provides fluid communication between the first urine inlet 614 and the distal end of the tip part 650 (for connection to the outlet tube and the urine outlet) in the same manner as in FIG. 21*a*, but additionally extends a significant distance towards the proximal end 617. It can be seen that this inner lumen 660 reduces the amount of material in the tip part 650 which increases its flexibility. In addition the tip part 650 may be provided with small urine inlets 662 with much smaller size than the first urine inlet 614 (small enough that they do not risk damage or discomfort to the user). These small urine inlets 662 provide for improved reliability of urine evacuation at multiple different insertion positions such that urine can still be drained from the bladder even if the first urine inlet 614 is blocked or lodged in the urethra.

Figure 22C:
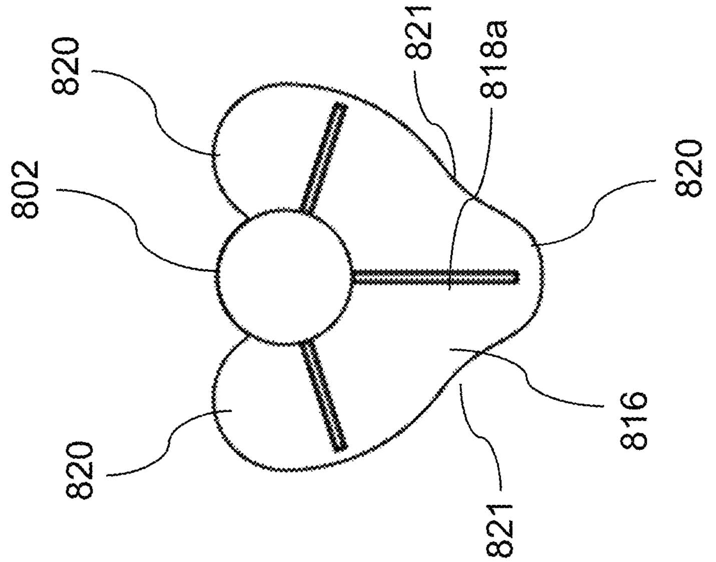
FIGS. 22*a-c* show a catheter tip part with an asymmetric inlet protector.
Figure 22B:
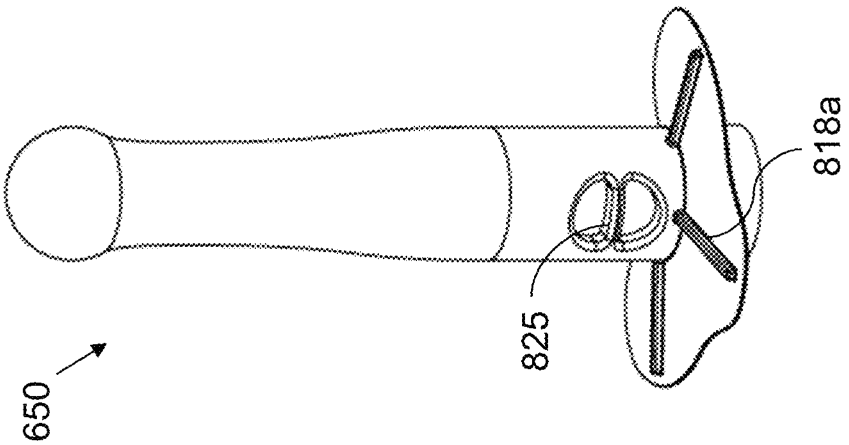
Figure 22A:
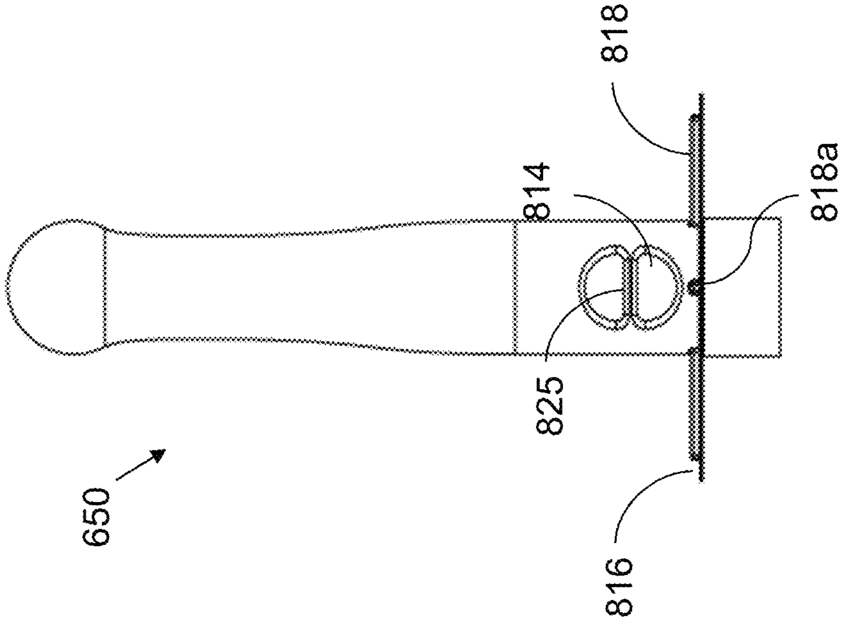

FIGS. 22*a*, 22*b* and 22*c* respectively show a side view, perspective view and plan view of a tip part 650 with an asymmetrical inlet protector 816. The asymmetrical inlet protector 816 has three radially extending ridges 818 on the surface facing the urine inlet 814. One radially extending ridge 818*a* is aligned with the urine inlet 814 so that when the inlet protector 816 folds against the urine inlet 814, it prevents full blockage of the urine inlet 814. The asymmetrical inlet protector 816 does not fully surround the urine conduit 802, but instead extends a little over 180 degrees around the urine conduit 802. This circumferential extent ensures that the inlet protector 816 is sufficiently urged from a folded configuration into a deployed configuration once it is inside the bladder. The asymmetric shape reduces the amount of material when compared with an inlet protector that extends fully around the circumference of the urine conduit 802 and thus reduces the overall diameter of the catheter when the inlet protector is in a stressed configuration. Alternatively, this shape allows more material to be used adjacent to the urine inlet 814 while maintaining a given diameter.

The asymmetric inlet protector 816 has a lobed structure, having a radius that varies with angle around the urine conduit. The inlet protector has three lobes 820, each having a local radius maximum. Between these maxima, the inlet protector has two radial minima at the points 821 between lobes 820. These local minima form indents 821 in the circumferential shape of the inlet protector 816. The minimum radius part (or the indent 821 between lobes 820) allows a reduction in material of the inlet protector 816 compared with an inlet protector without such indents. The indents 821 also encourage folding of the inlet protector 816 in a particular region when the inlet protector 816 is folded against the urine conduit 802. By encouraging folding to occur in one or more particular regions, the inlet protector 816 can ensure a good distribution of material around the urine conduit 802, thus reducing the overall diameter of the catheter during insertion and removal.

In addition to the radially extending ridge 818*a* being aligned with the urine inlet 814, FIGS. 22*a* and 22*b* show that the urine inlet 814 comprises a horizontal bar 825 which extends across the urine inlet at around its mid-height, essentially dividing the urine inlet 814 into two adjacent urine inlets. The bar 825 is arranged perpendicular to the radially extending ridge 818*a* when the ridge 818*a* is folded up against the urine inlet 814. This arrangement serves to prevent the ridge 818*a* from being sucked into the urine inlet 814, even when a high flow rate causes a high suction that pulls the inlet protector 816 into contact with the urine inlet 814. This protects against complete blockage of the urine inlet 814.

Figure 23C:
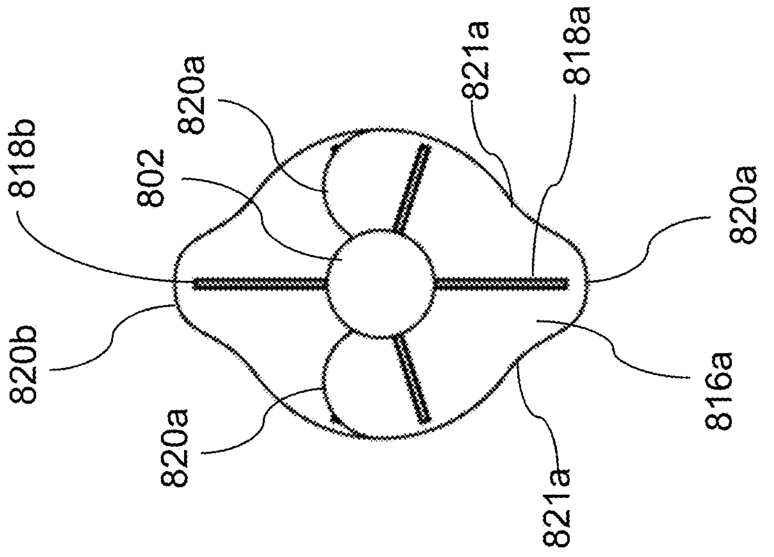
FIGS. 23*a-c* show a catheter tip part with two asymmetric inlet protectors.
Figure 23B:
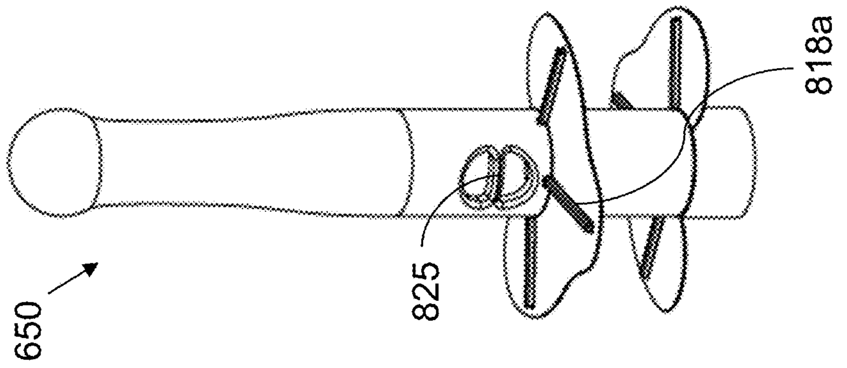
Figure 23A:
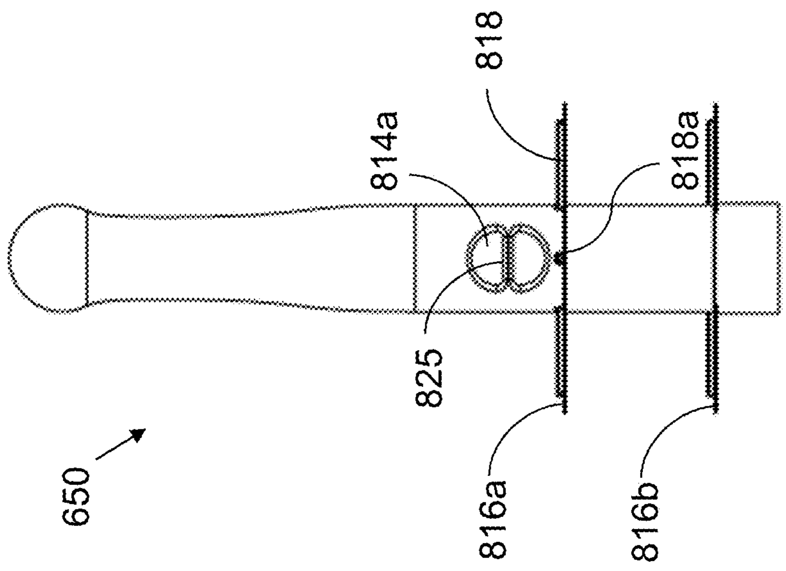

FIGS. 23*a-c* are similar to FIGS. 22*a-c* except that they show a tip part 650 with two asymmetric inlet protectors 816*a*, 816*b*. The first asymmetric inlet protector 816*a* protects the first urine inlet 814*a*. The second asymmetric inlet protector 816*b* protects the second urine inlet 814*b* (not visible in the figures) which is arranged on the opposite side of the tip part 650 and at a different axial position. The two inlet protectors 816*a*, 816*b* are substantially the same in design, but as they are arranged on opposite sides of the tip part 650, they distribute the material more evenly around the tip part 650 (and thus around the catheter as a whole), thus reducing the overall diameter at any given axial position.

Figure 24B:
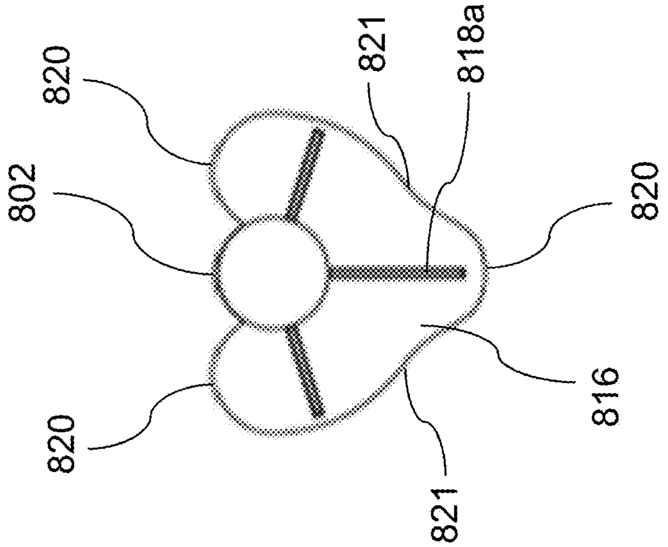
FIGS. 24*a-b* show a catheter with an asymmetric inlet protector and an anti-removal balloon.
Figure 24A:
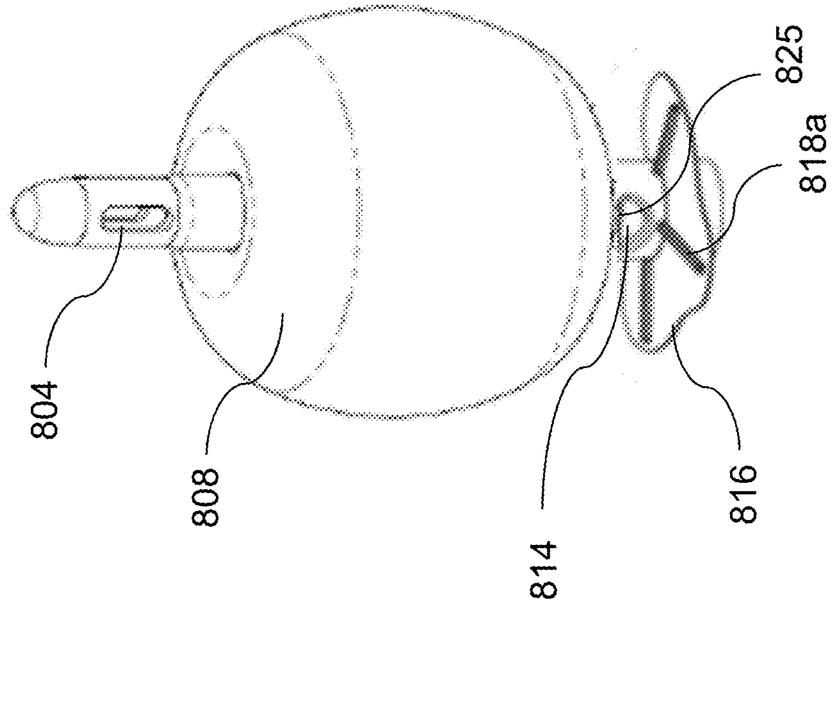

FIGS. 24*a* and 24*b* show an embodiment in which an asymmetrical inlet protector 816 and a bar 825 across the urine inlet 814 are used on a catheter together with an anti-removal balloon 808 and with a further urine inlet 802 at the tip of the catheter.

Figure 25B:
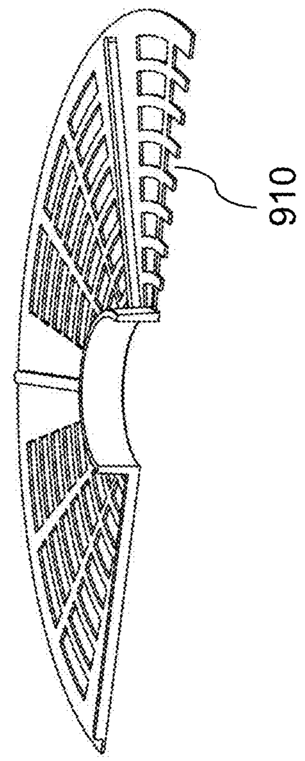
FIGS. 25*a-b* and 26*a-b* show alternative embodiments of an inlet protector.
Figure 25A:
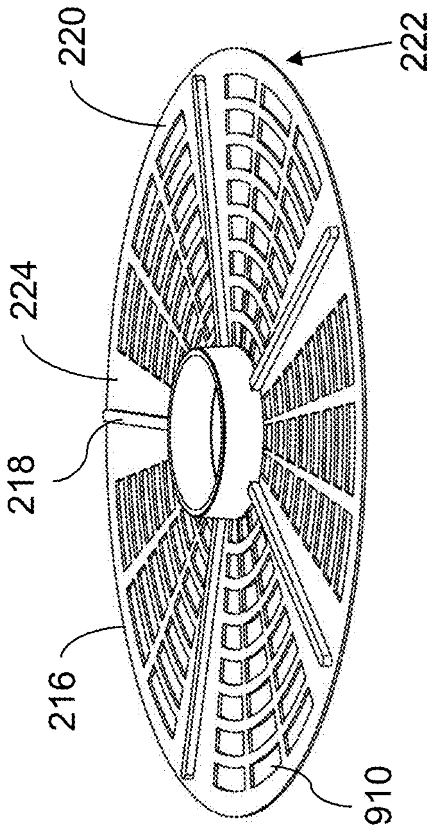

FIGS. 25*a*, 25*b*, 26*a* and 26*b* show alternative embodiments of an inlet protector 216. FIG. 25*a* shows an inlet protector 216 with five radially extending ridges 218 and with a number of holes 910 therethrough. The inlet protector 216 can fold over the urine inlet (not shown in these figures) during withdrawal of the catheter through the urethra, protecting the tissue in the urethra from any sharper edges, e.g. of the urine inlet. As described above in relation to FIG. 3, the inlet protector 216 has a first face 220 and a second face 222. The holes 910 pass through the inlet protector 216 from the first face 220 to the second face 222, thus allowing fluid to flow therethrough. In normal operation, when the catheter is correctly situated in the bladder neck, the holes 910 will be in contact with the tissue of the bladder neck and will not permit fluid to bypass the catheter. Instead, urine can be passed from the bladder through the urethra via the urine inlet. However, it is possible that the catheter may become improperly positioned during use. If it moves a short distance down into the urethra, the inlet protector 216 will fold up over the urine inlet, potentially blocking the urine inlet. However, with holes 910 provided in the inlet protector 216, at least in a position that will overlap the urine inlet when the inlet protector 216 is folded up, the urine inlet will never be completely blocked by the inlet protector 216 and can still allow urine to drain through the urine inlet, albeit at a reduced rate. This improves the safety for the user. As can be seen in FIGS. 25*a* and 25*b*, multiple holes 910 are provided in this embodiment, at positions all around the inlet protector 216. This provides a large number of potential passageways across the inlet protector (from the first face 220 to the second face 222) such that there will always be at least one such passageway, whichever way the inlet protector folds up. In other embodiments, this number of holes 910 may not be necessary. Instead, a single hole 910 may be provided in a region aligned with a urine inlet when folded up. Where several urine inlets are provided, at least one hole 910 may be provided for each urine inlet.

In FIGS. 25*a* and 25*b*, the holes 910 are arc shaped and arranged along arcs centred on the centre of the inlet protector 216. The holes that are radially further from the centre are larger in arc length and larger in area.

Figure 26B:
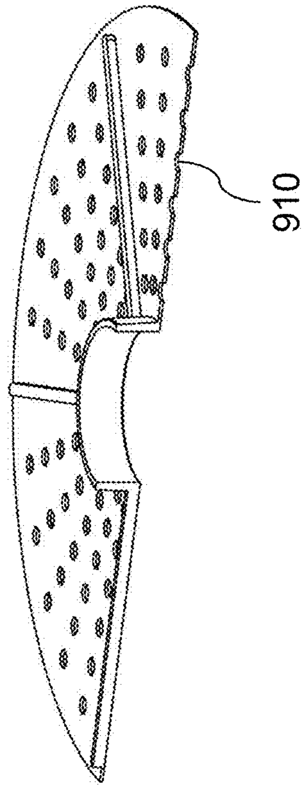
Figure 26A:
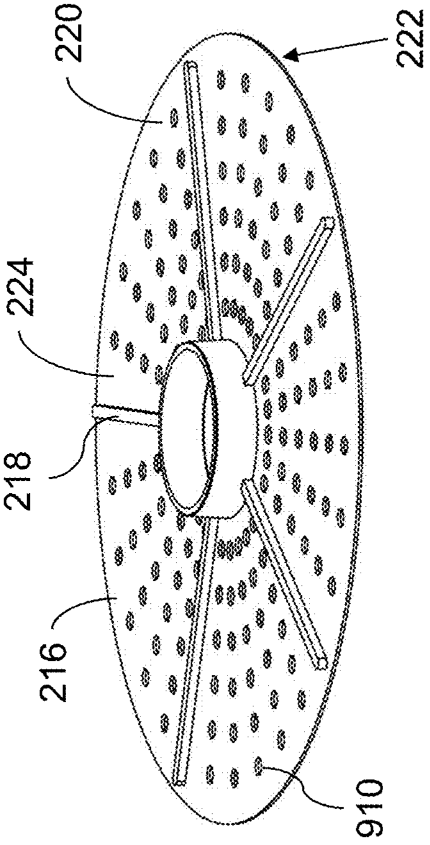

FIGS. 26*a* and 26*b* are similar to FIGS. 25*a* and 25*b*, but the holes 910 are smaller and are circular. The holes 910 in FIGS. 26*a* and 26*b* are arranged along radial lines from the centre of the inlet protector 216 and each hole 910 has the same area. The holes 910 in the embodiment shown in FIGS. 26*a* and 26*b* are less than 0.4 mm in diameter. These holes 910 are small enough that they do not permit any significant leakage through the inlet protector 216, but they will still allow urine to pass through the inlet protector 216 when there is a pressure difference across the inlet protector 216 (e.g. if the inlet protector 216 is folded up against the urine inlet).

Figure 27A:
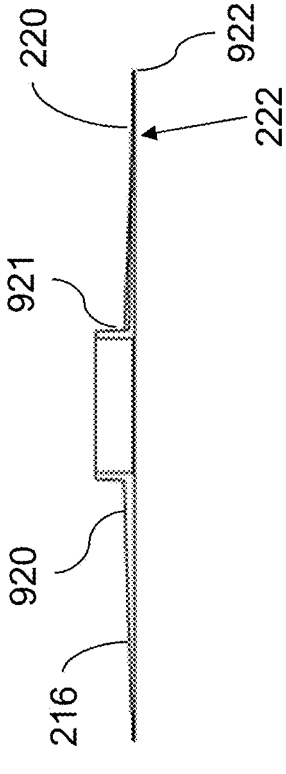
FIGS. 27*a-d* and 28*a-d* show further embodiments of an inlet protector.
Figure 27B:
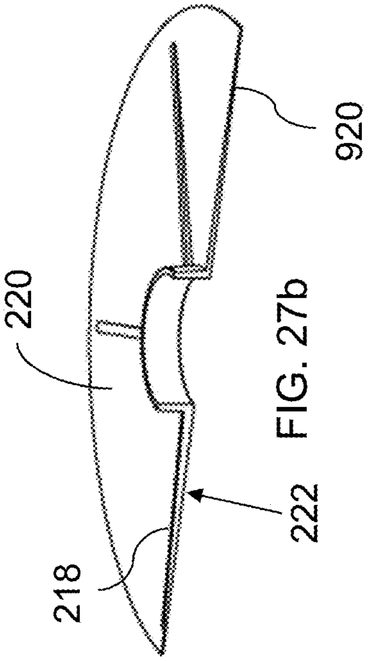
Figure 27C:
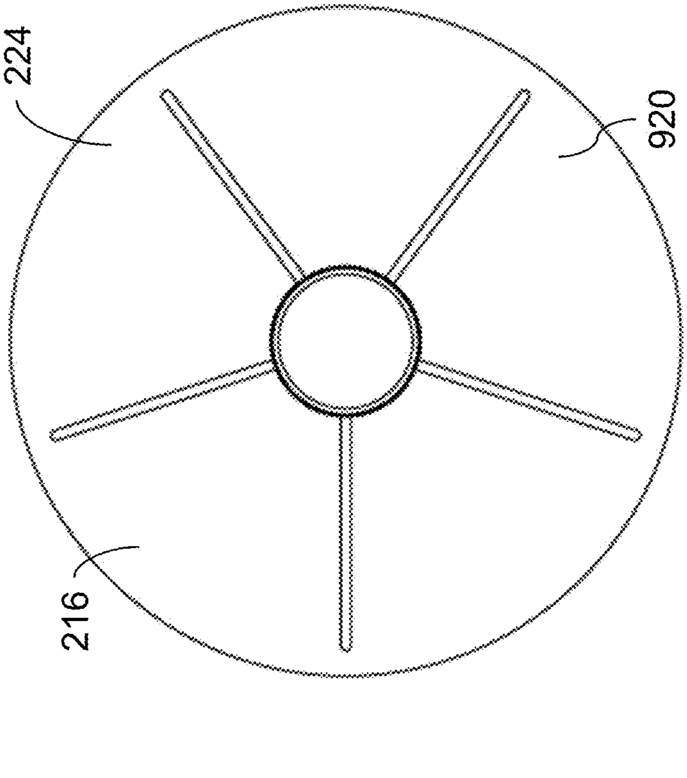
Figure 27D:
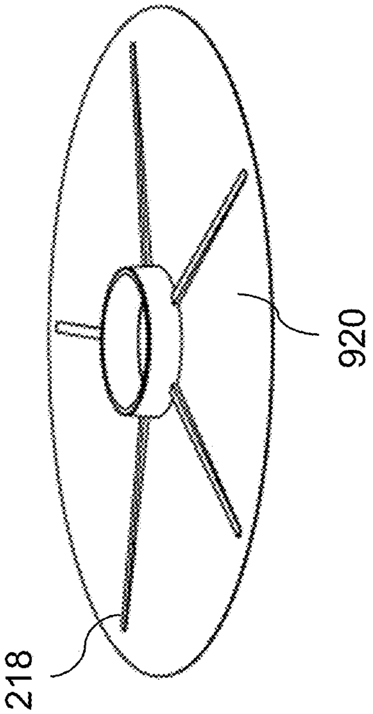

FIGS. 27*a-d* show further embodiments of an inlet protector 216. FIG. 27*a* is a section view, FIG. 27*b* is a perspective view showing the section of FIG. 27*a*. FIG. 27*c* is a plan view and FIG. 27*d* is a perspective view of the whole inlet protector 216. The inlet protector 216 in this example has five radially extending ridges 218, with a comparatively thinner web of material 224 extending between the ridges 218. As can be seen in FIG. 27*a*, the inlet protector has a tapered section 920 which reduces in thickness between its radially inner edge 921 and its radially outer edge 922. The reduction in thickness is achieved via a smooth taper from the inlet protector's radially inner edge 921 to the inlet protector's radially outer edge 922. The taper reduces the volume of material in the outer parts of the inlet protector. The outer parts of the inlet protector experience more folding (e.g. overlapping) when the inlet protector is folded up against the urine conduit 202 (as shown in FIG. 4*c*) or over the urine inlet (as shown in FIG. 4*d*). For example, to reduce the outer circumference of the inlet protector 216 down to the outer circumference of the urine conduit 202, the inlet protector 216 must become folded over itself. As the wider parts of the inlet protector 216 (with the greatest radius) are thinner, these folded sections have a reduced thickness and the overlaps (whether these are overlaps just of the thin webbing part 224 with itself or overlaps of the webbing 224 with ridges 218) are correspondingly thinner. Thus, in the folded state, the catheter overall has a smaller diameter which is easier and more comfortable to insert and remove through the urethra. The thicker parts of the inlet protector 216 at the radially inner side provide the required stiffness to ensure that the inlet protector unfolds when the catheter is deployed and resists folding up in normal use (e.g. so that the catheter is located correctly in the urethral neck). As shown in FIGS. 27*a-d*, the five radially extending ridges 218 are also tapered so that they reduce in thickness between the radially inner edge 921 and radially outward edge 922. The tapering of the radially extending ridges 218 matches the tapering of the thinner web 224 between ridges 218, i.e. the ridges 218 always have the same height above the thinner material 224.

Figure 28B:
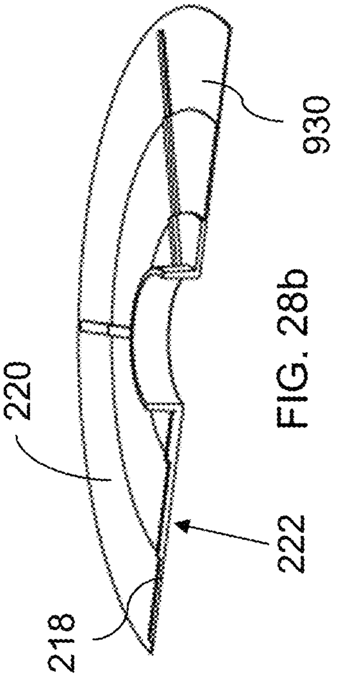
Figure 28D:
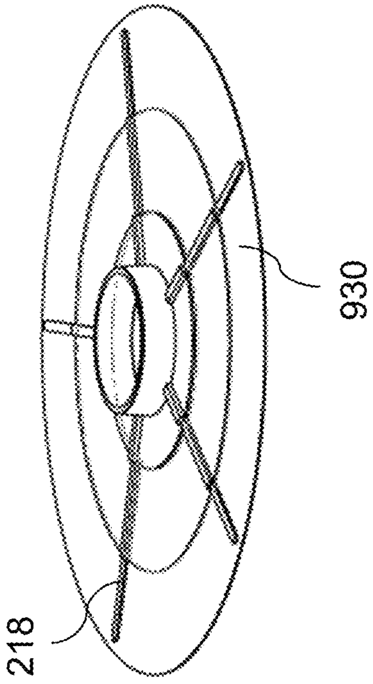
Figure 28A:
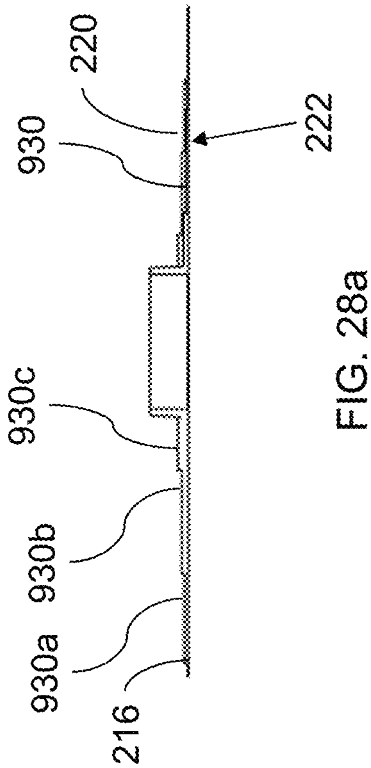
Figure 28C:
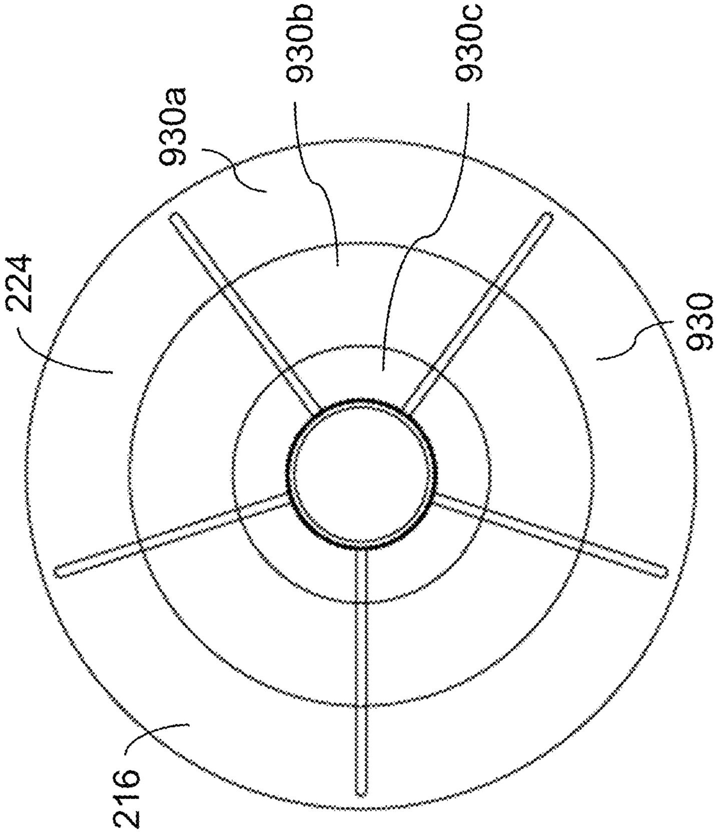

FIGS. 28*a-d* are similar to FIGS. 27*a-d*, but instead of a smooth taper, the inlet protector 216 has a stepped taper. The stepped tapered section 930 in this embodiment comprises three sections of different thicknesses 930*a*, 930*b*, 930*c* and thus the inlet protector 216 includes two step reductions in thickness between these three sections. Each step reduction takes place at a particular radius so that each of the three sections 930*a*, 930*b*, 930*c* is a ring of constant thickness. As can be seen in FIG. 28*a*, the five radially extending ridges 218 are also stepped down in thickness in the same manner (and with the step reductions taking place at the same radii as for the thinner material 224).

It will be appreciated that, although the tapering of FIGS. 27 and 28 is shown in isolation and the perforations of FIGS. 25 and 26 are shown in isolation, these features can be combined in any combination. Additionally, each (or both) of these features can be combined with the other features described elsewhere and in relation to the other figures.

It will be appreciated by those skilled in the art that the invention has been illustrated by describing one or more specific embodiments thereof, but is not limited to these embodiments; many variations and modifications are possible, within the scope of the accompanying claims.

Certain specific embodiments of the invention will now be set out by way of example:

Embodiment 1. A catheter insertable into a urethra for installation in a user's bladder and urethra, the catheter comprising:

- a urine conduit comprising a first urine inlet and a urine outlet; and
- an inlet protector extending outwardly from the urine conduit from a position between the first urine inlet and the urine outlet.

Embodiment 2. A catheter as set out in embodiment 1, wherein the inlet protector is located substantially adjacent to the first urine inlet such that, in use, the first urine inlet is located near to the urethral neck.

Embodiment 3. A catheter as set out in embodiment 1 or 2, wherein the inlet protector is foldable such that it axially overlaps the first urine inlet.

Embodiment 4. A catheter as set out in any preceding embodiment, wherein the urine conduit has a substantially circular cross-section and the proximal end of the urine conduit has a rounded shape.

Embodiment 5. A catheter as set out in any preceding embodiment, wherein the inlet protector is arranged to contact the bladder wall if the catheter moves in the direction of removal from the urethra.

Embodiment 6. A catheter as set out in any preceding embodiment, wherein the inlet protector and the urine conduit are integrally moulded.

Embodiment 7. A catheter as set out in any preceding embodiment, wherein the inlet protector is arranged to be movable between a covering position in which it covers the first urine inlet and an open position in which it does not cover the first urine inlet.

Embodiment 8. A catheter as set out in any preceding embodiment, wherein the inlet protector comprises a skirt, disc, plate or dish.

Embodiment 9. A catheter as set out in embodiment 8, wherein the inlet protector comprises a resilient skirt, resilient disc, resilient plate or resilient dish.

Embodiment 10. A catheter as set out in any preceding embodiment, wherein the inlet protector comprises a plurality of radially extending ridges having a portion of material extending therebetween, each of the radially extending ridges having a greater thickness than the material extending therebetween.

Embodiment 11. A catheter as set out in embodiment 10, wherein the ridges and the material extending therebetween are integrally moulded.

Embodiment 12. A catheter as set out in embodiment 10 or 11, wherein the outer ends of the radially extending ridges taper in thickness from their thickest points to the thickness of the material extending therebetween.

Embodiment 13. A catheter as set out in any of embodiments 10 to 12, wherein each of the radially extending ridges has a thickness at its thickest point that is two to ten times greater than a thickness of the material extending therebetween.

Embodiment 14. A catheter as set out in any of embodiments 10 to 13, wherein the inlet protector, when in a non-stressed position, comprises a first face which is substantially smooth and a second face comprising the radially extending ridges protruding therefrom, the first face facing away from the first urine inlet and the second face facing towards the first urine inlet.

Embodiment 15. A catheter as set out in any preceding embodiment, wherein the inlet protector comprises at least one radially extending ridge positioned adjacent to the first urine inlet.

Embodiment 16. A catheter as set out in any preceding embodiment wherein the inlet protector, when in a non-stressed position, is substantially planar.

Embodiment 17. A catheter as set out in any preceding embodiment, wherein the inlet protector permits folding towards the first urine inlet, and permits folding towards the urine outlet, so as to conform to the shape of the exterior surface of the urine conduit.

Embodiment 18. A catheter as set out in any preceding embodiment, wherein the inlet protector is arranged to fold into a substantially tube-shaped configuration wrapping around the urine conduit in a direction towards the urine outlet during insertion of the catheter into a urethra, and to fold into a substantially tube-shaped configuration wrapping around the urine conduit in a direction towards the first urine inlet during removal of the catheter through the urethra.

Embodiment 19. A catheter as set out in any preceding embodiment, wherein the inlet protector is arranged, in use, to permit folding into a substantially truncated-cone-shaped configuration located at least partially in a urethral neck, with the base of the truncated-cone shape facing towards the bladder.

Embodiment 20. A catheter as set out in any preceding embodiment, wherein the inlet protector reduces in thickness between its radially inner edge and its radially outer edge.

Embodiment 21. A catheter as set out in embodiment 20, wherein the reduction in thickness forms a smooth taper or a stepped taper.

Embodiment. A catheter as set out in embodiment 20 or 21 and as set out in any of embodiments 10 to 15, wherein each radially extending ridge reduces in thickness between its radially inner edge and its radially outer edge.

Embodiment 23. A catheter as set out in any preceding embodiment, wherein the inlet protector comprises one or more holes therethrough.

Embodiment 24. A catheter as set out in embodiment 23, wherein at least one hole through the inlet protector is located such that when the inlet protector is folded against the urine inlet, the hole overlaps at least partially with the urine inlet.

Embodiment 25. A catheter as set out in embodiment 23 or 24, wherein the hole through the inlet protector is no more than 0.5 mm in diameter.

Embodiment 26. A catheter as set out in any preceding embodiment, wherein the inlet protector is asymmetrical about the urine conduit.

Embodiment 27. A catheter as set out in embodiment 26, wherein the inlet protector extends further in a radially outward direction on one side than the opposite side of the urine conduit.

Embodiment 28. A catheter as set out in embodiment 27, wherein the inlet protector extends at least 120 degrees, at least 150 degrees or at least 180 degrees around the circumference of the urine conduit.

Embodiment 29. A catheter as set out in any preceding embodiment, wherein the inlet protector has a lobed structure, having a radius that varies with angle around the urine conduit, the inlet protector having at least one minimum radius located between two maximum radii.

Embodiment 30. A catheter as set out in embodiment 29, wherein at least one maximum radius is aligned with the urine inlet.

Embodiment 31. A catheter as set out in any preceding embodiment, wherein the shape of the urine inlet includes a blocking structure to block entry of the inlet protector.

Embodiment 32. A catheter as set out in embodiment 31, wherein the blocking structure comprises a bar extending across the urine inlet.

Embodiment 33. A catheter as set out in embodiment 32, wherein the bar extends substantially perpendicular to a radially extending ridge on the inlet protector.

Embodiment 34. A catheter as set out in any preceding embodiment, wherein the inlet protector is an expandable structure which can be adjusted between a first configuration in which the inlet protector is foldable against the urine conduit and a second configuration in which the inlet protector projects away from the urine conduit.

Embodiment 35. A catheter as set out in any preceding embodiment, wherein the inlet protector is formed on a separate inlet protector part that is attached to the urine conduit.

Embodiment 36. A catheter as set out in embodiment 35, wherein the inlet protector part is attached to the urine conduit by an interlocking arrangement.

Embodiment 37. A catheter as set out in embodiment 36, wherein the interlocking arrangement comprises a male or female interlocking structure on the urine conduit and a corresponding female or male interlocking structure on the inlet protector part.

Embodiment 38. A catheter as set out in embodiment 37, wherein the inlet protector part comprises a projection and the urine conduit comprises a recess which is adapted to engage with the projection.

Embodiment 39. A catheter as set out in any of embodiments 35 to 38, wherein the inlet protector part comprises an inner ring structure of a higher rigidity than the inlet protector.

Embodiment 40. A catheter as set out in any preceding embodiment, wherein the inlet protector is integrally formed with a tip part of the catheter, the tip part being attachable to an outlet tube to form the urine conduit.

Embodiment 41. A catheter as set out in embodiment 40, wherein the first urine inlet is integrally formed in the tip part such that when the tip part is attached to the outlet tube, the first urine inlet is in fluid communication with the urine outlet.

Embodiment 42. A catheter as set out in embodiment 40 or 41, wherein the edges of the first urine inlet are formed with a radius that is at least 0.3 mm, at least 0.4 mm, at least 0.5 mm or at least 0.6 mm.

Embodiment 43. A catheter as set out in embodiment 40, 41 or 42, wherein the tip part is adapted to be mounted to the outlet tube with an interference fit.

Embodiment 44. A catheter as set out in any of embodiments 40 to 43, wherein at least one of the parts comprises one or more projections arranged to project towards and into the other part when engaged.

Embodiment 45. A catheter as set out in any of embodiments 40 to 44, wherein a rigid connection piece is provided in a region of the tip part which engages with the outlet tube, when the tip part is attached to the outlet tube, wherein said region is formed from a first material of a first hardness, and the remainder of the tip part is formed over/around the rigid connection piece from a second material of a second hardness which is lower than the first hardness.

Embodiment 46. A catheter as set out in any of embodiments 40 to 45, wherein the tip part comprises an inner lumen extending along at least 50, at least 60 or at least 70 percent of its length.

Embodiment 47. A catheter as set out in embodiment 46, wherein the tip part comprises up to 100 small urine inlets, preferably wherein the diameter of such small urine inlets is smaller than the first urine inlet, more preferably wherein such small urine inlets are formed with a largest dimension less than 1 mm and/or with an area less than 1 mm 2.

Embodiment 48. A catheter as set out in any preceding embodiment, comprising a first and a second urine inlet, wherein at least one inlet protector is located between the first urine inlet and a second urine inlet and is arranged to fold over one urine inlet during insertion and is arranged to fold over the other urine inlet during removal.

Embodiment 49. A catheter as set out in any preceding embodiment, comprising a first and a second urine inlet and a first and second inlet protector, wherein the first urine inlet is located between the first inlet protector and the second inlet protector and the second urine inlet is located between the second inlet protector and the proximal end of the catheter.

Embodiment 50. A catheter as set out in any preceding embodiment, comprising a first and a second urine inlet and a first, second and third inlet protector, wherein the first urine inlet is located between the first inlet protector and the second inlet protector and the second urine inlet is located between the second inlet protector and the third inlet protector.

Embodiment 51. A catheter as set out in any preceding embodiment further comprising an anti-removal structure located on the opposite side of the first urine inlet to the inlet protector, the anti-removal structure being adjustable between a first configuration in which the anti-removal structure permits removal of the catheter through the urethra, and a second configuration in which the anti-removal structure prevents removal of the catheter through the urethra.

Embodiment 52. A catheter as set out in embodiment 51, wherein the anti-removal structure is located close to the inlet protector such that when the anti-removal structure contacts the urethral neck, when in the second configuration, the inlet protector is arranged to push against the urethral neck so as to cause the catheter to move back in the direction towards the bladder.

Embodiment 53. A catheter as set out in embodiment 51 or 52, wherein the longitudinal separation between the anti-removal structure when in the second configuration and the inlet protector when in a non-stressed position is less than the maximum lateral separation between an edge of the inlet protector and an exterior surface of the urine conduit.

Embodiment 54. A catheter as set out in embodiment 51 or 52, wherein the longitudinal separation between the anti-removal structure when in the second configuration and the inlet protector when in a non-stressed position is greater than the maximum lateral separation between an edge of the inlet protector and an exterior surface of the urine conduit.

Embodiment 55. A catheter as set out in any of embodiments 51 to 54, wherein the anti-removal structure comprises a positioning balloon, the positioning balloon being adjustable between a contracted configuration in which the positioning balloon permits removal of the catheter through the urethra and an expanded configuration in which the positioning balloon prevents removal of the catheter through the urethra.

Embodiment 56. A catheter as set out in embodiment 55 comprising a fluid supply conduit through which fluid can be inserted and/or removed from the positioning balloon.

Embodiment 57. A catheter as set out in embodiment 56, further comprising a valve operable to prevent fluid from passing through the opening of the fluid supply conduit when in a first configuration, and to allow fluid to pass through the opening of the fluid supply conduit when in a second configuration.

Embodiment 58. A catheter as set out in any of embodiments 51 to 57, wherein the urine conduit further comprises a second urine inlet positioned further away from the urine outlet than the first urine outlet, and wherein the anti-removal structure is positioned between the first urine inlet and the second urine inlet.

Embodiment 59. A catheter as set out in any of embodiments 51 to 58, further comprising at least one strap or brace extending over the positioning balloon.

Embodiment 60. A catheter as set out in embodiment 59, wherein the at least one strap or brace provides the inlet protector.

Embodiment 61. A catheter as set out in embodiment 59 or 60, wherein the at least one strap or brace attaches to the urine conduit at an upper attachment point near the proximal end of the catheter.

Embodiment 62. A catheter as set out in embodiment 61, wherein a second urine inlet is formed in the urine conduit between the upper attachment point and the positioning balloon.

Embodiment 63. A catheter as set out in any of embodiments 59 to 60, wherein the catheter comprises a plurality of straps or braces and a webbing extends between said straps or braces.

Embodiment 64. A catheter as set out in any preceding embodiment further comprising a fluid-based actuator, the fluid-based actuator comprising an expandable chamber, the fluid-based actuator being adjustable between a contracted configuration in which the expandable chamber contains a first volume of fluid and an expanded configuration in which the expandable chamber contains a second volume of fluid, the second volume being greater than the first volume; wherein:

when the fluid-based actuator is in one of the contracted and the expanded configurations, urine is able to flow from the urine inlet(s) to the urine outlet; and when the fluid-based actuator is in the other of the contracted and the expanded configurations, urine is prevented from flowing from the urine inlet(s) to the urine outlet.

Embodiment 65. A catheter as set out in embodiment 64 comprising an actuation conduit through which fluid may be forced into the expandable chamber of the fluid-based actuator, and through which fluid may be removed from the chamber of the fluid-based actuator.

Embodiment 66. A catheter as set out in embodiment 65, wherein the actuation conduit extends through the urine conduit to a location outside the body when the catheter is installed in a user.

Embodiment 67. A catheter as set out embodiment 65 or 66, wherein the actuation conduit extends at least partially through the expandable chamber of the fluid-based actuator.

Embodiment 68. A catheter as set out in any of embodiments 65 to 67, wherein the actuation conduit is fixed to a proximal end of the catheter.

Embodiment 69. A catheter as set out in any of embodiments 65 to 68, comprising a manually operable valve operable between a first configuration in which fluid is prevented from exiting the expandable chamber of the fluid-based actuator, and a second configuration in which fluid is able to exit the expandable chamber of the fluid-based actuator.

Embodiment 70. A catheter as set out in any of embodiments 65 to 69 comprising a manually operable pump for forcing liquid through the actuation conduit into the fluid-based actuator, the pump being located outside the body when the catheter is installed in a user.

Embodiment 71. A catheter as set out in embodiment 70, wherein the pump is arranged to force enough fluid into the fluid-based actuator to change it from the contracted configuration to the expanded configuration with a single actuation thereof.

Embodiment 72. A catheter as set out in any of embodiments 64 to 71, wherein the expandable chamber comprises an actuation balloon located in the flow path between the urine inlet(s) and the urine outlet.

Embodiment 73. A catheter as set out in embodiment 72, wherein the actuation balloon is arranged to:

abut the first urine inlet when in the expanded configuration thereby preventing urine from entering the urine conduit therethrough; and contract away from the first urine inlet when in the contracted configuration thereby allowing urine to enter the urine conduit through the first urine inlet.

Embodiment 74. A catheter as set out in embodiment 72 or 73, wherein the first urine inlet comprises one or more holes formed in a side wall of the urine conduit, and the actuation balloon is arranged to abut a peripheral wall of each of said holes when in the expanded configuration thereby preventing urine from entering the urine conduit therethrough.

Embodiment 75. A catheter as set out in embodiment 74, wherein the actuation balloon is arranged to protrude into each of said holes when in the expanded configuration so as to form a seal with the peripheral wall of each hole.

Embodiment 76. A catheter as set out in any of embodiments 72 to 75, wherein the actuation balloon is arranged to abut an internal wall of the urine conduit between the urine inlet(s) and the urine outlet when in the expanded configuration so as to prevent urine from flowing from the urine inlet(s) to the urine outlet through the urine conduit.

Embodiment 77. A catheter as set out in any of embodiments 72 to 76, wherein the urine conduit comprises a constricted portion located between the first urine inlet and the urine outlet, and the actuation balloon is arranged to abut an inner surface of the constricted portion of the urine conduit when in the expanded configuration so as to prevent urine from flowing from the urine inlet(s) to the urine outlet through the urine conduit.

Embodiment 78. A catheter as set out in embodiment 77, wherein the actuation balloon is arranged to protrude into the constricted portion of the urine conduit when in the expanded configuration so as to form a seal with the inner surface of the constricted portion.

Embodiment 79. A catheter as set out in any of embodiments 72 to 78, wherein:

the actuation balloon has a substantially toroidal shape having a central opening extending along a longitudinal axis of the catheter; and the actuation conduit at least partially extends through the central opening.

Embodiment 80. A catheter as set out in any preceding embodiment, wherein the proximal end of the urine conduit comprises a hole sized to accommodate insertion of instruments therethrough.

Embodiment 81. A catheter as set out in any preceding embodiment, wherein the inlet protector is foldable such that it axially overlaps the first urine inlet and the urine outlet.

Embodiment 82. A catheter insertable into a urethra for installation in a user's bladder and urethra, the catheter comprising:

a urine conduit comprising a first urine inlet and a urine outlet;

a first positioning structure arranged, in use, to inhibit removal of the catheter through the urethra.

a second positioning structure adjustable from a first configuration in which it does not significantly inhibit removal of the catheter through the urethra and a second configuration in which it prevents removal of the catheter through the urethra;

wherein:

the first positioning structure is positioned between the first urine inlet and the urine outlet; and the first urine inlet is positioned between the second positioning structure and the first positioning structure.

Embodiment 83. A catheter as set out in embodiment 82, comprising a second urine inlet, wherein the second positioning structure is positioned between the second urine inlet and the first urine inlet.

Embodiment 84. A catheter insertable into a urethra for installation in a user's bladder and urethra, the catheter comprising:

a urine conduit comprising a urine inlet;

an anti-removal structure adjustable between a first configuration in which the anti-removal structure permits removal of the catheter through the urethra and a second configuration in which the anti-removal structure prevents removal of the catheter through the urethra; and at least one strap extending from the anti-removal structure to an upper attachment point on the urine conduit;

wherein the urine inlet is located between the upper attachment point and the anti-removal structure.

Embodiment 85. A catheter insertable into a urethra for installation in a user's bladder and urethra, the catheter comprising:

a urine conduit comprising a first urine inlet and a urine outlet; and an inlet protector extending outwardly from the urine conduit from a position between the first urine inlet and proximal end of the catheter.

Embodiment 86. A catheter as set out in embodiment 84, wherein the inlet protector is arranged to at least partially overlap the inlet hole during insertion.

Embodiment 87. A method of making a catheter as set out in any preceding embodiment comprising assembling an inlet protector part to a urine conduit part such that the inlet protector part is located adjacent to the first urine inlet.

Embodiment 88. A method of making a catheter comprising assembling an inlet protector part to a urine conduit part such that the inlet protector part is located adjacent to a first urine inlet of the urine conduit part.

Embodiment 89. A tip for a catheter, the tip comprising an integral inlet protector.

Embodiment 90. A tip as set out in embodiment 89, further comprising an integral urine inlet.

Embodiment 91. A tip as set out in embodiment 90, wherein the urine inlet is located between the inlet protector and a first end of the tip Embodiment 92. A tip as set out in embodiment 91, wherein the tip is arranged to provide a fluid communication channel to a second, opposite end of the tip.

Embodiment 93. A method of making a tip for a catheter as set out in any of embodiments 89 to 92, comprising moulding such tip as one piece.

Embodiment 94. A method of making a tip for a catheter, comprising moulding as one piece, a tip having an inlet protector.

The invention claimed is:

1. An intermittent catheter insertable into a urethra for installation in a user's bladder and urethra, the catheter comprising:

a urine conduit comprising a first urine inlet and a urine outlet; and an inlet protector extending outwardly from the urine conduit from a position between the first urine inlet and the urine outlet and being located substantially adjacent to the first urine inlet;

wherein the inlet protector comprises a resilient skirt, resilient disk, resilient plate or resilient dish and wherein the inlet protector permits folding towards the first urine inlet; and permits folding towards the urine outlet, so as to conform the shape of the exterior surface of the urine conduit; and wherein the catheter does not comprise an anti-removal structure comprising a positioning balloon located on the opposite side of the first urine inlet from the inlet protector.

2. The intermittent catheter as claimed in claim 1, wherein the inlet protector, when in a non-stressed position, comprises a first face which is substantially smooth and a second face which comprises a plurality of radially extending ridges protruding therefrom, the first face facing away from the first urine inlet and the second face facing towards the first urine inlet.

3. The intermittent catheter as claimed in claim 2, wherein the inlet protector comprises at least one radially extending ridge positioned adjacent to the first urine inlet.

4. The intermittent catheter as claimed in claim 1, wherein the inlet protector is formed on a separate inlet protector part that is attached the urine conduit.

5. The intermittent catheter as claimed in claim 1, wherein the inlet protector is integrally formed with a tip part of the catheter, the tip part being attachable to an outlet tube to form the urine conduit.

6. The intermittent catheter as claimed in claim 5, wherein the tip part is moulded as a single piece and includes the inlet protector and the first urine inlet.

7. The intermittent catheter as claimed in claim 1, wherein the inlet protector is arranged to fold into a substantially tube-shaped configuration wrapping around the urine conduit in a direction towards the urine outlet during insertion of the catheter into the urethra, and to fold into a substantially tube-shaped configuration wrapping around the urine conduit in a direction towards the first urine inlet during removal of the catheter through the urethra.

8. The intermittent catheter as claimed in claim 1, wherein urine conduit comprises a side wall and the first urine inlet comprises a plurality of holes formed in said side wall.

9. The intermittent catheter as claimed in claim 8, wherein the plurality of holes are located at substantially the same longitudinal position along the urine conduit.

10. The intermittent catheter as claimed in claim 6, wherein an edge of the first urine inlet is formed with a radius that is at least 0.3 mm or at least 0.4 mm or at least 0.5 mm or at least 0.6 mm.

11. The intermittent catheter as claimed in claim 5, wherein the tip part is rounded.

12. The intermittent catheter as claimed in claim 5, wherein the tip part is affixed to the outlet tube in a manner such that it forms and retains a fluid communication between the first urine inlet and the urine outlet.

13. The intermittent catheter as claimed in claim 2, wherein the inlet protector is integrally formed with a tip part of the catheter, the tip part being attachable to an outlet tube to form the urine conduit.

14. The intermittent catheter as claimed in claim 13, wherein the tip part is moulded as a single piece and includes the inlet protector and the first urine inlet.

15. The intermittent catheter as claimed in claim 2, wherein the inlet protector is arranged to fold into a substantially tube-shaped configuration wrapping around the urine conduit in a direction towards the urine outlet during insertion of the catheter into the urethra, and to fold into a substantially tube-shaped configuration wrapping around the urine conduit in a direction towards the first urine inlet during removal of the catheter through the urethra.

16. The intermittent catheter as claimed in claim 2, wherein urine conduit comprises a side wall and the first urine inlet comprises a plurality of holes formed in said side wall.

17. The intermittent catheter as claimed in claim 16, wherein the plurality of holes are located at substantially the same longitudinal position along the urine conduit.

18. The intermittent catheter as claimed in claim 14, wherein an edge of the first urine inlet is formed with a radius that is at least 0.3 mm or at least 0.4 mm or at least 0.5 mm or at least 0.6 mm.

19. The intermittent catheter as claimed in claim 13, wherein the tip part is rounded.

20. The intermittent catheter as claimed in claim 14, wherein the tip part is affixed to the outlet tube in a manner such that it forms and retains a fluid communication between the first urine inlet and the urine outlet.

* * * * *